United States Patent
Buechler

(10) Patent No.: US 11,851,713 B2
(45) Date of Patent: Dec. 26, 2023

(54) ASSESSING COLORECTAL CANCER MOLECULAR SUBTYPE AND USES THEREOF

(71) Applicant: University of Notre Dame Du Lac, South Bend, IN (US)

(72) Inventor: Steven Buechler, Granger, IN (US)

(73) Assignee: University of Notre Dame du Lac, South Bend, IN (US)

( * ) Notice: Subject to any disclaimer, the term of this patent is extended or adjusted under 35 U.S.C. 154(b) by 654 days.

(21) Appl. No.: 17/014,910

(22) Filed: Sep. 8, 2020

(65) Prior Publication Data

US 2020/0407803 A1 Dec. 31, 2020

Related U.S. Application Data

(63) Continuation-in-part of application No. PCT/US2019/021234, filed on Mar. 7, 2019, and a continuation-in-part of application No. PCT/US2019/021237, filed on Mar. 7, 2019.

(60) Provisional application No. 62/640,157, filed on Mar. 8, 2018.

(51) Int. Cl.
| | | |
|---|---|---|
| *C07H 21/02* | (2006.01) | |
| *C12Q 1/6886* | (2018.01) | |
| *G16H 20/40* | (2018.01) | |
| *G16H 70/60* | (2018.01) | |
| *G16H 10/40* | (2018.01) | |
| *G16H 50/20* | (2018.01) | |
| *G16B 25/10* | (2019.01) | |
| *G16B 40/00* | (2019.01) | |
| *G16B 30/00* | (2019.01) | |

(52) U.S. Cl.
CPC ............ *C12Q 1/6886* (2013.01); *G16B 25/10* (2019.02); *G16B 30/00* (2019.02); *G16B 40/00* (2019.02); *G16H 10/40* (2018.01); *G16H 20/40* (2018.01); *G16H 50/20* (2018.01); *G16H 70/60* (2018.01); *C12Q 2600/112* (2013.01); *C12Q 2600/118* (2013.01); *C12Q 2600/156* (2013.01); *C12Q 2600/158* (2013.01)

(58) Field of Classification Search
CPC ................... C12Q 2600/158; C12Q 2600/156
See application file for complete search history.

(56) References Cited

U.S. PATENT DOCUMENTS

2010/0190173 A1  7/2010  Cowens et al.

FOREIGN PATENT DOCUMENTS

WO  2017182656 A1  10/2017

OTHER PUBLICATIONS

Linnekamp et al. Consensus Molecular Subtypes Of Colorectal Can Are Recapitulated in In Vitro And In Vivo Models' Cell Death & Differentiation, Jan. 5, 2018: vol. 25, No. 3, pp. 616-633; abtract; p. 631, col. 2, second paragraph. https://doi.org/10.1038/s41418-017-0011-5.

Buechler, et al. ColoType: a forty gene signature for consensus molecular subtyping of colorectal cancer tumors using whole-genome assay or targeted RNA-sequencing, Scientific Reports, 2020, 10:12123.

Guinney, et al. The consensus molecular subtypes of colorectal cancer, Nature Medicine, vol. 1, No. 11, Nov. 2015, pp. 1350-1363.

*Primary Examiner* — Amy H Bowman
(74) *Attorney, Agent, or Firm* — Denise L. Mayfield; DYKEMA GOSSETT PLLC

(57) ABSTRACT

Disclosed are genetic methods and tools for colon cancer disease classification in disease subtypes, CMS1, CMS2, CMS3, CMS4, as well as improved methods for rapid, more accurate, and more reliably reproducible disease subtype determination. Tailored treatment protocols are also provided, employing the predicted CMS of the subject sample. Genetic sequence binding targets for some or all of these gene panels may be affixed to a solid substrate, and included as part of a screening tool and/or diagnostic kit. The expression levels of the genes may be assessed to provide a genetic signature for a subtype or lack of subtype (CMS1, CMS2, CMS3, CMS4, combination subtype). The methods employ a scoring system, wherein a score is derived from the genetic expression profile/signature of the panel of selected genes, and a qualifying continuous score for each CMS subtype is determined against a predictive threshold for each colon cancer subtype.

17 Claims, 8 Drawing Sheets

ASSESSING COLORECTAL CANCER MOLECULAR SUBTYPE AND USES THEREOF

CROSS-REFERENCE TO RELATED APPLICATIONS

This application claims the benefit of and priority to U.S. Provisional Patent Application No. 62/640,157, filed on Mar. 8, 2018, entitled "ColotypeR: A Genomic Panel to Predict Molecular Subtype and Risk of Recurrence of a Colorectal Cancer Tumor", the entirety of which is incorporated by reference herein, to PCT application WO/2019173647, filed Mar. 7, 2019, and to WO/2019173644, filed Mar. 7, 2019, the disclosures of which are incorporated herein in their entirety.

BACKGROUND

Technical Field: The present disclosure relates to products and methods for determining a molecular subtype and/or risk of recurrence of a colorectal cancer for determining and/or administering a treatment protocol based on the molecular subtype and/or risk of recurrence.

The Relevant Technology: Colorectal cancer is the fourth most common type of cancer in the United States and is second only to lung cancer as a cause of cancer-related deaths (see e.g., seer(dot)cancer(dot)gov/statfacts/html/colorect(dot)html). Only 65% of colorectal cancer patients survive for five years after diagnosis. Colon cancer is highly heterogeneous in prognosis and response to treatment. Clinical experience and colon cancer research have led to the understanding that colon cancer is not one disease but occurs as several different subtypes. These subtypes are distinguished by distinct patterns of gene expression that influence or determine tumor biology. Between 2010 and 2014 many papers were published describing methods of classifying colon tumors into molecularly distinct subtypes. Recognizing similarities in many of these subtyping systems, a consortium of experts was formed to derive one subtyping system that inherits the best features from each system. This consortium published the consensus molecular subtypes (CMS) for colon cancer in 2015.

The consensus molecular subtype (CMS) classification system divides colon cancers into 5 district groups, called subtypes, each with distinct biologies and molecular characteristics: CMS1 (MSI Immune), CMS2 (Canonical), CMS3 (Metabolic), CMS4 (Mesenchymal) and Mixed. Publication of this standard classification launched aggressive searches for drugs that are effective in specific CMS subtypes. For example, PD-L 1 inhibitors (such as Keytruda®) are likely effective in many CMS1 tumors, but not in CMS4 tumors; and anti-angiogenic agents (such as Avastin®) are likely effective in CMS4 tumors but not CMS1 tumors. The CMS subtype system is very likely to play a major role in colon cancer treatment selection in the near future.

Clinical trials have shown that various chemotherapeutics benefit some colorectal cancer patients, but not others. To date, no agents have exhibited widespread effectiveness for all types of colorectal cancer. For example, the most widely used form of chemotherapy in colon cancer (fluorouracil and folinic acid) failed to reduce the risk of recurrence for stage II colon cancer in the QUASAR trial (Quasar Collaborative Group et al. 2007). Consequently, the National Comprehensive Cancer Network (NCCN) Guidelines for Colon Cancer (see www(dot)nccn(dot) org/professionals/physician_gls/pdf/colon (dot)pdf) recommends treating stage 11 colon cancer with observation alone (after surgical removal of tumors); not because expected survival is good—expected survival is only 71% after 5 years—but because no drug seems to be universally beneficial. Conversely, some healthcare providers elect to treat stage II colon cancer with popular or emerging chemotherapeutics as a matter of course, even though the CMS classification and/or risk of recurrence for the cancer might suggest an alternative treatment protocol or course of action.

For colorectal cancer patients, including those at high risk of recurrence and/or those with stage II or stage IM colon cancer, not knowing the CMS subtype and/or the risk of recurrence of their cancer may slow or even prevent them from identifying and receiving a life-saving drug. Moreover, subjecting patients with a low risk of relapse to any form of chemotherapy or other treatment would needlessly expose them to the drug's toxic effects. Some stage II colon cancer patients, for example, may have a CMS subtype of cancer for which chemotherapy (e.g., before or after surgical extraction) would be (highly) beneficial, while others would benefit but little from chemotherapy and might needlessly be exposed to the drug's toxic effects. While the NCCN Guidelines for Colon Cancer recommend treating stage H1 colon cancer with observation alone, this fails to account for the different CMS classifications of the colorectal cancer, which can inform and even determine a more effective and more specific treatment protocol or decision, including if to treat and with what drug(s) to treat. Similarly, CMS classification of the colorectal cancer may help to confirm a decision not to treat and add peace of mind to doctors, patients, and family members. Moreover, a patient with a low recurrence risk colorectal cancers may not benefit significantly from chemotherapy, while patients with high(er) recurrence risk colorectal cancers—even stage II colorectal cancers, for which treatment is not usually recommended—may benefit greatly from treatment.

Although the CMS classification system shows much clinical promise for influencing treatment selection, there are significant hurdles to identifying the CMS subtype of patient's tumor in a normal clinical setting. For example, the methodology and algorithm used by the consortium uses nearly 700 genes to distinguish between the CMS 1-4 subtypes. Assessing the gene expression (or mRNA transcript) levels of these nearly 700 genes is costly, time-consuming, and labor intensive, which complicates adaptation to a clinically applicable diagnostic technology. In particular, the established method for determining a tumor's CMS type requires analysis of tumor tissues using microarray systems, which can be expensive to acquire, operate, maintain, and replace and are typically implemented using a fresh-frozen tumor sample, while standard clinical practice is to preserve tissue in formalin-fixed paraffin-embedded (FFPE) blocks. The authors of the consortium publication admit, however, that their system may not perform well with gene expression measured from FFPE tissue. The use of microarray-based data acquisition platforms for such large numbers of genetic elements can be time-consuming and labor intensive. Similar implementation issues exist for determining a colorectal cancer's risk of recurrence in a clinically-feasible manner.

Accordingly, there are a number of disadvantages in conventional consensus molecular subtype (CMS) determination for colorectal cancer tumors that can be addressed. In particular, there is a critical need for a time- and cost-effective clinical test to determine the consensus molecular subtype, the microsatellite instability, and subtype-specific prognosis for colorectal cancer tumors.

BRIEF SUMMARY

The present disclosure relates to products and methods for determining a molecular subtype and/or risk of recurrence of a colorectal cancer and for determining and/or administering a treatment protocol based on the molecular subtype and/or risk of recurrence. By understanding the CMS subtype and/or risk of recurrence of the cancer, patients and healthcare providers can make informed, cancer treatment-related healthcare decisions based on the biology underlying the patient's cancer. Subtype-specific and/or recurrence risk-related cancer treatments based on these determinations can improve patient outcomes, improve quality of life, reduce treatment delay and/or duration, reduce unnecessary side effects and/or drug toxicity, reduce healthcare costs, and so forth.

While each subtype was originally characterized by hundred(s) of genes expressed in the tumor(s) or cancer cell(s), measuring the expression level of hundreds of genes in a clinical setting in order to elucidate the CMS of a colorectal cancer tumor or tissue sample can be prohibitively expensive, time-consuming, and technically challenging. For instance, the full gene expression profile of a colorectal cancer tissue sample is typically assessed by microarray or RNA sequencing, which are typically executed using a fresh-frozen tumor sample, instead of a formalin-fixed paraffin-embedded (FFPE) blocks according to standard practice.

Embodiments of the present disclosure solve one or more problems in the art with products, systems, and methods for determining the CMS and/or risk of recurrence of a colorectal cancer in a clinically relevant and reasonable manner. Better informed treatment plans and options may then be considered by the healthcare provider. In this manner, a more appropriate and highest potential patient responsive treatment option more closely tailored (e.g., personalized) to the subject/patient than previously provided, may be selected, as part of an appropriate colorectal cancer treatment protocol based on the determined CMS classification of subtype and/or risk of recurrence of the colon cancer. CMS classification and/or risk of recurrence determined through embodiments of the present disclosure can influence, inform, and/or determine doctor/patient choices with regards to administering treatment protocols. Doctors and patients who might otherwise have elected to treat a colorectal cancer with observation only (following or instead of surgical removal of identified cancer tumors or tissue, for example) may now understand and/or administer a more-effective treatment protocol, which may include treating with chemotherapy and, preferably, a chemotherapy specific for the CMS and/or risk of recurrence of the colorectal cancer, based at least in part on the CMS and/or (high) risk of recurrence of the colorectal cancer. Similarly, doctors and patients who might otherwise have elected to treat colorectal cancer with chemotherapy may now understand and/or administer a more-effective treatment protocol, which may include observation only, based at least in part on the CMS and/or (low) risk of recurrence of the colorectal cancer. Moreover, doctors and patients who might otherwise have elected to treat colorectal cancer with a particular (widely used or generally-accepted) chemotherapy may now understand and/or administer a more-effective treatment protocol, which may include administering a chemotherapy specific for the CMS and/or risk of recurrence of the colorectal cancer, based at least in part on the CMS and/or risk of recurrence of the colorectal cancer.

The CMS of a colorectal cancer is generally defined by the expression of hundreds, if not thousands of genes. In some embodiments of the present disclosure, through mathematical transformation of raw gene expression values into CMS-predictive scores and, where appropriate, application of a CMS classification protocol, the expression level(s) of as few as three highly-predictive genes (per CMS) can serve as a representative or surrogate for the entire CMS-predictive expression profile of the cancer tumor or tissue in order to accurately distinguish between subtypes and determine the CMS of the colorectal cancer based on the CMS scores. In some embodiments, because the expression level of relatively few genes are being assessed, RNA can be extracted from cancer tissue preserved in a FFPE sample block and the expression levels of the suitable and manageable number of genes can be quantified through rapid, inexpensive detection means, such as reverse transcription-polymerase chain reaction (RT-PCR) or RNA sequencing (RNA-seq), instead of microarray based platforms. In similar fashion, through mathematical transformation of raw gene expression values into a recurrence risk score, the expression level(s) of as few as fifteen highly-predictive genes for colorectal cancer recurrence can serve as a representative or surrogate for the entire prognostic recurrence expression profile of the cancer tumor or tissue in order to accurately discern risk of relapse.

Moreover, the use and suitability of the reduced number of highly-predictive genes provides ease, simplicity, efficiency, and cost-effectiveness in showing "analytic validity", a quality control requirement for a commercial diagnostics in various countries, including in the United States. Analytic validity studies the dynamic range, variance and other features of each mRNA species in the diagnostic, and how changes in each gene effects the final test result. Showing analytic validity of a diagnostic test containing or relying on hundred(s) of genes may be difficult, expensive, and time-consuming, or altogether commercially impractical. Thus, embodiments of the present disclosure solve one or more problems in the art by providing an in vitro diagnostic that can be (easily or feasibly) approved by respective government regulatory agencies, such as the U.S. FDA.

Embodiments of the present disclosure also solve one or more problems in the art with products, systems, and methods for determining and reporting the CMS and/or risk or recurrence (or data or information related to the CMS and/or risk or recurrence) of a colorectal cancer in a clinically relevant and reasonable manner, so that patients and healthcare providers can make informed decisions about determining and/or administering an appropriate colorectal cancer treatment protocol based on the determined CMS and/or risk of recurrence. In some embodiments of the present disclosure, a report is generated following analysis of cancer gene expression levels. The report can display, indicate or include value(s) representing the probability of the cancer being of one or more CMS and/or the probability that the cancer will recur in the patient. In some embodiments, the report can display, indicate or include a determination of CMS and/or risk of recurrence. In some embodiments, a CMS report can display, indicate or include a CMS determination, providing the CMS of the colorectal cancer. In some embodiments, the report can display, indicate or include a (recommended or suggested) treatment protocol(s) based at least in part on the CMS determination, or a (recommended or suggested) treatment protocol(s) specific for the CMS of the colorectal cancer. In some embodiments, a risk report can display, indicate or include a probability of recurrence for the colorectal cancer. In some embodiments, a risk report can display, indicate or include a (recommended or suggested) treatment protocol(s) based at least in part on the probability of recurrence for the colorectal cancer.

In one or more embodiments, raw expression data for genes representative of each CMS can be transformed into a comparative and/or continuous CMS score (0-100 or 0-1) representing the (absolute) probability that the analyzed cancer tissue belongs to the respective CMS subtype. Ranking procedures and classification protocol can be used to compare CMS probability scores for each CMS subtype and classify the colorectal cancer into a subtype (CMS1, CMS2, CMS3, CMS4, or mixed/unclassified). Accordingly, some embodiments of the present disclosure include products, systems, and/or methods for using the expression levels of relatively few genes that can recapitulate the gene expression signatures of respective CMS subtypes to generate CMS scores that can be compared in order to assign or classify colorectal cancer into a CMS classification.

Similarly, in some embodiments, raw expression data for genes representative of relapse risk can be transformed into a comparative and/or continuous risk score (0-100 or 0-1) representing the (absolute) probability that the analyzed cancer tissue will return or recur in the patient. Accordingly, some embodiments of the present disclosure include products, systems, and/or methods for using the expression levels of relatively few genes that can recapitulate the gene expression signature of a colorectal cancer recurrence risk profile to generate a risk score that represents colorectal cancer relapse probability and/or predicts relapse.

In a first aspect, the present invention comprises a method of classifying a human colorectal cancer, tumor or tissue into a consensus molecular subtype (CMS).

In a further aspect, the present invention comprises a method of classifying a human colorectal cancer, tumor or tissue into a consensus molecular subtype (CMS) based on the CMS score of an abbreviated gene expression profile.

In a further aspect, the present invention comprises a method of diagnosing a human colorectal cancer, tumor or tissue as belonging to a consensus molecular subtype (CMS).

In a further aspect, the present invention comprises a method of determining a colorectal cancer, tumor or tissue treatment protocol.

In a further aspect, the present invention comprises a method of determining a suitable or recommended colorectal cancer treatment protocol based at least in part on the consensus molecular subtype (CMS) of a colorectal cancer, tumor or tissue.

In a further aspect, the present invention comprises a method of prescribing a suitable colorectal cancer treatment protocol based at least in part on the consensus molecular subtype (CMS) of a colorectal cancer, tumor or tissue.

In a further aspect, the present invention comprises a method of computationally-transforming raw gene expression levels of genes expressed in a colorectal cancer, tumor or tissue sample into one or more consensus molecular subtype (CMS) scores.

In a further aspect, the present invention comprises a method of computationally-transforming raw gene expression levels of genes expressed in a colorectal cancer, tumor or tissue sample into one or more consensus molecular subtype (CMS) scores representative of a probability that the CMS of the colorectal cancer, tumor or tissue is one of CMS1, CMS2, CMS3, CMS4, or mixed subtype.

In a further aspect, the present invention comprises a method of computationally-transforming raw gene expression levels of a clinically-practical number of clinically-relevant genes expressed in a colorectal cancer, tumor or tissue sample into one or more consensus molecular subtype (CMS) scores representative of a probability that the CMS of the colorectal cancer, tumor or tissue is one of CMS1, CMS2, CMS3, CMS4, or mixed subtype.

In a further aspect, the present invention comprises a composition or composition of matter comprising a mixture of cDNA molecules.

In any one or combination of the forgoing aspects, a method, system, kit, or composition according to the present invention can comprise one or more steps, elements, components, or members. It is noted that any of the one or more steps, elements, components, or members of any particular method, system, kit, or composition according to one aspect of the present invention or of the present disclosure is, or may be, applied or applicable to (any) other method(s), system(s), kit(s), or composition(s) according to (any) other aspect(s) of the present invention or of the present disclosure. Moreover, elements, components, or members of any particular system, kit, or composition is, or may be, applied or applicable to (any) method according to (any) other aspect(s) of the present invention or of the present disclosure, and so on and so forth. Thus, the listing, recitation, or disclosure of a particular combination of one or more steps, elements, components, or members of any particular method, system, kit, or composition according to one aspect of the present invention or of the present disclosure is not intended to limit the incorporation or inclusion of said steps, elements, components, or members to only said method, system, kit, or composition. Listing of exemplary and/or illustrative aspects, embodiments, and/or implementations of the present disclosure and/or invention(s) thereof.

The following listing provides exemplary and/or illustrative aspects, embodiments, and/or implementations of the present disclosure and/or invention(s) thereof. The listing is provided to disclose and describe certain features of the various exemplary and/or illustrative aspects, embodiments, and/or implementations of the present disclosure and/or invention(s) fhereof. Each feature, regardless of how it is presented in the listing, is intended to be disclosed and described independently and not only in the particular combination disclosed herein. Thus, the separation of one or more features from other feature(s) disclosed in connection therewith should not be view or taken as an intermediate generalization of an aspects, embodiments, and/or implementations of the present disclosure and/or invention(s) thereof.

In one embodiment, a continuous score method for providing a colon cancer disease predicted consensus molecular subtype (CMS) is provided, comprising contacting a genetic sample with a plurality of genetic sequence binding targets and measuring expression levels of a panel of genes having specificity for the binding targets, said panel of genes comprising at least three genes for each of four consensus molecular subtypes CMS1, CMS2, CMS3 and CMS4, wherein the gene subset for each of the four consensus molecular subtypes comprise: AXIN2, SEMA5A, CDHR1, CTTNBP2, WARS, HPSE, ATP9A, GNLY, DACH1, EMP2AIP1 for the CMS1 gene subset; POFUT1, QPRT, PLAGL2, CEL, TRIB2, DDX27, DUSP4, FSCN1, OSER1, and LYZ for the CMS2 gene subset; TIMP3, CAPN9, VAV2, FCGBP, FBN1, IGFBP5, SPINK4, REG4, CEBPB, and CLCA1 for the CMS3 gene subset; and MGP, AOC3, TINS1, CCDC80, SPOCK1, LMOD1, PLN, AKAP12, FERMT2, and HSPB8 for the CMS4 gene subset; obtaining a gene expression signature value from the expression levels of at least three genes of the CMS1, CMS2, CMS3 and CMS4 gene subsets from the genetic sample; comparing the gene expression signature value to a predicted threshold for the CMS subtype to provide a continuous CMS score for each CMS subtype; selecting qualifying CMS scores that are above the predicted threshold for the CMS subtype; ranking the qualifying CMS scores to provide ranked qualifying CMS scores for the genetic sample; and assigning one or more of a colon cancer disease predicted CMS to the genetic sample from the ranked qualifying CMS scores for the genetic sample, wherein the predicted CMS comprises the CMS of the highest ranked qualifying CMS score. This continuous score method provides a predicted CMS with improved reproducibility for a genetic sample compared to a CMS classification of a genetic sample without the continuous score method. In these embodiments, the number of genes to which targets will be provided and gene expression assessed are targets to at least 12 genes, the 12 genes comprising at least 3 genes from each of the four CMS gene subsets, CMS1, CMS2, CMS3 and CMS4 described above.

In another embodiment, a method for providing an enhanced treatment plan for a subject having a colon cancer disease predicted consensus molecular subtype (CMS) is provided, comprising identifying presence or absence of a colon cancer disease from a genetic sample of the subject, the genetic sample having a predicted CMS according to the continuous score method, providing the subject having a predicted CMS an enhanced treatment plan for the predicted CMS colon cancer disease, wherein the enhanced treatment plan provides an improved anti-colon cancer disease treatment for the subject's colon cancer disease subtype compared to an anti-cancer disease treatment for the subject's colon cancer disease subtype without a colon cancer disease subtype having a determined continuous score.

In another embodiment, a method of administering a treatment protocol specific for a colorectal cancer to a cancer patient or determining a treatment protocol specific for the colorectal cancer is provided wherein the method comprises: obtaining a colorectal cancer tissue sample of unknown consensus molecular subtype (CMS) from a cancer patient; extracting RNA transcripts from the colorectal cancer tissue sample and quantifying an expression level of at least twelve of the RNA transcripts, the at least twelve RNA transcripts comprising at least three RNA transcripts from each of four groups of genetic elements, each of the four groups of genetic elements defining a CMS gene expression profile specific for a different one of CMS 1, CMS2, CMS3, and CMS4; determining, based on the expression level of each of the at least three RNA transcripts from a first group of the four groups of genetic elements, a first CMS score representative of a probability that the CMS of the colorectal cancer is CMS1 determining, based on the expression level of each of the at least three RNA transcripts from a second group of the four groups of genetic elements, a second CMS score representative of a probability that the CMS of the colorectal cancer is CMS2; determining, based on the expression level of each of the at least three RNA transcripts from a third group of the four groups of genetic elements, a third CMS score representative of a probability that the CMS of the colorectal cancer is CMS3; determining, based on the expression level of each of the at least three RNA transcripts from a fourth group of the four groups of genetic elements, a fourth CMS score representative of a probability that the CMS of the colorectal cancer is CMS4; and generating a report indicating one or more of: the first, second, third, and/or fourth CMS scores; and the probability that the CMS of the colorectal cancer is CMS1, CMS2, CMS3, and/or CMS4, wherein one or more of the first, second, third, and/or fourth CMS scores, and the probability that the CMS of the colorectal cancer is CMS1, CMS2, CMS3, and/or CMS4 signifies, at least in part, a treatment protocol specific for the colorectal cancer.

In some embodiments the report may be visually displayed on a graphical user interface, the report being generated by a computer system coupled to the graphical user interface, the computer system comprising: one or more processor(s); and one or more computer-readable hardware storage devices having stored thereon computer-executable instructions that are executable by the one or more processor(s) to cause the computer system to visually display the report.

In other embodiments, each step of determining a respective CMS score comprises: matching the expression level of each RNA transcript from a respective group of genetic elements with a reference expression level of said RNA transcript in a reference data set, each reference expression level corresponding to a scaled value representing the probability that the CMS of a colorectal cancer expressing said RNA transcript at said reference expression level is one of CMS1, CMS2, CMS3, and CMS4; and calculating respective CMS scores based on the respective scaled values for each of the RNA transcripts from the respective group of genetic elements.

As part of some aspects of the claimed method, the reference data set comprises a curve fit of a population of the respective RNA transcript, the curve fit reflecting the probability that the CMS of a colorectal cancer expressing said RNA transcript at various reference expression levels is one of CMS1, CMS2, CMS3, and CMS4.

Calculating the respective CMS scores comprises calculating a mean of the respective scaled values for each of the RNA transcripts from the respective group of genetic elements. In one embodiment, calculating the respective CMS scores comprises: producing respective CMS pre-scores that inform membership in a respective CMS subtype by ranking risk scores of genes by level of significance in predicting the CMS subtype in the respective reference data set; and selecting at least three of the genes corresponding to at least three of the highest rank genes in the respective reference data set that are also among the highest ranked genes in a second respective reference data set. The method may further comprise administering the treatment protocol specific for the colorectal cancer to the cancer patient.

The treatment protocol specific for the colorectal cancer is further determined by one or more of the stage of the cancer, the grade of the cancer, the metastatic state of the cancer, and the presence or absence of one or more genetic mutations in patient or tissue sample.

The colorectal cancer tissue sample may comprise a formalin-fixed paraffin-embedded (FFPE) colorectal cancer tissue sample. Extracting RNA transcripts from the colorectal cancer tissue sample will comprise extracting RNA transcripts from the formalin-fixed paraffin-embedded (FFPE) colorectal cancer tissue sample.

Quantifying the expression level of a particular gene may comprise performing reverse transcription-polymerase chain reaction (RT-PCR). Alternatively, quantifying the expression level of a gene may comprise performing RNA sequencing.

In the practice of the method, each CMS score may be described as comprising a number having a scaled value between 0 and 1, or between 0 and 100, or an equivalent thereof.

The method may further comprise applying a CMS classification protocol to determine the CMS of the colorectal cancer based on a plurality of CMS scores, the method comprising: (i) classifying the colorectal cancer with a CMS determination of CMS1 when the first CMS score and the fourth CMS score are each above respective predictive thresholds; (ii) classifying the colorectal cancer with a CMS determination of CMS4 when the second CMS score and the fourth CMS score are each above respective predictive thresholds and when (i) does not apply; (iii) selecting from among the first, second, third, and fourth CMS scores a maximal CMS score and classifying the colorectal cancer with a CMS determination selected from the group consisting of CMS1, CMS2, CMS3, and CMS4 based on or corresponding to the maximal CMS score when the maximal CMS score is above the predictive threshold and when neither (i) nor (ii) applies; (iv) classifying the colorectal cancer with a CMS determination of mixed subtype or unclassified subtype when the first, second, third, and fourth CMS scores are each below the predictive threshold.

In some embodiments of the method, the CMS determination indicates, at least in part, a treatment protocol specific for the CMS of the colorectal cancer.

In particular embodiments of the method, the treatment protocol specific for the CMS of the colorectal cancer is further determined by one or more of the stage of the cancer, the grade of the cancer, the metastatic state of the cancer, and the presence or absence of one or more genetic mutations in patient or tissue sample.

Some embodiments of the method may further comprise administering the treatment protocol to the cancer patient based at least in part on the CMS determination.

In some aspects, the report provided and/or generated with the method indicates one or more of: the CMS determination; the CMS of the colorectal cancer, a treatment protocol based at least in part on the CMS determination; and a treatment protocol specific for the CMS of the colorectal cancer.

In a particular aspect of the method, the step of determining, based on the expression level of each of the at least five RNA transcripts from a first group of the four groups of genetic elements, a CMS score representative of a probability that the CMS of the colorectal cancer is CMS1, comprises: (i) matching the expression level of each RNA transcript from the first group of genetic elements with a corresponding reference expression level of said RNA transcript in a CMS1 reference data set for said RNA transcript, each reference expression level corresponding to a respective scaled value in the respective CMS1 reference data set, each scaled value in the respective CMS1 reference data set representing a probability that the CMS of a colorectal cancer expressing the respective RNA transcript at the respective reference expression level is CMS1; and (ii) calculating the first CMS score based on the respective scaled values for each of the RNA transcripts from the first group of genetic elements. In a particular aspect, the probability that the CMS is CMS2 is provided by determining, based on the expression level of each of the at least five RNA transcripts from a second group of the four groups of genetic elements, a second CMS score representative of a probability that the CMS of the colorectal cancer is CMS2. This step comprises: (i) matching the expression level of each RNA transcripts from the second group of genetic elements with a corresponding reference expression level of said RNA transcript in a CMS2 reference data set for said RNA transcript, each reference expression level corresponding to a respective scaled value in the respective CMS2 reference data set, each scaled value in the respective CMS2 reference data set representing a probability that the CMS of a colorectal cancer expressing the respective RNA transcript at the respective reference expression level is CMS2; and (ii) calculating the second CMS score based on the respective scaled values for each of the RNA transcripts from the second group of genetic elements. As part of the method, the step of determining, based on the expression level of each of the at least five RNA transcripts from a third group of the four groups of genetic elements is provided, to provide a third CMS score representative of a probability that the CMS of the colorectal cancer is CMS3. This step may comprise: (i) matching the expression level of each RNA transcripts from the third group of genetic elements with a corresponding reference expression level of said RNA transcript in a CMS3 reference data set for said RNA transcript, each reference expression level corresponding to a respective scaled value in the respective CMS3 reference data set, each scaled value in the respective CMS3 reference data set representing a probability that the CMS of a colorectal cancer expressing the respective RNA transcript at the respective reference expression level is CMS3; and (ii) calculating the third CMS score based on the respective scaled values for each of the RNA transcripts from the third group of genetic elements. In a further embodiment of the method, the step of determining, based on the expression level of each of the at least five RNA transcripts from a fourth group of the four groups of genetic elements, a fourth CMS score representative of a probability that the CMS of the colorectal cancer is CMS4, is provided. This step comprises: (i) matching the expression level of each RNA transcripts from the fourth group of genetic elements with a corresponding reference expression level of said RNA transcript in a CMS4 reference data set for said RNA transcript, each reference expression level corresponding to a respective scaled value in the respective CMS4 reference data set, each scaled value in the respective CMS4 reference data set representing a probability that the CMS of a colorectal cancer expressing the respective RNA transcript at the respective reference expression level is CMS4; and (ii) calculating the fourth CMS score based on the respective scaled values for each of the RNA transcripts from the fourth group of genetic elements.

In yet other embodiments, calculation of the first CMS score comprises calculating the mean of all the of scaled values for each of the RNA transcripts from the first group of genetic elements; calculating the second CMS score comprises calculating the mean of all the of scaled values for each of the RNA transcripts from the second group of genetic elements; calculating the third CMS score comprises calculating the mean of all the of scaled values for each of the RNA transcripts from the third group of genetic elements; and calculating the fourth CMS score comprises calculating the mean of all the of scaled values for each of the RNA transcripts from the fourth group of genetic elements.

In some embodiments of the method, calculating the first CMS score further comprises: producing a first CMS pre-score that informs membership in CMS1 by ranking risk scores of genes by level of significance in predicting membership in CMS1 in the CMS1 reference data set; and selecting at least three of the genes corresponding to at least three of the highest rank genes in the CMS1 reference data set that are also among the highest ranked genes in a second CMS1 reference data set; calculating the second CMS score further comprises: producing a second CMS pre-score that informs membership in CMS2 by ranking risk scores of genes by level of significance in predicting membership in CMS2 in the CMS2 reference data set; and selecting at least three of the genes corresponding to at least three of the highest rank genes in the CMS2 reference data set that are also among the highest ranked genes in a second CMS2 reference data set; calculating the third CMS score further comprises: producing a third CMS pre-score that informs membership in CMS3 by ranking risk scores of genes by level of significance in predicting membership in CMS3 in the CMS3 reference data set; and selecting at least three of the genes corresponding to at least three of the highest rank genes in the CMS3 reference data set that are also among the highest ranked genes in a second CMS3 reference data set; and calculating the fourth CMS score further comprises: producing a fourth CMS pre-score that informs membership in CMS4 by ranking risk scores of genes by level of significance in predicting membership in CMS4 in the CMS4 reference data set; and selecting at least three of the genes corresponding to at least three of the highest rank genes in the CMS4 reference data set that are also among the highest ranked genes in a second CMS4 reference data set.

In some embodiments of the method, the at least twelve RNA transcripts comprising at three RNA transcripts from each of the four groups of genetic elements. Alternatively, where the method employs at least sixteen RNA transcripts, at least four RNA transcripts from each of the four groups of genetic elements is employed. In embodiments where there are used at least twenty RNA transcripts, the at least twenty RNA transcripts comprise at least five RNA transcripts from each of the four groups of genetic elements. The four groups of genetic elements is defined as the genetic elements or genes identified within the four subtypes of colon cancer CMS1, CMS2, CMS3, and CMS4. These gene sets have been identified to be expressed in a population of colorectal cancers having a defined CMS subtype, selected from a different one of CMS1, CMS2, CMS3, and CMS4.

In some embodiments, the method provides for a panel of genes that comprises or consists of between five and twenty-five genes expressed in a population of colorectal cancers having a CMS selected from a different one of CMS1, CMS2, CMS3, and CMS4.

By way of example, according to the present methods and compositions, a first group of genes may be described as comprising or consisting of a gene set represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; a second group of genes may be described as comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; a third group of genes may be described as comprising or consisting of genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and a fourth group of genes may be described as comprising or consisting of genes represented by or corresponding to ENTREZ IDs 23414, 30008, 27295, 2737, 143903, 154810, 11037, 7145, 9590, 5178, 23194, 4256, 10000, 1410, 862, 5740, 4286, 83871, 421 1, 165, 6695, 1292, 9353, 4131, 8639, 5549, 54796, 147906, and 8828.

In some embodiments, the method will provide for the measurement and/or assessment of expression levels of genes from at least three RNA transcripts from the first group of genes represented by or corresponding to ENTREZ IDs 9219, 57168, 7105, 23475, and 998; the at least three RNA transcripts from the second group comprise or consist of RNA transcripts of the genes represented by or corresponding to ENTREZ IDs 112858, 5326, 23509, 6780, and 1846; the at least three RNA transcripts from the third group comprise or consist of RNA transcripts of the genes represented by or corresponding to ENTREZ IDs 7078, 80150, 84189, 84666, and 5937; and the at least three RNA transcripts from the fourth group comprise or consist of RNA transcripts of the genes represented by or corresponding to ENTREZ IDs 143903, 23414, 11037, 27295, and 165.

In yet another aspect, a method of accurately determining a consensus molecular subtype of a colorectal cancer from a cancer patient is provided. In one embodiment, the method comprises obtaining and/or determining an expression level of at least three colorectal cancer RNA transcripts from a first group of genetic elements (genes), the first group of genetic elements (genes) comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 401474, 139322, 1783, 29966, 80183, 8019, 3549, 27330, and 10451; 9554, 1602, 57168, obtaining and/or determining an expression level of at least three colorectal cancer RNA transcripts from a second group of genetic elements (genes), the second group of genetic elements comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; obtaining and/or determining an expression level of at least three colorectal cancer RNA transcripts of and/or from a third group of genetic elements (genes), the third group of genetic elements comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; obtaining and/or determining an expression level of at least three colorectal cancer RNA transcripts from a fourth group of genetic elements (genes), the fourth group of genetic elements (genes) comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 1, 165, 6695, 1292, 9353, 4131, 8639, 5549, 54796, 147906, and 8828; determining, based on the expression level of each of the at least three RNA transcripts from the first group of genetic elements, a first CMS score representative of a probability that the CMS of the colorectal cancer is CMS1; determining, based on the expression level of each of the at least three RNA transcripts from the second group of genetic elements, a second CMS score representative of a probability that the CMS of the colorectal cancer is CMS2; determining, based on the expression level of each of the at least three RNA transcripts from the third group of genetic elements, a third CMS score representative of a probability that the CMS of the colorectal cancer is CMS3; determining, based on the expression level of each of the at least three RNA transcripts from the fourth group of genetic elements, a fourth CMS score representative of a probability that the CMS of the colorectal cancer is CMS4; and generating a report indicating one or more of: the first, second, third, and/or fourth CMS scores; the probability that the CMS of the colorectal cancer is CMS1, CMS2, CMS3, and/or CMS4; and a treatment protocol specific for the colorectal cancer, wherein one or more of the first, second, third, and/or fourth CMS scores, and the probability that the CMS of the colorectal cancer is CMS1, CMS2, CMS3, and/or CMS4 indicates, at least in part, the treatment protocol specific for the colorectal cancer.

In some embodiments, the method provides for providing a report that may be visually displayed on a graphical user interface, the report being generated by a computer system coupled to the graphical user interface, the computer system comprising: one or more processor(s); and one or more computer-readable hardware storage devices having stored thereon computer-executable instructions that are executable by the one or more processor(s) to cause the computer system to visually display the report.

In some aspects of the method, each step of determining a respective CMS score comprises: matching the expression level of each RNA transcript from a respective group of genetic elements with a reference expression level of said RNA transcript in a reference data set, each reference expression level corresponding to a scaled value representing the probability that the CMS of a colorectal cancer expressing said RNA transcript at said reference expression level is one of CMS1, CMS2, CMS3, and CMS4; and calculating respective CMS scores based on the respective scaled values for each of the RNA transcripts from the respective group of genetic elements.

The reference data set may be further described as comprising a curve fit of a population of the respective RNA transcript, the curve fit reflecting the probability that the CMS of a colorectal cancer expressing said RNA transcript at various reference expression levels is one of CMS1, CMS2, CMS3, and CMS4.

As further described, the step of calculating the respective CMS scores comprises calculating a mean of the respective scaled values for each of the RNA transcripts from the respective group of genetic elements.

As may be even further defined, the step of calculating the respective CMS scores may comprise: producing a first CMS pre-score that informs membership in CMS1 by ranking risk scores of genes by level of significance in predicting membership in CMS1 in the CMS1 reference data set; and selecting at least three of the genes corresponding to at least three of the highest rank genes in the CMS1 reference data set that are also among the highest ranked genes in a second CMS1 reference data set; calculating the second CMS score further comprises: producing a second CMS pre-score that informs membership in CMS2 by ranking risk scores of genes by level of significance in predicting membership in CMS2 in the CMS2 reference data set; and selecting at least three of the genes corresponding to at least three of the highest rank genes in the CMS2 reference data set that are also among the highest ranked genes in a second CMS2 reference data set; calculating the third CMS score further comprises: producing a third CMS pre-score that informs membership in CMS3 by ranking risk scores of genes by level of significance in predicting membership in CMS3 in the CMS3 reference data set; and selecting at least three of the genes corresponding to at least three of the highest rank genes in the CMS3 reference data set that are also among the highest ranked genes in a second CMS3 reference data set; and calculating the fourth CMS score further comprises: producing a fourth CMS pre-score that informs membership in CMS4 by ranking risk scores of genes by level of significance in predicting membership in CMS4 in the CMS4 reference data set; and selecting at least three of the genes corresponding to at least three of the highest rank genes in the CMS4 reference data set that are also among the highest ranked genes in a second CMS4 reference data set.

In some embodiments, the method further comprises determining a treatment protocol specific for the colorectal cancer subtype, and, optionally, administering the treatment protocol specific for the colorectal cancer subtype to the cancer patient, wherein one or more of the first, second, third, and/or fourth CMS scores, and the probability that the CMS of the colorectal cancer is CMS1, CMS2, CMS3, and/or CMS4 indicates, at least in part, the treatment protocol specific for the colorectal cancer subtype. A treatment protocol specific for the colorectal cancer subtype may be further assessed based on the stage of the cancer, the grade of the cancer, the metastatic state of the cancer, and the presence or absence of one or more genetic mutations in a patient or tissue sample.

As part of the method, each step of obtaining an expression level of at least three RNA transcripts may be further defined as comprising extracting RNA transcripts from a colorectal cancer tissue sample from the cancer patient; and quantifying the expression level of the at least three of the RNA transcripts.

In some embodiments, a genetic sample may be extracted from a colorectal cancer tissue sample that is a formalin-fixed paraffin-embedded (FFPE) colorectal cancer tissue sample, wherein RNA transcripts are prepared from genetic material extracted from the colorectal cancer tissue sample.

As part of the method, quantifying the expression level for a particular gene comprises performing RNA sequencing and/or reverse transcription-polymerase chain reaction (RT-PCR).

As part of the method, each CMS score derived/calculated will comprise a number having a scaled value of between 0 and 1 or between 0 and 100, or any equivalent value thereof.

In some embodiments, the method may further comprise applying a CMS classification protocol to determine the CMS of the colorectal cancer based on a plurality of CMS scores, as follows: (v) classifying the colorectal cancer with a CMS determination of CMS1 when the first CMS score and the fourth CMS score are each above respective predictive thresholds; (vi) classifying the colorectal cancer with a CMS determination of CMS4 when the second CMS score and the fourth CMS score are each above respective predictive thresholds and when (i) does not apply; (vii) selecting from among the first, second, third, and fourth CMS scores a maximal CMS score and classifying the colorectal cancer with a CMS determination selected from the group consisting of CMS1, CMS2, CMS3, and CMS4 based on or corresponding to the maximal CMS score when the maximal CMS score is above the predictive threshold and when neither (i) nor (ii) applies; (viii) classifying the colorectal cancer with a CMS determination of mixed subtype or unclassified subtype when the first, second, third, and fourth CMS scores are each below the predictive threshold.

In other embodiments of the method, the step of determining the CMS score representative of the probability that the CMS of the colorectal cancer is CMS1, comprises: (iii) matching the expression level of each RNA transcripts from the first group of genetic elements with a corresponding reference expression level of said RNA transcript in a CMS1 reference data set for said RNA transcript, each reference expression level corresponding to a respective scaled value in the respective CMS1 reference data set, each scaled value in the respective CMS1 reference data set representing a probability that the CMS of a colorectal cancer expressing the respective RNA transcript at the respective reference expression level is CMS1; and (iv) calculating the first CMS score based on the respective scaled values for each of the RNA transcripts from the first group of genetic elements; the step of determining the CMS score representative of the probability that the CMS of the colorectal cancer is CMS2, comprises: (iii) matching the expression level of each RNA transcripts from the second group of genetic elements with a corresponding reference expression level of said RNA transcript in a CMS2 reference data set for said RNA transcript, each reference expression level corresponding to a respective scaled value in the respective CMS2 reference data set, each scaled value in the respective CMS2 reference data set representing a probability that the CMS of a colorectal cancer expressing the respective RNA transcript at the respective reference expression level is CMS2; and (iv) calculating the second CMS score based on the respective scaled values for each of the RNA transcripts from the second group of genetic elements; the step of determining the CMS score representative of the probability that the CMS of the colorectal cancer is CMS3, comprises: (iii) matching the expression level of each RNA transcripts from the third group of genetic elements with a corresponding reference expression level of said RNA transcript in a CMS3 reference data set for said RNA transcript, each reference expression level corresponding to a respective scaled value in the respective CMS3 reference data set, each scaled value in the respective CMS3 reference data set representing a probability that the CMS of a colorectal cancer expressing the respective RNA transcript at the respective reference expression level is CMS3; and (iv) calculating the third CMS score based on the respective scaled values for each of the RNA transcripts from the third group of genetic elements; and the step of determining the CMS score representative of the probability that the CMS of the colorectal cancer is CMS4, comprises: (iii) matching the expression level of each RNA transcripts from the fourth group of genetic elements with a corresponding reference expression level of said RNA transcript in a CMS4 reference data set for said RNA transcript, each reference expression level corresponding to a respective scaled value in the respective CMS4 reference data set, each scaled value in the respective CMS4 reference data set representing a probability that the CMS of a colorectal cancer expressing the respective RNA transcript at the respective reference expression level is CMS4; and (v) calculating the fourth CMS score based on the respective scaled values for each of the RNA transcripts from the fourth group of genetic elements.

In other embodiments, calculating the first CMS score may be described as comprising calculating the mean of all the of scaled values for each of the RNA transcripts from the first group of genetic elements; calculating the second CMS score comprises calculating the mean of all the of scaled values for each of the RNA transcripts from the second group of genetic elements; calculating the third CMS score comprises calculating the mean of all the of scaled values for each of the RNA transcripts from the third group of genetic elements; and calculating the fourth CMS score comprises calculating the mean of all the of scaled values for each of the RNA transcripts from the fourth group of genetic elements.

In some embodiments, calculating the first CMS score may be described as comprising: producing a first CMS pre-score that informs membership in CMS1 by ranking risk scores of genes by level of significance in predicting membership in CMS1 in the CMS1 reference data set; and selecting at least three of the genes corresponding to at least three of the highest rank genes in the CMS1 reference data set that are also among the highest ranked genes in a second CMS1 reference data set; calculating the second CMS score further comprises: producing a second CMS pre-score that informs membership in CMS2 by ranking risk scores of genes by level of significance in predicting membership in CMS2 in the CMS2 reference data set; and selecting at least three of the genes corresponding to at least three of the highest rank genes in the CMS2 reference data set that are also among the highest ranked genes in a second CMS2 reference data set; calculating the third CMS score further comprises: producing a third CMS pre-score that informs membership in CMS3 by ranking risk scores of genes by level of significance in predicting membership in CMS3 in the CMS3 reference data set; and selecting at least three of the genes corresponding to at least three of the highest rank genes in the CMS3 reference data set that are also among the highest ranked genes in a second CMS3 reference data set; and calculating the fourth CMS score further comprises: producing a fourth CMS pre-score that informs membership in CMS4 by ranking risk scores of genes by level of significance in predicting membership in CMS4 in the CMS4 reference data set; and selecting at least three of the genes corresponding to at least three of the highest rank genes in the CMS4 reference data set that are also among the highest ranked genes in a second CMS4 reference data set.

In some aspects, the method may be described as providing for a first group of genes comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; the second group comprises or consists of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; the third group comprises or consists of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and the fourth group comprises or consists of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 4211, 165, 6695, 1292, 9353, 4131, 8639, 5549, 54796, 147906, and 8828.

The method, wherein: the at least three RNA transcripts from the first group comprise or consist of RNA transcripts of the genes represented by or corresponding to ENTREZ IDs 9219, 57168, 7105, 23475, and 998, the at least three RNA transcripts from the second group comprise or consist of RNA transcripts of the genes represented by or corresponding to ENTREZ IDs 112858, 5326, 23509, 6780, and 1846; the at least three RNA transcripts from the third group comprise or consist of RNA transcripts of the genes represented by or corresponding to ENTREZ IDs 7078, 80150, 84189, 84666, and 5937; and the at least three RNA transcripts from the fourth group comprise or consist of RNA transcripts of the genes represented by or corresponding to ENTREZ IDs 143903, 23414, 11037, 27295, and 165.

In some aspects, a method of classifying a human colorectal cancer tumor into a consensus molecular subtype (CMS) based on a CMS score derived from an abbreviated gene expression profile is disclosed. In one embodiment, the method comprises: obtaining an expression level of at least three RNA transcripts from a colorectal cancer tissue sample, the at least three RNA transcripts being selected from a first group of genetic elements that define a first CMS profile for one of CMS1, CMS2, CMS3, and CMS4; determining, based on the expression level of each of the at least three RNA transcripts from the first group of genetic elements, a first CMS score representative of a probability that the CMS of the colorectal cancer corresponds with the CMS of the first CMS profile; and optionally, classifying the colorectal cancer with a CMS determination corresponding to the CMS of the first CMS profile based at least in part on the first CMS score, wherein the first CMS score is above a predictive threshold.

The method may further comprise obtaining an expression level of at least three RNA transcripts selected from a second group of genetic elements that define a second CMS profile for one of CMS1, CMS2, CMS3, and CMS4 that is different from the CMS of the first CMS profile, the at least three RNA transcripts from the second group of genetic elements being from the colorectal cancer tissue sample; and determining, based on the expression level of each of the at least three RNA transcripts from the second group of genetic elements, a second CMS score representative of a probability that the CMS of the colorectal cancer corresponds with the CMS of the second CMS profile. The step of classifying the colorectal cancer with a CMS determination corresponding to the CMS of the first CMS profile may be based on the second CMS score. Alternatively, the step of classifying the colorectal cancer with a CMS determination may correspond to the CMS of the first CMS profile.

In other aspects, the method may be described as comprising obtaining an expression level of at least three RNA transcripts selected from a third group of genetic elements that define a third CMS profile for one of CMS1, CMS2, CMS3, and CMS4 that is different from the CMS of the first CMS profile and the second CMS profile, the at least three RNA transcripts from the third group of genetic elements being from the colorectal cancer tissue sample; and determining, based on the expression level of each of the at least three RNA transcripts from the third group of genetic elements, a third CMS score representative of a probability that the CMS of the colorectal cancer corresponds with the CMS of the third CMS profile.

In some aspects of the method, the step of classifying the colorectal cancer with a CMS determination corresponding to the CMS of the first CMS profile may be based on the third CMS score. The method further comprising: obtaining an expression level of at least three RNA transcripts selected from a fourth group of genetic elements that define a fourth CMS profile for one of CMS1, CMS2, CMS3, and CMS4 that is different from the CMS of the first CMS profile and the second CMS profile and the third CMS profile, the at least three RNA transcripts from the fourth group of genetic elements being from the colorectal cancer tissue sample; and determining, based on the expression level of each of the at least three RNA transcripts from the fourth group of genetic elements, a fourth CMS score representative of a probability that the CMS of the colorectal cancer corresponds with the CMS of the fourth CMS profile. The method, wherein the step of classifying the colorectal cancer with a CMS determination corresponding to the CMS of the first CMS profile is further based on the fourth CMS score. The method, wherein: the at least three RNA transcripts from the first group comprise or consist of RNA transcripts of the genes represented by or corresponding to ENTREZ IDs 9219, 57168, 7105, 23475, and 998; the at least three RNA transcripts from the second group comprise or consist of RNA transcripts of the genes represented by or corresponding to ENTREZ IDs 112858, 5326, 23509, 6780, and 1846; the at least three RNA transcripts from the third group comprise or consist of RNA transcripts of the genes represented by or corresponding to ENTREZ IDs 7078, 80150, 84189, 84666, and 5937; and the at least three RNA transcripts from the fourth group comprise or consist of RNA transcripts of the genes represented by or corresponding to ENTREZ IDs 143903, 23414, 11037, 27295, and 165.

In particular embodiments of the method, the step of obtaining an expression level of at least three RNA transcripts may be described as comprising preparing RNA transcripts from a genetic sample of the colorectal cancer tissue sample; and quantifying the expression level of the at least three of the RNA transcripts.

The method may further comprise a step of administering a treatment protocol to the human patient based at least in part on the CMS determination.

The method may even further comprise a step of generating a report indicating one or more of the CMS determination, the CMS of the colorectal cancer, a treatment protocol based at least in part on the CMS determination, and a treatment protocol specific for the CMS of the colorectal cancer. Determining a CMS score may be described as comprising matching the expression level of each RNA transcript with a reference expression level of said RNA transcript in a respective reference data set, each reference expression level corresponding to a scaled value representing the probability that the CMS of a colorectal cancer expressing said RNA transcript at said reference expression level is one of CMS1, CMS2, CMS3, and CMS4; and calculating the CMS score based on the respective scaled values for each of the RNA transcripts.

Calculating the CMS score may be described as comprising calculating a mean of the respective scaled values for each of the RNA transcripts from the respective group of genetic elements. The method, wherein each reference data set comprises a curve fit of a population of the respective RNA transcript, the curve fit reflecting the probability that the CMS of a colorectal cancer expressing said RNA transcript at each reference expression level is one of CMS1, CMS2, CMS3, and CMS4.

In some embodiments, the method provides for a first group of genetic elements that comprises a panel of genes expressed in a population of colorectal cancers having a CMS selected from CMS1, CMS2, CMS3, and CMS4.

The method, wherein the panel comprises or consists of between five and twenty-five genes expressed in a population of colorectal cancers having a CMS selected from CMS1, CMS2, CMS3, and CMS4.

A system comprising: one or more processor(s); and one or more computer-readable hardware storage devices having stored thereon computer-executable instructions that are executable by the one or more processor(s) to cause the computer system to performs one or more of the steps of any preceding claim.

A non-transitory computer-readable storage medium storing instructions that, when executed by one or more processors, performs one or more of the steps of any preceding claim.

A computer system implementing any or all of the described methods is also disclosed, In one embodiment, the computer system comprises: one or more processor(s); and one or more computer-readable hardware storage devices having stored thereon computer-executable instructions that are executable by the one or more processor(s) to cause the computer system to visually display a report by causing the computer system to: identify expression levels of each of at least twelve RNA transcripts from a colorectal cancer tissue sample of unknown consensus molecular subtype (CMS), the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4; determine, based on an expression level of each of at least three RNA transcripts from a first group of the four groups of genetic elements, a first CMS score representative of a probability that the CMS of the colorectal cancer is CMS1, the first group of genetic elements comprising or consisting of at least 3 of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; determine, based on an expression level of each of at least three RNA transcripts from a second group of the four groups of genetic elements, a second CMS score representative of a probability that the CMS of the colorectal cancer is CMS2, the second group of genetic elements comprising or consisting of at least 3 of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; determine, based on an expression level of each of at least three RNA transcripts from a third group of the four groups of genetic elements, a third CMS score representative of a probability that the CMS of the colorectal cancer is CMS3, the third group of genetic elements comprising or consisting of at least 3 of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; determine, based on an expression level of each of at least three RNA transcripts from a fourth group of the four groups of genetic elements, a fourth CMS score representative of a probability that the CMS of the colorectal cancer is CMS4, the fourth group of genetic elements comprising or consisting of at least 3 of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 1, 165, 6695, 1292, 9353, 4131, 8639, 5549, 54796, 147906, and 8828; and generating the report, the report indicating one or more of: the first, second, third, and/or fourth CMS score; the probability that the CMS of the colorectal cancer is CMS1, CMS2, CMS3, and/or CMS4; and a CMS classification or determination for the colorectal cancer; the CMS of the colorectal cancer, a treatment protocol based at least in part on the first, second, third, and/or fourth CMS score, the probability that the CMS of the colorectal cancer is CMS1, CMS2, CMS3, and/or CMS4, the CMS classification or determination, and the CMS of the colorectal cancer, and a treatment protocol specific for the CMS of the colorectal cancer, a treatment protocol specific for the colorectal cancer.

As defined above, the computer system may provide for a report that is visually displayed on a graphical user interface coupled to the computer system.

The computer system, wherein the computer-executable instructions are further executable by the one or more processor(s) to cause the computer system to perform any one or more of the step of any preceding claim.

A composition is also disclosed, comprising a mixture of cDNA molecules corresponding to at least twelve RNA transcripts, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4, the at least twelve RNA transcripts comprising: at least three RNA transcripts from a first group of genetic elements, the first group comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; at least three RNA transcripts from a second group of genetic elements, the second group comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; at least three RNA transcripts from a third group of genetic elements, the third group comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and at least three RNA transcripts from a fourth group of genetic elements, the fourth group comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 1, 165, 6695, 1292, 9353, 4131, 8639, 5549, 54796, 147906, and 8828.

The composition may comprise a mixture of cDNA molecules corresponding to at least twelve RNA transcripts, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4, the at least twelve RNA transcripts comprising: at least three RNA transcripts from a first group of genetic elements, the first group comprising or consisting of the genes represented by or corresponding to ENTREZ IDs 9219, 57168, 7105, 23475, and 998; at least three RNA transcripts from a second group of genetic elements, the second group comprising or consisting of the genes represented by or corresponding to ENTREZ IDs 112858, 5326, 23509, 6780, and 1846; at least three RNA transcripts from a third group of genetic elements, the third group comprising or consisting of the genes represented by or corresponding to ENTREZ IDs 7078, 80150, 84189, 84666, and 5937; and at least three RNA transcripts from a fourth group of genetic elements, the fourth group comprising or consisting of the genes represented by or corresponding to ENTREZ IDs 143903, 23414, 11037, 27295, and 165.

A method of confirming or modifying a cancer treatment protocol for a patient with colon or rectal cancer is presented, wherein the method comprises: determining the consensus molecular subtype (CMS) is CMS1, CMS2, CMS3, CMS4, or mixed subtype of the sample; and (i) recommending or administering treatment with a chemotherapeutic when the colon or rectal cancer is CMS4; or (ii) performing the method of any one of claims 63-88 to determine if the probability of recurrence of the colon or rectal cancer is sufficiently high to recommend or administer treatment with the chemotherapeutic when the colon or rectal cancer is CMS1, CMS2, CMS3, or mixed subtype.

By way of example, the chemotherapeutic may comprise FOLFOX, FOLFIRI, fluorouracil, oxaliplatin, and folinic acid, and is preferably leucovorin calcium; and/or fluorouracil, irinotecan, and folinic acid, preferably leucovorin calcium.

The method may further comprise: recommending or administering treatment with the chemotherapeutic when the probability of recurrence is greater than or equal to a predetermined risk threshold; or recommending or administering an observation protocol when the probability of recurrence is less than a predetermined risk threshold.

In another aspect, a method of confirming or modifying a cancer treatment protocol for a patient with colon or rectal cancer is provided. In some embodiments, the method comprises conducting those steps provided herein to determine if the colon or rectal cancer is of consensus molecular subtype (CMS) is CMS1, CMS2, CMS3, CMS4, or mixed subtype; and recommending or administering treatment with a chemotherapeutic when the colon or rectal cancer is CMS2; or performing the method as described herein for determining if the probability of recurrence of the colon or rectal cancer is sufficiently high to recommend or administer treatment with the chemotherapeutic when the colon or rectal cancer is CMS1, CMS3, CMS4, or mixed subtype. In some embodiments, the chemotherapeutic that may be proposed and/or recommended for treatment comprises cetuximab, a monoclonal antibody that inhibits activity of the gene EGFR, or a combination thereof.

In some embodiments, the method is further described as comprising: recommending or administering treatment with the chemotherapeutic when the probability of recurrence is greater than or equal to a predetermined risk threshold; or recommending or administering an observation protocol when the probability of recurrence is less than a predetermined risk threshold. The predetermined risk threshold is or may comprise a probability of recurrence of the cancer (colon, rectal, etc.) is greater than or equal to about forty-one percent or 0.41 for the colon or rectal cancer. In some embodiments, the colon or rectal cancer is a metastatic colon or rectal cancer.

In yet another aspect, kits are provided for use in performing a diagnostic method, such as a method of predicting or determining a consensus molecular subtype (CMS) of colorectal cancer in a human patient. In some embodiments, the kit comprises a plurality of oligonucleotide primers configured to bind complementarily to respective portions of cDNA of at least twelve RNA transcripts from a colorectal cancer tissue sample and prime polymerase chain reaction of the cDNA, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4. In some embodiments, the oligonucleotide primers are (i) respectively, disposed or contained in a plurality of reaction containers or (ii) bound to a substrate or surface thereof.

In particular aspects, the kit will comprise a plurality of reaction containers, wherein the containers comprise sample tubes or wells of a reaction plate. The reaction plate may optionally comprise a 96- or 384-well plate, wherein respective wells of the reaction plate each contain a respective pair of primers configured to prime a polymerase chain reaction of a cDNA of one of the at least twelve RNA transcripts. The kit may comprise any number of different substrates, for example, a plate, chip, array, grid, or flow cell.

In some embodiments of the kit, the at least twelve RNA transcripts comprise: at least three RNA transcripts from a first group of genetic elements, the first group comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; at least three RNA transcripts from a second group of genetic elements, the second group comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; at least three RNA transcripts from a third group of genetic elements, the third group comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and at least three RNA transcripts from a fourth group of genetic elements, the fourth group comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 1, 165, 6695, 1292, 9353, 4131, 8639, 5549, 54796, 147906, and 8828.

In other embodiments of the kit, the at least twelve RNA transcripts comprise: at least three RNA transcripts from a first group of genetic elements, the first group comprising or consisting of the genes represented by or corresponding to ENTREZ IDs 9219, 57168, 7105, 23475, and 998; at least three RNA transcripts from a second group of genetic elements, the second group comprising or consisting of the genes represented by or corresponding to ENTREZ IDs 112858, 5326, 23509, 6780, and 1846; at least three RNA transcripts from a third group of genetic elements, the third group comprising or consisting of the genes represented by or corresponding to ENTREZ IDs 7078, 80150, 84189, 84666, and 5937; and at least three RNA transcripts from a fourth group of genetic elements, the fourth group comprising or consisting of the genes represented by or corresponding to ENTREZ IDs 143903, 23414, 11037, 27295, and 165.

In another aspect, a kit for use in performing a diagnostic method, preferably a method of predicting or determining a consensus molecular subtype (CMS) of colorectal cancer in a human patient, is provided. By way of example, this kit may comprise a plurality of oligonucleotide primers configured to bind complementarily to respective portions of cDNA of at least twelve RNA transcripts from a colorectal cancer tissue sample and prime polymerase chain reaction of the cDNA. The at least twelve RNA transcripts may be described as comprising: at least three RNA transcripts from a first group of genetic elements, the first group comprising or consisting of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and 10451; at least three RNA transcripts from a second group of genetic elements, the second group comprising or consisting of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and 4212; at least three RNA transcripts from a third group of genetic elements, the third group comprising or consisting of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and 155465; and at least three RNA transcripts from a fourth group of genetic elements, the fourth group comprising or consisting of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 4211, 165, 6695, 1292, 9353, 4131, 8639, 5549, 54796, 147906, and 8828.

In some embodiments, the kit will comprise at least twelve RNA transcripts, the transcripts comprising: at least three RNA transcripts from a first group of genetic elements, the first group comprising or consisting of the genes represented by or corresponding to ENTREZ IDs 9219, 57168, 7105, 23475, and 998; at least three RNA transcripts from a second group of genetic elements, the second group comprising or consisting of the genes represented by or corresponding to ENTREZ IDs 112858, 5326, 23509, 6780, and 1846; at least three RNA transcripts from a third group of genetic elements, the third group comprising or consisting of the genes represented by or corresponding to ENTREZ IDs 7078, 80150, 84189, 84666, and 5937; and at least three RNA transcripts from a fourth group of genetic elements, the fourth group comprising or consisting of the genes represented by or corresponding to ENTREZ IDs 143903, 23414, 11037, 27295, and 165.

The oligonucleotide primers may be disposed or contained in a plurality of reaction containers or (ii) bound to a substrate or surface thereof.

The kit, wherein the plurality of reaction containers comprises sample tubes or wells of a reaction plate, the reaction plate optionally comprising a 96- or 384-well plate, wherein respective wells of the reaction plate each contain a respective pair of primers configured to prime polymerase chain reaction of a cDNA of one of the at least twelve RNA transcripts. The substrate may comprise a plate, chip, array, grid, or flow cell.

A kit for use in performing a diagnostic method, preferably a method of predicting or determining a consensus molecular subtype (CMS) of colorectal cancer in a human patient, is further described. The kit may comprise a plurality of oligonucleotide probes configured to bind complementarily to respective portions of cDNA of at least twelve RNA transcripts from a colorectal cancer tissue sample, the at least twelve RNA transcripts comprising at least three RNA transcripts from each of four groups of genetic elements, each of the four groups of genetic elements defining a CMS gene expression profile specific for a different one of CMS1, CMS2, CMS3, and CMS4. The kit, wherein the oligonucleotide probes are (i) respectively, disposed or contained in a plurality of reaction containers or (ii) bound to a substrate or surface thereof.

Additional aspects, features, advantages, and exemplary embodiments of the present disclosure will be set forth in the description which follows, and in part will be obvious from the description, or may be learned by the practice thereof. Various aspects, features, and advantages may also be realized and obtained by means of the instruments and combinations particularly pointed out in the specification and appended claims. These and other aspects, features, and advantages will become more fully apparent from the following description and appended claims, or may be learned by the practice of the embodiments set forth hereinafter.

DETAILED DESCRIPTION

Figure 1A:
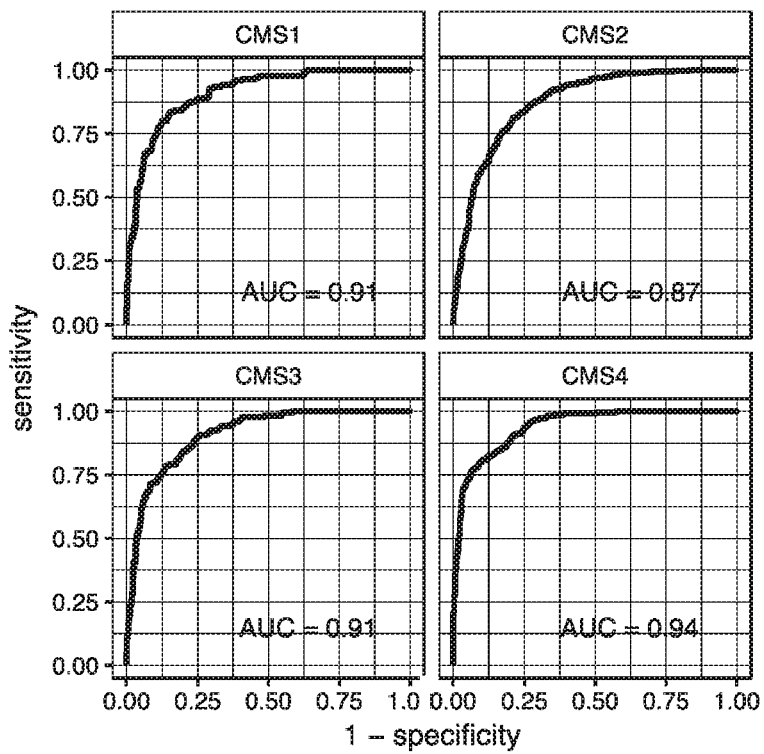
FIGS. 1A-1B illustrate receiver operator characteristic (ROC) curves for (A) Affymetrix validation set, and (B) the COAD validation set, in accordance with an embodiment of the present disclosure.

Before describing various aspects embodiments of the present disclosure in detail, it is to be understood that this disclosure is not limited only to the specific parameters, verbiage, and description of the particularly exemplified systems, methods, and/or products that may vary from one embodiment to the next. Thus, while certain embodiments of the present disclosure will be described in detail, with reference to specific features (e.g., configurations, parameters, properties, steps, components, etc.), the descriptions are illustrative and are not to be construed as limiting the scope of the present disclosure and/or the claimed invention. In addition, the terminology used herein is for the purpose of describing the embodiments and is not necessarily intended to limit the scope of the present disclosure and/or the claimed invention.

While the detailed description is separated into sections, the section headers and contents within each section are for organizational purposes only and are not intended to be self-contained descriptions and embodiments or to limit the scope of the description or the claims. Rather, the contents of each section within the detailed description are intended to be read and understood as a collective whole, where elements of one section may pertain to and/or inform other sections. Accordingly, embodiments specifically disclosed within one section may also relate to and/or serve as additional and/or alternative embodiments in another section having the same and/or similar products, methods, and/or terminology.

To facilitate understanding, like references (i.e., like naming of features, parameters, components and/or elements) may be used, where possible, to designate like elements common to different embodiments of the present disclosure.

For the sake of brevity, the present disclosure may recite a list or range of numerical values. It will be appreciated, however, that where such a list or range of numerical values (e.g., greater than, less than, up to, at least, and/or about a certain value, and/or between two recited values) is disclosed or recited, any specific value or range of values falling within the disclosed values or list or range of values is likewise specifically disclosed and contemplated herein. Abbreviated list of defined terms To assist in understanding the scope and content of the foregoing and forthcoming written description and appended claims, a select few terms are defined directly below.

Unless defined otherwise, all technical and scientific terms used herein have the same meaning as commonly understood by one of ordinary skill in the art to which the present disclosure pertains.

Various aspects of the present disclosure, including systems, methods, and/or products may be illustrated with reference to one or more embodiments, which are exemplary in nature. As used herein, the term "embodiment" means "serving as an example, instance, or illustration," and should not necessarily be construed as preferred or advantageous over other aspects disclosed herein. In addition, reference to an "embodiment" of the present disclosure or invention is intended to provide an illustrative example without limiting the scope of the invention, which is indicated by the appended claims.

As used in this specification and the appended claims, the singular forms "a," "an" and "the" each contemplate, include, and specifically disclose both the singular and plural referents, unless the context clearly dictates otherwise. For example, reference to a "protein" contemplates and specifically discloses one, as well as a plurality of (e.g., two or more, three or more, etc.) proteins. Similarly, use of a plural referent does not necessarily require a plurality of such referents, but contemplates, includes, specifically discloses, and/or provides support for a single, as well as a plurality of such referents, unless the context clearly dictates otherwise.

As used throughout this disclosure, the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, the term "product(s)" includes devices, apparatus, assemblies, systems, and so forth. Similarly, the term "method" includes processes, procedures, steps, and so forth.

As used herein, a "feature" or "aspect" of the present disclosure or embodiment disclosed herein refers to a property, attribute, component, element, member, part, portion, (method) step, or other facet of the subject matter at hand.

The word "or" as used herein generally means any one member of a particular list, but also includes any combination of two or more members of said list. Similarly, the term "and" can be interchangeable with the terms "or," either of which can be understood to mean "and/or".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The terms "plurality" and "at least two" are used interchangeably.

The term "patient," as used herein, is synonymous with the term "subject" and generally refers to any animal under the care of a medical professional, as that term is defined herein, with particular reference to (i) humans (under the care of a doctor, nurse, or medical assistant or volunteer) and (ii) non-human animals, such as non-human mammals (under the care of a veterinarian or other veterinary professional, assistant, or volunteer).

The terms "medical professional" as used herein, generally refers to any individual or entity that is responsible for or participates in providing health care to an animal, including human and non-human animals, such as non-human mammals, with particular emphasis on licensed health care providers or unlicensed providers, such as assistants, technicians, and/or volunteers, particularly those covered under the (blanket) license or insurance of a health care provider. This term may, when contextually appropriate, include an oncologist, a surgeon, a physician's assistant, a nurse, a phlebotomist, a veterinarian, etc.

The term "cancer" refers to an abnormal, typically uncontrolled, growth of cells. A "cancerous cell" as used herein comprises a malignant cell having an abnormal, typically uncontrolled, growth. As such, the term cancer is an umbrella term encompassing a plurality of different distinctive diseases characterized by malignant cells growing in a typically uncontrolled manner.

The term "diagnosis," or diagnosing," and similar terms, as used herein, is not intended to convey or require (in all cases) a certified, regulatory-compliant, medical diagnosis, as required or regulated by the U.S. Food and Drug Administration (FDA) or any other government or non-government entity, organization, or agency. Rather, "diagnosis," or diagnosing," and similar terms, as used herein, relates to providing information that may be indicative of a condition and/or helpful in making a determination related to the condition.

All publications, patents, and patent applications cited herein, whether supra or infra, are hereby incorporated by reference in their entirety to the same extent as if each individual publication, patent, or patent application was specifically and individually indicated to be incorporated by reference.

Certain aspects of the present disclosure may be presented using a discovery-validation paradigm, as outlined in further detail, below. Data used during discovery and validation are typically described separate from methodology leading to the discovery. Discovery and validation of CMS and Risk are each covered in separate sections. Tables of summary characteristics of data and genes comprising the panels, along with figures supporting the results and presented in separate subsequent sections.

Synapse Project 2623706 for all datasets except GSE2109. For GSE2109, the CEL files available on the Synapse archive were normalized using fRMA and batch corrected to the other cohorts using combat.

TABLE 1

|  | Cohort A (Affymetrix) | | Cohort B (COAD) | | Cohort C (PETACC3) | |
| --- | --- | --- | --- | --- | --- | --- |
|  | training (n = 683)* | validation (n = 1205⁺ | training (n = 189) | validation (n = 193) | training (n = 342) | validation (n = 346) |
| assay platform | Affymetrix hgu133plus2 | Affymetrix hgu133plus2 | RNA-seq | RNA-seq | custom array | custom array |
| stage (1/2/3/4/NA) | 61/293/ 241/88/0 | 134/206/164/ 30/612 | 28/65/ 58/15/7 | 29/62/ 48/14/2 | NA | NA |
| median age | 68 | 70 | 67 | 69 | NA | NA |
| msi/mss/NA | 72/402/209 | 86/133/653 | 32/133/8 | 28/123/4 | NA | NA |
| CMS± 1/2/3/ 4/NONE [n (%)] | 117 (17)/281 (41)/ 81 (12)/141 (2'1)/ 63 (9) | 133 (15)/315 (36)/ 121 (14)/200 (23)/ 101 (12) | 28 (16)/60 (35)/ 25 (14)/41 (24)/ 19 (11) | 26 (17)/59 (32)/ 24 (15)/37 (24)/ 18 (12) | 39 (11)/120 (35)/ 36 (11) 72 (21)/ 75 (22) | 39 (11)/121 (35)/ 37 (11) 173 (21)/ 7E (22) |

*Formed from datasets (n): GSE17536 (167), GSE39582 (516).

⁺Formed from datasets (n): GSE13067 (69), GSE13294 (150), GSE14333 (149), GSE2109 (264), GSE23878 (31), GSE35896 (57), GSE37892 (121), KFSYCC (276).

±The CMS classification as reported by CRCSC combining the network and random forest classifiers.

Various aspects and/or embodiments of the present disclosure comprise or relate to an inventive colorectal cancer classifier (system and/or methodology). The classifier can be effective for identifying the CMS subtype of a colorectal cancer, tumor or tissue or indicating a probability (score) of the colorectal cancer, tumor or tissue being of a particular CMS classification. Given a primary colorectal tumor sample, the CMS classifier uses measurements of a manageable number (e.g., between 3 and about 50) of genes (e.g., by measuring mRNA expression thereof) to derive numerical scores, from which the sample's CMS subtype is predicted or inferred. While the full expression profile of hundreds of CMS classification genes (per CMS subtype) was originally derived using microarray data, the relatively few number of genes and the manner in which mRNA measurements are combined to derive a prediction allow for easy translation adaptation to a clinical test.

CMS classifier methodology: Certain embodiments of the present disclosure relate to the initial discovery that a data-processed, 20-gene expression signature, comprised of five genes from each of the four CMS categories, can accurately define CMS subtypes for primary colorectal cancer tumor samples. As discussed in further detail herein, however, the expression level of as few as three CMS-predictive genes (per CMS subtype) can be effective in accurately defining CMS subtypes for colorectal cancer.

Patient cohorts with whole-genome analysis: Various embodiments of the present disclosure were developed and preliminarily validated using genome-wide gene expression data from multiple cohorts. Table 1 presents characteristics of colorectal cancer samples used for the training and validation of CMS classification embodiments of the present disclosure in each of three cohorts. A first cohort; Cohort A (n=1888) includes gene expression data from colorectal cancer samples hybridized to Affymetrix hgu13plus2 arrays obtained from Colorectal Cancer Subtyping Consortium (CRCSC, Synapse Project 2623706, see www(dot)synapse (dot)org/) comprised of the datasets GSE13067, GSE13294, GSE14333, GSE17536, GSE219, GSE23878, GSE35896, GSE37892, GSE39582, KFSYCC. Duplicate samples in the GSE14333 and GSE17536 were eliminated. Gene expression values normalized using fRMA were obtained from the Clinical characteristics and the Colorectal Cancer Subtyping Consortium (CRCSC) consensus molecular subtype classifications for each sample in Cohort A were also obtained from Synapse Project 2623706 and summarized herein. For the purpose of deriving and validating the CMS classifier and/or methodology, Cohort A was partitioned into training (n=683) and validation (n=1205) sets. The training set was defined to be all samples in the datasets GSE17536 and GSE39582.

Raw RNA-sequencing alignments (BAM files) were obtained from Genomic Data Commons (gdc(dot)cancer (dot)gov) for the TCGA colon cancer samples (COAD, n=382) and rectal cancer samples (READ, n=136). While normalized count data (FPKM-UQ) is available for these cohorts from Genomic Data Commons, we chose to compute count data for these cohorts using common analytical methods to facilitate comparison of the inventive classifier/methodology across the cohorts. We aligned the BAM files to the Ensembl version 90 human genome (ensembl(dot) org/index(dot)html) using the Bioconductor package Rsubread. Raw count values were normalized as transcripts per million (TPM) and gene expression values measured as log base 2 of TPM values. Patient-level clinical data and CMS classifications for COAD and READ were obtained from Synapse Project 2623706. Relapse-free survival data for COAD was obtained from Broad GDAC Firehose (gdac (dot)broadinstitute.(dot)org). To support the development of the inventive classifier/methodology, COAD was divided into training (n=189) and validation sets (n=193) balanced for CRCSC CMS subtypes.

Data from Cohort C (n=688), consisting of samples from the PETACC3 clinical trial for which mRNA was hybridized to the Almac custom Affymetrix microarray platform, were obtained from Synapse Project 2623706. The cohort was randomly divided into training (n=342) and validation (n=346) sets balanced for CRCSC CMS subtype.

The CRCSC reports CMS classifications obtained by network analysis, the random forest classifier, and a "CMS-fmal" classification that agrees with the network classification when there is a consensus among the contributing classifiers and agrees with the random forest classifier for non-consensus samples. In the present disclosure, the term "CRCSC CMS subtype" refers to "CMS-fmal" unless otherwise specified.

To train and validate recurrence risk related embodiments of the present disclosure, Cohort D was formed, which included samples from Cohort A for which relapse-free survival data is available. Table 2 presents characteristics of the colon cancer samples used for training and validation of these embodiments of the present disclosure. Included on Table 2 is additional data on Cohort B relevant to evaluation of a prognostic signature.

TABLE 2

| partition | Cohort D | | Cohort B | |
| --- | --- | --- | --- | --- |
| | training (n = 203) | validation (9 = 583) | training (n = 189) | validation (n = 193) |
| assay platform | Affymetrix hgu133plus2 | Affymetrix hgu133plus2 | RNA-seq | RNA-seq |
| dataset (n) | GSE14333 (91), GSE39582 (112) | GSE14333 (28), GSE17536 (138), GSE37892 (121), GSE39522 (396) | COAD (189) | COAD (193) |
| stage (1/2/3/4/NA) | 25/102/70/6/0 | 59/307/262/55/0 | 28/65/58/15/7 | 29/62/48/14/2 |
| T-stage (1/2/3/4/NA) | 2/9/77/17/98 | 9/32/260/85/297 | 6/24/126/16/1 | 4/34/104/13/0 |
| RFS 5-yr event (no/yes) | 152/51 | 494/189 | 129/44 | 128/27 |
| median follow up (months) | 44.4 | 42 | 19 | 26 |

Multistate gene models for classification and prognosis: The genomic scores used in the classification methods were defined using multistate methodology. This method associates the expression values of a gene in a cohort of samples with a vector of numbers termed the gene's risk score, comprised of a number between 0 and 1 for each sample in the cohort. A gene's risk score is derived from the vector of expression values by fitting a gaussian mixture model with resampling. In some cases, the expression values for a gene may give rise to multiple risk scores depending on the complexity of the mixture model fit.

The use of gene risk scores enables predictive scores to be computed using the same algorithm in multiple cohorts in which gene expression was measured with different technologies, as follows. Given cohorts S1 and S2 with similar clinical features and a gene g, consider risk scores r1 and r2 for g in S1 and S2, respectively. To assess the numerical equivalence of r1 and r2, we fit loess smoothing models L1, L2 for r1, r2 with respect to the vectors of risk score quantiles, x1, x2, respectively. Concatenate x1 and x2 to form the vector x and use L1 and L2 to predict curves s1 and s2 over x. In this way, we have extended r1 and r2 to curves s1 and s2 over a common domain. We define r1 and r2 to be equivalent risk scores if a linear fit of s1 to s2 has $R2 \geq 0.90$.

The notion of equivalent risk scores for a gene g was used in two ways in the derivation of classifications. First, in selecting genes and risk scores for inclusion in the protocol, we restricted attention to those for which there are equivalent risk scores in all cohorts considered here (Cohorts A-C). Secondly, after selecting a preferred risk score for a gene g in one cohort, such as the Affymetrix training set, if there were multiple equivalent risk scores for g in a second cohort, such as COAD, we selected the one with maximal R2 value, computed as above.

Statistical methods: All statistical analyses were performed using R (www(dot)r-project(dot)org) and Bioconductor packages (bioconductor(dot)org). The package mclust was used for fitting mixture models, and survival analysis was performed with the survival package. The significance of a Cox proportional hazards (CPH) model was assessed with the P value of the logrank score test. The significance of a multivariate CPH over a CPH using a subset of the variables by applying a Chi-squared test to the differences of log-likelihoods of the two CPH models. The proportional hazard condition was tested with the cox.zph function. The expected survival at a time point for each value of a continuous variable will be estimated from a CPH using the rms package.

In a Cox proportional hazards model, the default hazard ratio represents the increased risk due to an increase of 1 unit in the covariate. For a continuous score (0-100), we reported the hazard ratio in increments of 50 so that the hazard ratio is numerically comparable to a hazard ratio for a discrete binary variable.

The ability of a continuous score to predict membership in a subtype will be assessed visually with the receiver operator characteristic (ROC) curve which plots sensitivity (y-axis) by 1-specificity (x-axis) for all values of the score. The ROC curve is a test of how the probability of membership varies with values of the continuous score. The area under the ROC curve (AUC) gives a numerical measure of a score's predictive significance. The quality of the prediction is better than random if AUC is >0.5 and improves as AUC increases up to 1.

The inventive subtyping methodology defines a discrete classification that predicts the four subtypes of the CRCSC CMS classification. The quality of the prediction was assessed using the overall accuracy, along with the sensitivity, specificity and balanced accuracy (mean of the sensitivity and specificity) for CMS 1-4. These statistics were computed using the confusion Matrix function of the caret package.

Given a CMSpre-score S computed from gene risk scores predictive of a CMS in a cohort of samples, the positive predictive value (PPV) of a value v of S, is the ratio of the number of subtype samples with score $\geq v$ over the total number of samples with score >v in the cohort. From the set PPV values associated with values of S, we used loess smoothing to define a smooth non-decreasing score (0-1), called the CMSscore. In the discrete CMS classifier, S was replaced with the associated CMS score.

CMS pre-score: For each CMS subtype, the inventive classifier/methodology includes or produces a continuous score (0-100), subsequently called a CMS pre-score, that informs membership in the subtype. The genes used to define the scores that inform CMS 1-4 were selected by analysis of candidate genes in the Affymetrix training set and COAD training set. Specifically, for each of CMS 1-4, first—the risk scores of genes were ranked by the level of significance in predicting the subtype in the Affymetrix training set. Table 3a presents the genes from which the CMS1-4 scores were computed. Specifically, Table 3a presents the 100 highest ranked candidate genes for CMS subtype predictive scores for each of CMS 1-4. Then, for each subtype, the 5 highly ranked genes in the table were selected as candidates, which were also highly ranked in COAD training set, as the preferred panel of genes to define the CMS scores.

TABLE 3a

| CMS subtype | ENTREZID | SYMBOL | p-value | Values subtype enriched | Rank | Preferred panel member |
|---|---|---|---|---|---|---|
| CMS1 | 6418 | SET | 2.10E−102 | low | 1 | |
| CMS1 | 9219 | MTA2 | 5.21E−89 | high | 2 | X |
| CMS1 | 10855 | HPSE | 5.32E−83 | high | 3 | |
| CMS1 | 3191 | HNRNPL | 1.11E−75 | high | 4 | |
| CMS1 | 9037 | SEMA5A | 4.44E−75 | low | 5 | |
| CMS1 | 10079 | ATP9A | 7.23E−75 | low | 6 | |
| CMS1 | 83737 | ITCH | 2.23E−74 | low | 7 | |
| CMS1 | 10140 | TOB1 | 2.29E−69 | low | 8 | |
| CMS1 | 8313 | AXIN2 | 2.76E−69 | low | 9 | |
| CMS1 | 54891 | INO80D | 9.88E−69 | low | 10 | |
| CMS1 | 57798 | GATAD1 | 1.15E−68 | low | 11 | |
| CMS1 | 998 | CDC42 | 7.38E 68 | low | 12 | X |
| CMS1 | 7105 | TSPAN6 | 4.42E−66 | low | 13 | X |
| CMS1 | 23475 | QPRT | 8.75E−66 | low | 14 | X |
| CMS1 | 6431 | SRSF6 | 3.37E−64 | high | 15 | |
| CMS1 | 3725 | JUN | 2.07E−61 | low | 16 | |
| CMS1 | 81786 | TRIM7 | 2.19E−61 | high | 17 | |
| CMS1 | 955/1 | SEC22B | 2.70E−61 | low | 18 | |
| CMS1 | 1602 | DACH1 | 3.55E−60 | low | 19 | |
| CMS1 | 57168 | ASPHD2 | 3.86E−60 | high | 20 | X |
| CMS1 | 401474 | SAN1D12 | 6.88E−60 | low | 21 | |
| CMS1 | 139322 | APOOL | 9.43E−60 | low | 22 | |
| CMS1 | 1783 | DYNC1L12 | 2.31E−59 | low | 23 | |
| CMS1 | 29966 | STRN3 | 5.24E−59 | high | 24 | |
| CMS1 | 80183 | RUBCNL | 2.54E−58 | low | 25 | |
| CMS1 | 8019 | BRD3 | 3.38E−57 | low | 26 | |
| CMS1 | 3549 | IHH | 3.78E−56 | low | 27 | |
| CMS1 | 27330 | RPS6KA6 | 6.86E−56 | low | 28 | |
| CMS1 | 10451 | VAV3 | 2.62E−55 | low | 29 | |
| CMS1 | 57211 | ADGRG6 | 1.69E−54 | high | 30 | |
| CMS1 | 81617 | CAB39L | 1.90E−54 | low | 31 | |
| CMS1 | 30811 | HUNK | 3.01E−54 | low | 32 | |
| CMS1 | 92211 | CDHR1 | 1.13E−53 | low | 33 | |
| CMS1 | 29974 | A1CF | 2.00E−53 | low | 34 | |
| CMS1 | 7453 | WARS | 2.05E−53 | high | 35 | |
| CMS1 | 10578 | GNLY | 2.52E−53 | high | 36 | |
| CMS1 | 54749 | EPDR1 | 4.20E−53 | low | 37 | |
| CMS1 | 4925 | NUCB2 | 1.04E−52 | high | 38 | |
| CMS1 | 54866 | PPP1R14D | 1.48E−52 | low | 39 | |
| CMS1 | 330 | BIRC3 | 2.77E−52 | high | 40 | |
| CMS1 | 64710 | NUCKS1 | 5.17E−52 | low | 41 | |
| CMS1 | 10299 | 6-Mar | 7.43E−52 | low | 42 | |
| CMS1 | 3717 | JAK2 | 8.66E−52 | high | 43 | |
| CMS1 | 9547 | CXCL14 | 2.00E−51 | low | 44 | |
| CMS1 | 31 | ACACA | 2.17E−51 | high | 45 | |
| CMS1 | 222171 | PRR15 | 2.33E−51 | low | 46 | |
| CMS1 | 23014 | FBXO21 | 3.27E−51 | low | 47 | |
| CMS1 | 128866 | CHMP4B | 3.97E−51 | low | 48 | |
| CMS1 | 10656 | KHDRBS3 | 6.03E−51 | low | 49 | |
| CMS1 | 23657 | SLC7A11 | 1.15E−50 | high | 50 | |
| CMS1 | 9262 | STK17B | 3.47E−50 | high | 51 | |
| CMS1 | 51056 | LAP3 | 1.21E−49 | high | 52 | |
| CMS1 | 5500 | PPP1CB | 1.56E−49 | low | 53 | |
| CMS1 | 55000 | TUG1 | 1.80E−49 | low | 54 | |
| CMS1 | 5920 | RARRES3 | 4.20E−49 | high | 55 | |
| CMS1 | 22824 | HSPA4L | 1.26E−48 | high | 56 | |
| CMS1 | 11168 | PSIP1 | 1.30E−48 | high | 57 | |
| CMS1 | 9852 | EPM2AIP1 | 6.64E−48 | low | 58 | |
| CMS1 | 54894 | RNF43 | 8.00E−48 | low | 59 | |
| CMS1 | 2935 | GSPT1 | 2.70E−47 | low | 60 | |
| CMS1 | 10160 | FARP1 | 5.66E−47 | low | 61 | |
| CMS1 | 29126 | CD274 | 9.23E−47 | high | 62 | |
| CMS1 | 115362 | GBPS | 1.05E−46 | high | 63 | |
| CMS1 | 387695 | C10orf99 | 1.27E−46 | low | 64 | |
| CMS1 | 5727 | PTCH1 | 3.72E−46 | low | 65 | |
| CMS1 | 219285 | SAMD9L | 4.57E−46 | high | 66 | |

TABLE 3a-continued

| CMS subtype | ENTREZID | SYMBOL | p-value | Values subtype enriched | Rank | Preferred panel member |
|---|---|---|---|---|---|---|
| CMS1 | 2786 | GNG4 | 7.74E−46 | low | 67 | |
| CMS1 | 55661 | DDX27 | 7.97E−46 | low | 68 | |
| CMS1 | 359948 | IRF2BP2 | 8.34E−46 | low | 69 | |
| CMS1 | 259282 | BOD1L1 | 9.20E−46 | high | 70 | |
| CMS1 | 56937 | PMEPA1 | 1.17E−45 | low | 71 | |
| CMS1 | 4155 | MBP | 1.19E−45 | high | 72 | |
| CMS1 | 4152 | MBD1 | 2.60E−45 | high | 73 | |
| CMS1 | 83481 | EPPK1 | 3.89E−45 | high | 74 | |
| CMS1 | 56938 | ARNTL2 | 4.36E−45 | high | 75 | |
| CMS1 | 56829 | ZC3HAV1 | 7.47E−45 | high | 76 | |
| CMS1 | 83992 | CTTNBP2 | 8.91E−45 | low | 77 | |
| CMS1 | 57805 | CCAR2 | 1.21E−44 | high | 78 | |
| CMS1 | 28951 | TRIB2 | 1.57E−44 | high | 79 | |
| CMS1 | 80833 | APOL3 | 2.20E−44 | high | 80 | |
| CMS1 | 57216 | VANGL2 | 6.66E−44 | low | 81 | |
| CMS1 | 79442 | LRRC2 | 6.75E−44 | low | 82 | |
| CMS1 | 85407 | NKD1 | 1.07E−43 | low | 83 | |
| CMS1 | 200958 | MUC20 | 4.14E−43 | low | 84 | |
| CMS1 | 9306 | SOCS6 | 6.86E−43 | high | 85 | |
| CMS1 | 54509 | RHOF | 8.59E−43 | high | 86 | |
| CMS1 | 444 | ASPH | 8.62E−43 | high | 87 | |
| CMS1 | 169981 | SPIN3 | 9.37E−43 | low | 88 | |
| CMS1 | 5229 | PGGT1B | 1.20E−42 | low | 89 | |
| CMS1 | 7020 | TFAP2A | 1.62E−42 | high | 90 | |
| CMS1 | 79758 | DHRS12 | 1.81E−42 | low | 91 | |
| CMS1 | 11274 | USP18 | 3.02E−42 | high | 92 | |
| CMS1 | 80323 | CCDC68 | 3.42E−42 | high | 93 | |
| CMS1 | 55328 | RNLS | 4.31E−42 | low | 94 | |
| CMS1 | 51703 | ACSL5 | 4.99E−42 | low | 95 | |
| CMS1 | 10512 | SEMA3C | 6.47E−42 | low | 96 | |
| CMS1 | 2177 | FANCD2 | 1.18E−41 | high | 97 | |
| CMS1 | 6772 | STAT1 | 1.53E−41 | high | 98 | |
| CMS1 | 10206 | TRIM13 | 1.55E−41 | low | 99 | |
| CMS1 | 388610 | TRNP1 | 2.55E−41 | high | 100 | |
| CMS2 | 5326 | PLAGL2 | 8.13E−84 | high | 1 | X |
| CMS2 | 112858 | TP53RK | 9.89E−71 | high | 2 | X |
| CMS2 | 1057 | CELP | 2.12E−62 | high | 3 | |
| CMS2 | 6780 | STAU1 | 2.60E−62 | high | 4 | X |
| CMS2 | 23509 | POFUT1 | 5.34E−61 | high | 5 | X |
| CMS2 | 51497 | NELFCD | 3.66E−60 | high | 6 | |
| CMS2 | 430 | ASCL2 | 4.23E−60 | high | 7 | |
| CMS2 | 171023 | ASXL1 | 3.47E−59 | high | 8 | |
| CMS2 | 25980 | AAR2 | 2.91E−57 | high | 9 | |
| CMS2 | 23475 | QPRT | 3.96E−57 | high | 10 | |
| CMS2 | 22919 | MAPRE1 | 4.94E−56 | high | 11 | |
| CMS2 | 80183 | RUBCNL | 8.19E−56 | high | 12 | |
| CMS2 | 51526 | OSER1 | 2.76E−55 | high | 13 | |
| CMS2 | 28951 | TRIB2 | 3.57E−55 | low | 14 | |
| CMS2 | 1056 | CEL | 6.26E−55 | high | 15 | |
| CMS2 | 1546 | DUSP4 | 7.71E−54 | low | 16 | X |
| CMS2 | 644 | BLVRA | 9.93E−53 | low | 17 | |
| CMS2 | 9054 | NFS1 | 3.20E−52 | high | 18 | |
| CMS2 | 55661 | DDX27 | 4.90E−52 | high | 19 | |
| CMS2 | 54894 | RNF43 | 1.58E−51 | high | 20 | |
| CMS2 | 58490 | RPRD1B | 2.79E−51 | high | 21 | |
| CMS2 | 4212 | MEIS2 | 5.58E−49 | low | 22 | |
| CMS2 | 128866 | CHMP4B | 9.82E−47 | high | 23 | |
| CMS2 | 140831 | ZSWIM3 | 1.20E−45 | high | 24 | |
| CMS2 | 84647 | PLA2G12B | 1.22E−45 | high | 25 | |
| CMS2 | 23314 | SATB2 | 1.32E−45 | high | 26 | |
| CMS2 | 7105 | TSPAN6 | 2.99E−45 | high | 27 | |
| CMS2 | 54915 | YTHDF1 | 1.90E−44 | high | 28 | |
| CMS2 | 81786 | TRIM7 | 4.00E−44 | low | 29 | |
| CMS2 | 10160 | FARP1 | 4.84E−43 | high | 30 | |
| CMS2 | 55076 | TMEM45A | 7.47E−43 | low | 31 | |
| CMS2 | 6624 | FSCN1 | 7.65E−43 | low | 32 | |
| CMS2 | 8836 | GGH | 2.65E−42 | high | 33 | |
| CMS2 | 7020 | TFAP2A | 7.45E−42 | low | 34 | |
| CMS2 | 5874 | RAB27B | 3.80E−41 | low | 35 | |
| CMS2 | 8942 | KYNU | 4.56E−41 | low | 36 | |
| CMS2 | 51012 | PRELID3B | 7.63E−41 | high | 37 | |
| CMS2 | 11264 | PXMP4 | 8.67E−41 | high | 38 | |
| CMS2 | 387119 | CEP85L | 1.96E−40 | low | 39 | |
| CMS2 | 25984 | KRT23 | 3.78E−40 | high | 40 | |
| CMS2 | 9194 | SLC16A7 | 4.06E−40 | low | 41 | |
| CMS2 | 55107 | ANO1 | 1.67E−39 | low | 42 | |

TABLE 3a-continued

| CMS subtype | ENTREZID | SYMBOL | p-value | Values subtype enriched | Rank | Preferred panel member |
|---|---|---|---|---|---|---|
| CMS2 | 7529 | YWHAB | 4.00E−39 | high | 43 | |
| CMS2 | 4935 | GPR143 | 5.35E−39 | high | 44 | |
| CMS2 | 23305 | ACSL6 | 8.27E−39 | high | 45 | |
| CMS2 | 81572 | PDRG1 | 8.91E−39 | high | 46 | |
| CMS2 | 6556 | SLC11A1 | 1.20E−38 | low | 47 | |
| CMS2 | 128486 | FITM2 | 2.11E−38 | high | 48 | |
| CMS2 | 135228 | CD109 | 2.15E−38 | low | 49 | |
| CMS2 | 284252 | KCTD1 | 2.21E−38 | low | 50 | |
| CMS2 | 10551 | AGR2 | 2.39E−38 | low | 51 | |
| CMS2 | 51654 | CDK5RAP1 | 2.46E−38 | high | 52 | |
| CMS2 | 5321 | PLA2G4A | 3.71E−38 | low | 53 | |
| CMS2 | 10267 | RAMP1 | 5.11E−38 | low | 54 | |
| CMS2 | 1820 | ARID3A | 7.54E−38 | high | 55 | |
| CMS2 | 687 | KLF9 | 9.17E−38 | low | 56 | |
| CMS2 | 10079 | ATP9A | 1.47E−37 | high | 57 | |
| CMS2 | 81704 | DOCK8 | 2.07E−37 | low | 58 | |
| CMS2 | 2786 | GNG4 | 3.10E−37 | high | 59 | |
| CMS2 | 100505592 | GAPLINC | 5.51E−37 | low | 60 | |
| CMS2 | 59272 | ACE2 | 7.42E−37 | high | 61 | |
| CMS2 | 80704 | SLC19A3 | 9.44E−37 | high | 62 | |
| CMS2 | 7089 | TLE2 | 1.16E−36 | high | 63 | |
| CMS2 | 2918 | GRM5 | 3.95E−36 | high | 64 | |
| CMS2 | 100505783 | OSER1-451 | 4.90E−36 | high | 65 | |
| CMS2 | 57148 | RALGAPB | 2.56E−35 | high | 66 | |
| CMS2 | 5509 | PPP1R3D | 3.20E−35 | high | 67 | |
| CMS2 | 5552 | SRGN | 3.67E−35 | low | 68 | |
| CMS2 | 92689 | FAM114A1 | 5.28E−35 | low | 69 | |
| CMS2 | 85407 | NKD1 | 5.55E−35 | high | 70 | |
| CMS2 | 8856 | NR1I2 | 7.14E−35 | high | 71 | |
| CMS2 | 1396 | CRIP1 | 9.70E−35 | low | 72 | |
| CMS2 | 57446 | NDRG3 | 1.09E−34 | high | 73 | |
| CMS2 | 128346 | C1orf162 | 1.24E−34 | low | 74 | |
| CMS2 | 2069 | EREG | 1.33E−34 | high | 75 | |
| CMS2 | 10451 | VAV3 | 1.83E−34 | high | 76 | |
| CMS2 | 4688 | NCF2 | 4.82E−34 | low | 77 | |
| CMS2 | 7850 | IL1R2 | 5.04E−34 | low | 78 | |
| CMS2 | 79442 | LRRC2 | 1.28E−33 | high | 79 | |
| CMS2 | 493869 | GPX8 | 1.52E−33 | low | 80 | |
| CMS2 | 155465 | AGR3 | 1.66E−33 | low | 81 | |
| CMS2 | 643977 | FLJ32255 | 2.22E−33 | low | 82 | |
| CMS2 | 26115 | TANC2 | 2.24E−33 | high | 83 | |
| CMS2 | 10687 | PNMA2 | 3.69E−33 | low | 84 | |
| CMS2 | 79980 | DSN1 | 3.99E−33 | high | 85 | |
| CMS2 | 83658 | DYNLRB1 | 4.12E−33 | high | 86 | |
| CMS2 | 4069 | LYZ | 6.79E−33 | low | 87 | |
| CMS2 | 5203 | PFDN4 | 8.62E−33 | high | 88 | |
| CMS2 | 7130 | TNFAIP6 | 9.65E−33 | low | 89 | |
| CMS2 | 60436 | TGIF2 | 9.99E−33 | high | 90 | |
| CMS2 | 54890 | ALKBH5 | 1.88E−32 | low | 91 | |
| CMS2 | 51507 | RTFDC1 | 1.92E−32 | high | 92 | |
| CMS2 | 2213 | FCGR2B | 3.36E−32 | low | 93 | |
| CMS2 | 6532 | SLC6A4 | 4.80E−32 | high | 94 | |
| CMS2 | 83998 | REG4 | 5.89E−32 | low | 95 | |
| CMS2 | 5948 | RBP2 | 8.04E−32 | high | 96 | |
| CMS2 | 25816 | TNFAIP8 | 1.07E−31 | low | 97 | |
| CMS2 | 9945 | GFPT2 | 1.28E−31 | low | 98 | |
| CMS2 | 3223 | HOXC6 | 1.34E−31 | low | 99 | |
| CMS2 | 5732 | PTGER2 | 1.74E−31 | low | 100 | |
| CMS3 | 4217 | MAP3K5 | 7.60E−52 | high | 1 | |
| CMS3 | 84666 | RETNLB | 1.32E−48 | high | 2 | X |
| CMS3 | 8857 | FCGBP | 6.06E−47 | high | 3 | |
| CMS3 | 7078 | TIMP3 | 9.32E−46 | low | 4 | X |
| CMS3 | 80150 | ASRGL1 | 1.26E−44 | high | 5 | X |
| CMS3 | 4151 | MB | 2.13E−41 | high | 6 | |
| CMS3 | 54596 | L1TD1 | 3.97E−40 | high | 7 | |
| CMS3 | 143458 | LDLRAD3 | 3.11E−39 | low | 8 | |
| CMS3 | 84189 | SLITRK6 | 3.69E−39 | high | 9 | X |
| CMS3 | 7410 | VAV2 | 9.99E−39 | low | 10 | |
| CMS3 | 5937 | RBMS1 | 1.14E−38 | low | 11 | X |
| CMS3 | 25837 | RAB26 | 1.33E−38 | high | 12 | |
| CMS3 | 10753 | CAPN9 | 2.08E−38 | high | 13 | |
| CMS3 | 192134 | B3GNT6 | 3.64E−38 | high | 14 | |
| CMS3 | 201501 | ZBTB7C | 1.26E−35 | high | 15 | |
| CMS3 | 9509 | ADAMTS2 | 1.42E−35 | low | 16 | |
| CMS3 | 140828 | LINC00261 | 1.88E−34 | high | 17 | |
| CMS3 | 84624 | FNDC1 | 2.27E−34 | low | 18 | |

TABLE 3a-continued

| CMS subtype | ENTREZID | SYMBOL | p-value | Values subtype enriched | Rank | Preferred panel member |
|---|---|---|---|---|---|---|
| CMS3 | 1290 | COL5A2 | 2.53E−34 | low | 19 | |
| CMS3 | 405753 | DUOXA2 | 2.20E−33 | high | 20 | |
| CMS3 | 1278 | COL1A2 | 3.15E−33 | low | 21 | |
| CMS3 | 2335 | FN1 | 7.18E−33 | low | 22 | |
| CMS3 | 1295 | COL8A1 | 9.65E−33 | low | 23 | |
| CMS3 | 3488 | IGFBP5 | 1.35E−32 | low | 24 | |
| CMS3 | 9254 | CACNA2D2 | 1.78E−32 | high | 25 | |
| CMS3 | 155465 | AGR3 | 1.92E−32 | high | 26 | |
| CMS3 | 1428 | CRYM | 1.93E−31 | high | 27 | |
| CMS3 | 767 | CA8 | 4.08E−31 | high | 28 | |
| CMS3 | 375056 | MIA3 | 5.00E−31 | high | 29 | |
| CMS3 | 863 | CBFA2T3 | 7.38E−31 | high | 30 | |
| CMS3 | 51655 | RASD1 | 1.18E−30 | high | 31 | |
| CMS3 | 1462 | VCAN | 3.55E−30 | low | 32 | |
| CMS3 | 1306 | COL15A1 | 4.93E−30 | low | 33 | |
| CMS3 | 7058 | THBS2 | 1.33E−29 | low | 34 | |
| CMS3 | 2762 | GMDS | 1.76E−29 | high | 35 | |
| CMS3 | 5732 | PTGER2 | 2.21E−29 | high | 36 | |
| CMS3 | 3624 | INHBA | 2.28E−29 | low | 37 | |
| CMS3 | 10551 | AGR2 | 2.31E−29 | high | 38 | |
| CMS3 | 6678 | SPARC | 2.79E−29 | low | 39 | |
| CMS3 | 1277 | COL1A1 | 4.12E−29 | low | 40 | |
| CMS3 | 4583 | MUC2 | 1.16E−28 | high | 41 | |
| CMS3 | 5265 | SHPINA1 | 1.37E−28 | high | 42 | |
| CMS3 | 83998 | REG4 | 1.37E−28 | high | 43 | |
| CMS3 | 11228 | RASSF8 | 1.40E−28 | low | 44 | |
| CMS3 | 6695 | SPOCK1 | 1.53E−28 | low | 45 | |
| CMS3 | 23213 | SULF1 | 4.65E−28 | low | 46 | |
| CMS3 | 800 | CALD1 | 7.39E−28 | low | 47 | |
| CMS3 | 23158 | TBC1D9 | 1.11E−27 | low | 48 | |
| CMS3 | 4585 | MUC4 | 1.44E−27 | high | 49 | |
| CMS3 | 3373 | HYAL1 | 2.14E−27 | high | 50 | |
| CMS3 | 57535 | KIAA1324 | 2.47E−27 | high | 51 | |
| CMS3 | 474 | ATOH1 | 6.71E−27 | high | 52 | |
| CMS3 | 1051 | CEBPB | 7.06E−27 | low | 53 | |
| CMS3 | 11167 | FSTL1 | 8.28E−27 | low | 54 | |
| CMS3 | 1281 | COL3A1 | 8.68E−27 | low | 55 | |
| CMS3 | 3371 | TNC | 2.01E−26 | low | 56 | |
| CMS3 | 138065 | RNF1S3 | 2.05E−26 | high | 57 | |
| CMS3 | 27290 | SPINK4 | 2.63E−26 | high | 58 | |
| CMS3 | 3092 | HIP1 | 2.70E−26 | low | 59 | |
| CMS3 | 2983 | GUCY1B3 | 6.04E−26 | low | 60 | |
| CMS3 | 2200 | FBN1 | 1.11E−25 | low | 61 | |
| CMS3 | 2619 | GAS1 | 1.45E−25 | low | 62 | |
| CMS3 | 112609 | MRAP2 | 2.62E−25 | high | 63 | |
| CMS3 | 9945 | GFPT2 | 4.39E−25 | low | 64 | |
| CMS3 | 50863 | NTM | 6.59E−25 | low | 65 | |
| CMS3 | 6938 | TCF12 | 7.22E−25 | high | 66 | |
| CMS3 | 283651 | HMGN2P46 | 7.47E−25 | high | 67 | |
| CMS3 | 57221 | ARFGEF3 | 7.71E−25 | high | 68 | |
| CMS3 | 1293 | COL6A3 | 9.51E−25 | low | 69 | |
| CMS3 | 8522 | GAS7 | 1.09E−24 | low | 70 | |
| CMS3 | 9742 | IFT140 | 1.20E−24 | high | 71 | |
| CMS3 | 43849 | KLK12 | 1.54E−24 | high | 72 | |
| CMS3 | 100505501 | LOC100505501 | 2.02E−24 | high | 73 | |
| CMS3 | 8537 | BCAS1 | 3.35E−24 | high | 74 | |
| CMS3 | 9783 | RIMS3 | 3.79E−24 | high | 75 | |
| CMS3 | 59345 | GNB4 | 4.08E−24 | low | 76 | |
| CMS3 | 1373 | CPS1 | 4.74E−24 | high | 77 | |
| CMS3 | 123036 | TC2N | 6.84E−24 | high | 78 | |
| CMS3 | 3671 | ISLR | 6.89E−24 | low | 79 | |
| CMS3 | 8038 | ADAM12 | 7.80E−24 | low | 80 | |
| CMS3 | 23563 | CHSTS | 8.21E−24 | high | 81 | |
| CMS3 | 84662 | GLIS2 | 9.66E−24 | low | 82 | |
| CMS3 | 2069 | EREG | 1.66E−23 | low | 83 | |
| CMS3 | 25803 | SPDEF | 1.96E−23 | high | 84 | |
| CMS3 | 3816 | KLK1 | 2.22E−23 | high | 85 | |
| CMS3 | 11012 | KLK11 | 2.94E−23 | high | 86 | |
| CMS3 | 80055 | PGAP1 | 3.45E−23 | high | 87 | |
| CMS3 | 399959 | MIR100HG | 3.47E−23 | low | 88 | |
| CMS3 | 81849 | ST6GALNAC5 | 3.81E−23 | low | 89 | |
| CMS3 | 6947 | TCN1 | 3.82E−23 | high | 90 | |
| CMS3 | 6926 | TBX3 | 5.30E−23 | high | 91 | |
| CMS3 | 399948 | COLCA1 | 5.37E−23 | high | 92 | |
| CMS3 | 59277 | NTN4 | 8.05E−23 | high | 93 | |
| CMS3 | 94121 | SYTL4 | 8.19E−23 | low | 94 | |

TABLE 3a-continued

| CMS subtype | ENTREZID | SYMBOL | p-value | Values subtype enriched | Rank | Preferred panel member |
|---|---|---|---|---|---|---|
| CMS3 | 2487 | FRZB | 1.11E−22 | high | 95 | |
| CMS3 | 55 | ACPP | 1.73E−22 | high | 96 | |
| CMS3 | 1179 | CLCA1 | 2.10E−22 | high | 97 | |
| CMS3 | 7033 | TFF3 | 3.35E−22 | high | 98 | |
| CMS3 | 80114 | BICC1 | 3.63E−22 | low | 99 | |
| CMS3 | 8828 | NRP2 | 4.18E−22 | low | 100 | |
| CMS4 | 23414 | ZFPM2 | 5.59E−109 | high | 1 | X |
| CMS4 | 30008 | EFEMP2 | 2.25E−103 | high | 2 | |
| CMS4 | 27295 | PDLIM3 | 1.74E−101 | high | 3 | X |
| CMS4 | 2737 | GLI3 | 2.41E−101 | high | 4 | |
| CMS4 | 143903 | LAYN | 4.30E−100 | high | 5 | X |
| CMS4 | 154810 | AMOTL1 | 9.59E−99 | high | 6 | |
| CMS4 | 11037 | STON1 | 6.67E−98 | high | 7 | X |
| CMS4 | 7145 | TNS1 | 2.08E−95 | high | 8 | |
| CMS4 | 9590 | AKAP12 | 7.55E−93 | high | 9 | |
| CMS4 | 5178 | PEG3 | 1.31E−92 | high | 10 | |
| CMS4 | 23194 | FBXL7 | 5.11E−91 | high | 11 | |
| CMS4 | 4256 | MGP | 6.15E−91 | high | 12 | |
| CMS4 | 10000 | AKT3 | 1.01E−90 | high | 13 | |
| CMS4 | 1410 | CRYAB | 4.52E−89 | high | 14 | |
| CMS4 | 862 | RUNX1T1 | 1.91E−88 | high | 15 | |
| CMS4 | 5740 | PTGIS | 2.54E−86 | high | 16 | |
| CMS4 | 4286 | MITF | 4.26E−86 | high | 17 | |
| CMS4 | 83871 | RAB34 | 7.47E−86 | high | 18 | |
| CMS4 | 4211 | MEIS1 | 3.93E−85 | high | 19 | |
| CMS4 | 165 | AEBP1 | 4.62E−85 | high | 20 | X |
| CMS4 | 6695 | SPOCK1 | 5.42E−85 | high | 21 | |
| CMS4 | 1292 | COL6A2 | 6.01E−85 | high | 22 | |
| CMS4 | 9353 | SLIT2 | 8.82E−85 | high | 23 | |
| CMS4 | 4131 | MAP1B | 2.68E−84 | high | 24 | |
| CMS4 | 8639 | AOC3 | 1.07E−83 | high | 25 | |
| CMS4 | 5549 | PRELP | 9.07E−83 | high | 26 | |
| CMS4 | 54796 | BNC2 | 3.81E−82 | high | 27 | |
| CMS4 | 147906 | DACT3 | 5.03E−82 | high | 28 | |
| CMS4 | 8828 | NRP2 | 8.54E−82 | high | 29 | |
| CMS4 | 91653 | BOC | 2.15E−81 | high | 30 | |
| CMS4 | 57616 | TSHZ3 | 2.71E−81 | high | 31 | |
| CMS4 | 144165 | PRICKLE1 | 1.15E−80 | high | 32 | |
| CMS4 | 6383 | SDC2 | 1.29E−79 | high | 33 | |
| CMS4 | 4675 | NAP1L3 | 2.04E−79 | high | 34 | |
| CMS4 | 439921 | MXRA7 | 6.53E−77 | high | 35 | |
| CMS4 | 51309 | ARMCX1 | 2.88E−76 | high | 36 | |
| CMS4 | 7424 | VEGFC | 5.16E−76 | high | 37 | |
| CMS4 | 56967 | C14orf132 | 7.77E−76 | high | 38 | |
| CMS4 | 10082 | GPC6 | 8.65E−75 | high | 39 | |
| CMS4 | 5136 | PDE1A | 1.70E−74 | high | 40 | |
| CMS4 | 151887 | CCDC80 | 2.81E−74 | high | 41 | |
| CMS4 | 25927 | CNRIP1 | 4.91E−74 | high | 42 | |
| CMS4 | 57608 | KIAA1462 | 5.76E−74 | high | 43 | |
| CMS4 | 1346 | COX7A1 | 3.56E−73 | high | 44 | |
| CMS4 | 192668 | CYS1 | 1.99E−72 | high | 45 | |
| CMS4 | 1842 | ECM2 | 2.11E−72 | high | 46 | |
| CMS4 | 1000 | CDH2 | 5.56E−72 | high | 47 | |
| CMS4 | 9902 | MRC2 | 2.28E−71 | high | 48 | |
| CMS4 | 1296 | COL8A2 | 3.18E−71 | high | 49 | |
| CMS4 | 1311 | COMP | 7.33E−71 | high | 50 | |
| CMS4 | 25925 | ZNF521 | 8.15E−71 | high | 51 | |
| CMS4 | 399959 | MIR100HG | 9.16E−71 | high | 52 | |
| CMS4 | 123920 | CMTM3 | 2.03E−70 | high | 53 | |
| CMS4 | 83700 | JAM3 | 2.54E−70 | high | 54 | |
| CMS4 | 50507 | NOX4 | 6.32E−70 | high | 55 | |
| CMS4 | 2121 | EVC | 1.52E−69 | high | 56 | |
| CMS4 | 23111 | SPG20 | 6.10E−69 | high | 57 | |
| CMS4 | 10278 | EFS | 9.58E−69 | high | 58 | |
| CMS4 | 5010 | CLDN11 | 1.82E−68 | high | 59 | |
| CMS4 | 85453 | TSPYL5 | 8.87E−68 | high | 60 | |
| CMS4 | 58494 | JAM2 | 8.93E−68 | high | 61 | |
| CMS4 | 114907 | FBXO32 | 9.99E−68 | high | 62 | |
| CMS4 | 8434 | RECK | 1.05E−67 | high | 63 | |
| CMS4 | 25802 | LMOD1 | 2.20E−67 | high | 64 | |
| CMS4 | 57198 | ATP8B2 | 2.29E−67 | high | 65 | |
| CMS4 | 128553 | TSHZ2 | 2.70E−67 | high | 66 | |
| CMS4 | 83604 | TMEM47 | 3.20E−67 | high | 67 | |
| CMS4 | 1687 | DFNA5 | 3.25E−67 | high | 68 | |
| CMS4 | 401097 | C3orf80 | 1.07E−66 | high | 69 | |
| CMS4 | 1281 | COL3A1 | 5.87E−66 | high | 70 | |

TABLE 3a-continued

| CMS subtype | ENTREZID | SYMBOL | p-value | Values subtype enriched | Rank | Preferred panel member |
|---|---|---|---|---|---|---|
| CMS4 | 9945 | GFPT2 | 6.77E−66 | high | 71 | |
| CMS4 | 26353 | HSPB8 | 6.95E−66 | high | 72 | |
| CMS4 | 10979 | FERMT2 | 8.30E−66 | high | 73 | |
| CMS4 | 79745 | CLIP4 | 1.49E−65 | high | 74 | |
| CMS4 | 27303 | RBMS3 | 3.89E−65 | high | 75 | |
| CMS4 | 284119 | CAVIN1 | 4.67E−65 | high | 76 | |
| CMS4 | 25959 | KANK2 | 1.02E−64 | high | 77 | |
| CMS4 | 1009 | CDH11 | 1.11E−64 | high | 78 | |
| CMS4 | 5350 | PLN | 1.18E−64 | high | 79 | |
| CMS4 | 11117 | EMILIN1 | 4.41E−64 | high | 80 | |
| CMS4 | 84168 | ANTXR1 | 2.15E−63 | high | 81 | |
| CMS4 | 7077 | TIMP2 | 2.41E−63 | high | 82 | |
| CMS4 | 79827 | CLMP | 2.73E−63 | high | 83 | |
| CMS4 | 5587 | PRKD1 | 3.72E−63 | high | 84 | |
| CMS4 | 1264 | CNN1 | 6.28E−63 | high | 85 | |
| CMS4 | 1545 | CYP1B1 | 1.02E−62 | high | 86 | |
| CMS4 | 83872 | HMCN1 | 1.38E−62 | high | 87 | |
| CMS4 | 166336 | PRICKLE2 | 2.12E−62 | high | 88 | |
| CMS4 | 7060 | THBS4 | 3.04E−62 | high | 89 | |
| CMS4 | 23704 | KCNE4 | 5.09E−62 | high | 90 | |
| CMS4 | 1136 | CHRNA3 | 5.10E−62 | high | 91 | |
| CMS4 | 8910 | SGCE | 5.48E−62 | high | 92 | |
| CMS4 | 7345 | UCHL1 | 1.95E−61 | high | 93 | |
| CMS4 | 253827 | MSRB3 | 3.36E−61 | high | 94 | |
| CMS4 | 8483 | CILP | 4.92E−61 | high | 95 | |
| CMS4 | 134111 | UBE2QL1 | 7.20E−61 | high | 96 | |
| CMS4 | 7220 | TRPC1 | 1.02E−60 | high | 97 | |
| CMS4 | 55228 | PNMAL1 | 1.11E−60 | high | 98 | |
| CMS4 | 7043 | TGFB3 | 6.23E−60 | high | 99 | |
| CMS4 | 8572 | PDLIM4 | 6.30E−60 | high | 100 | |

In some embodiments of the present disclosure, a suitable number of genes that are statistically predictive of membership in the CMS1 subtype can be included in a first group of genes (or genetic elements), from which a smaller number of representative genes can be selected for analysis. Based on the gene expression level (e.g., as measured through RNA quantification) of each of the representative genes from the first group of genetic elements, a first CMS score representative of a probability that the CMS of the colorectal cancer is CMS1 can be determined. For example, in at least one embodiment, the 20 highest ranking genes (e.g., by p-value analysis), that are statistically predictive of membership in the CMS1 subtype can be included in the first group of genes. The expression level of 5 of these 20 genes can be determined and used to calculate a first CMS score representative of a probability that the CMS of the colorectal cancer is CMS1.

Alternatively, the 25 highest ranking genes, 30 highest ranking genes, 35 highest ranking genes, 40 highest ranking genes, 45 highest ranking genes, 50 highest ranking genes, 60 highest ranking genes, 70 highest ranking genes, 80 highest ranking genes, and so forth, or the 18 highest ranking genes, 16 highest ranking genes, 15 highest ranking genes, 12 highest ranking genes, 10 highest ranking genes, 8 highest ranking genes, 6 highest ranking genes, 5 highest ranking genes, and so forth, that are statistically predictive of membership in the CMS1 subtype can be included in the first group of genes. In certain embodiments, any suitable number of genes between the 3 highest ranking genes and all 100 genes that are statistically predictive of membership in the CMS1 subtype can be included in the first group of genes.

In some embodiments, using the highest-ranking genes may not be required. For instance, in some embodiments, the first group of genes may include genes that are statistically predictive of membership in CMS1 but are ranked lower than other (higher ranking) genes. In some embodiments, the first group of genes may include (at least) 4, 5, 6, 7, 8, 9, 10, 11, 12, 13, 14, 15, 16, 18, 20, 25, 30, or more genes that are not among the very highest-ranking genes. For instance, in at least one embodiment, one or more of the top 5, 10, 15, 20, 25, or 30 highest-ranking genes may not be included in the first group of genetic elements.

Similarly, any suitable number of representative genes, out of or from the first group of genes, can be selected for analysis. For example, at least 3 genes from the first group of genes can be selected for analysis. The respective expression levels of these 3 representative genes (or the RNA transcripts thereof) can be determined and used to calculate the first CMS score representative of a probability that the CMS of the colorectal cancer is CMS1. Thus, the CMS classifier methodology can include determining, based on the expression level of each of the at least three RNA transcripts from a first group of genetic elements, a first CMS score representative of a probability that the CMS of the colorectal cancer is CMS1.

In some embodiments, at least 4, 5, 6, 7, 8, 9, 10, 11, 12, 13, 14, 15, 20, or 25 genes (or RNA transcripts) from the first group can be measured to calculate the first CMS score. In some embodiments, less than 100, 90, 80, 70, 60, 50, 40, 30, 25, 20, 15, 10, 9, 8, 7, 6, 5, or 4 genes (or RNA transcripts) from the first group can be measured to calculate the first CMS score. In some embodiments, (about) between 3 and 100, between 3 and 80, between 3 and 60, between 3 and 50, between 3 and 25, between 3 and 20, between 3 and 15, between 3 and 10, between 3 and 8, between 3 and 5, between 4 and 80, between 4 and 60, between 4 and 50, between 4 and 25, between 4 and 20, between 4 and 15, between 4 and 10, between 4 and 8, between 4 and 5, between 5 and 80, between 5 and 60, between 5 and 50, between 5 and 25, between 5 and 20, between 5 and 15, between 5 and 10, or between 5 and 8 genes (or RNA transcripts), or any number of genes or range of numbers of genes therebetween, from the first group can be measured to calculate the first CMS score.

In some embodiments, the selected representative genes (or RNA transcripts), or number thereof, can be the top or highest-ranking genes or number of genes (i.e., the most predictive of membership in the CMS1 subtype). In certain embodiments, some of the selected representative genes (or RNA transcripts), or number thereof, can be among the top genes or number of genes predictive of membership in the CMS1 subtype, while others of the selected representative genes (or RNA transcripts), or number thereof, can be less predictive of membership in the CMS1 subtype than other genes (or RNA transcripts) that are not included in the group or set of representative genes (or RNA transcripts). In some embodiments, the selected representative genes (or RNA transcripts), or number thereof, can be still be predictive of membership in the CMS1 subtype, but may be less predictive than genes (or RNA transcripts) that are not included in the set of representative genes (or RNA transcripts).

In similar manner, in some embodiments of the present disclosure, a suitable number of genes that are statistically predictive of membership in the CMS2 subtype can be included in a second group of genetic elements, from which a smaller number of representative genes can be selected for analysis. Based on the gene expression level (e.g., as measured through RNA quantification) of each of the representative genes from the second group of genetic elements, a second CMS score representative of a probability that the CMS of the colorectal cancer is CMS2 can be determined. For example, in at least one embodiment, the 20 highest ranking genes (e.g., by p-value analysis), that are statistically predictive of membership in the CMS2 subtype can be included in the second group of genes. The expression level of 5 of these 20 genes can be determined and used to calculate a second CMS score representative of a probability that the CMS of the colorectal cancer is CMS2. Alternative numbers, ranges, types, and/or rankings of genes (or RNA transcripts) set for, illustratively, with reference to CMS1 are incorporated for CMS2.

Likewise, in some embodiments of the present disclosure, a suitable number of genes that are statistically predictive of membership in the CMS3 subtype can be included in a third group of genetic elements, from which a smaller number of representative genes can be selected for analysis. Based on the gene expression level (e.g., as measured through RNA quantification) of each of the representative genes from the third group of genetic elements, a third CMS score representative of a probability that the CMS of the colorectal cancer is CMS3 can be determined. For example, in at least one embodiment, the 20 highest ranking genes (e.g., by p-value analysis), that are statistically predictive of membership in the CMS3 subtype can be included in the third group of genes. The expression level of 5 of these 20 genes can be determined and used to calculate a third CMS score representative of a probability that the CMS of the colorectal cancer is CMS3. Alternative numbers, ranges, types, and/or rankings of genes (or RNA transcripts) set for, illustratively, with reference to CMS 1 are incorporated for CMS3.

Moreover, in some embodiments of the present disclosure, a suitable number of genes that are statistically predictive of membership in the CMS4 subtype can be included in a fourth group of genetic elements, from which a smaller number of representative genes can be selected for analysis. Based on the gene expression level (e.g., as measured through RNA quantification) of each of the representative genes from the fourth group of genetic elements, a fourth CMS score representative of a probability that the CMS of the colorectal cancer is CMS4 can be determined. For example, in at least one embodiment, the 20 highest ranking genes (e.g., by p-value analysis), that are statistically predictive of membership in the CMS4 subtype can be included in the fourth group of genes. The expression level of 5 of these 20 genes can be determined and used to calculate a fourth CMS score representative of a probability that the CMS of the colorectal cancer is CMS4. Alternative numbers, ranges, types, and/or rankings of genes of genes (or RNA transcripts) set for, illustratively, with reference to CMS1 are incorporated for CMS4.

By comparing the CMS score for CMS1 with the CMS score for CMS2 with the CMS score for CMS3 with the CMS score for CMS4, one can determine which score represents the highest level of predictive confidence for CMS subtyping or classification. This comparison may determine a maximal CMS score. As described in further detail herein, in some embodiments, one or more of the CMS scores can be above a threshold level of predictive confidence for CMS subtyping or classification.

In Table 3a, the number in the p-value column represents the p-value of a statistical test for predictive significance of the gene's risk score in Affymetrix training set. In the values subtype enriched column, "low" means low expression values of gene are more likely to be in the subtype and "high" means high expression values of gene are more likely to be in the subtype. A mark ("X") in the preferred panel member column indicates the genes included in a preferred panel defined by ranking in both Affymetrix training set and COAD training set. Thus, a preferred panel comprises the genes presented in Table 3b.

TABLE 3b

| CMS subtype | ENTREZID | SYMBOL | p-value | Values subtype enriched | Rank | Preferred panel member |
|---|---|---|---|---|---|---|
| CMS1 | 9219 | MTA2 | 5.21E−89 | high | 2 | X |
| CMS1 | 998 | CDC42 | 7.38E−68 | low | 12 | X |
| CMS1 | 7105 | TSPAN6 | 4.42E−66 | low | 13 | X |
| CMS1 | 23475 | QPRT | 8.75E−66 | low | 14 | X |
| CMS1 | 57168 | ASPHD2 | 3.86E−60 | high | 20 | X |
| CMS2 | 5326 | PLAGL2 | 8.13E084 | high | 1 | X |
| CMS2 | 112858 | TP53RK | 9.89E−71 | high | 2 | X |
| CMS2 | 6780 | STAU1 | 2.60E−62 | high | 4 | X |
| CMS2 | 23509 | POFU51 | 5.34E−61 | high | 5 | X |
| CMS2 | 1846 | DUSP4 | 7.71E−54 | low | 16 | X |
| CMS3 | 84666 | RETNLB | 1.32E−48 | high | 2 | X |

TABLE 3b-continued

| CMS subtype | ENTREZID | SYMBOL | p-value | Values subtype enriched | Rank | Preferred panel member |
|---|---|---|---|---|---|---|
| CMS3 | 7078 | TIMP3 | 9.32E−46 | low | 4 | X |
| CMS3 | 80150 | ASRGL1 | 1.26E−44 | high | 5 | X |
| CMS3 | 84189 | SLITRK6 | 3.69E−39 | high | 9 | X |
| CMS3 | 5937 | RBMS1 | 1.14E−38 | low | 11 | X |
| CMS4 | 23414 | ZFPM2 | 5.59E−109 | high | 1 | X |
| CMS4 | 27295 | PDLIM3 | 1.74E−101 | high | 3 | X |
| CMS4 | 143903 | LAYN | 4.30E−100 | high | 5 | X |
| CMS4 | 11037 | STON1 | 6.67E−98 | high | 7 | X |
| CMS4 | 165 | AEBP1 | 4.62E−85 | high | 20 | X |

In an alternative embodiment, 20 or more genes can make up each group of genetic elements. Table 3c, for example, includes 29 of the predictively-significant genes for which the CMS subtype column has the value CMS 1, 22 of the predictively-significant genes for which the CMS subtype column has the value CMS2, 26 of the predictively-significant genes for which the CMS subtype column has the value CMS3, and 29 of the predictively-significant genes for which the CMS subtype column has the value CMS4.

TABLE 3c

| CMS subtype | ENTREZID | Symbol | Rank | Direction |
|---|---|---|---|---|
| CMS1 | 6418 | SET | 1 | − |
| CMS1 | 9219 | M IN2 | 2 | + |
| CMS1 | 10855 | HPSE | 3 | + |
| CMS1 | 3191 | HNRNPL | 4 | − |
| CMS1 | 9037 | SEMA5A | 5 | + |
| CMS1 | 10079 | ATP9A | 6 | + |
| CMS1 | 83737 | ITCH | 7 | + |
| CMS1 | 10140 | TOB1 | 8 | − |
| CMS1 | 8313 | AXIN2 | 9 | + |
| CMS1 | 54891 | INO80D | 10 | − |
| CMS1 | 57798 | GATAD1 | 11 | + |
| CMS1 | 998 | CDC42 | 12 | − |
| CMS1 | 7105 | TSPAN6 | 13 | + |
| CMS1 | 23475 | QPRT | 14 | + |
| CMS1 | 6431 | SRSF6 | 15 | − |
| CMS1 | 3725 | JUN | 16 | + |
| CMS1 | 81786 | TRIM7 | 17 | + |
| CMS1 | 9554 | SEC22B | 18 | − |
| CMS1 | 1602 | DACH1 | 19 | + |
| CMS1 | 57168 | ASPHD2 | 20 | + |
| CMS1 | f | SAMD12 | 21 | + |
| CMS1 | 139322 | APOOL | 22 | + |
| CMS1 | 1783 | DYNC1LI2 | 23 | + |
| CMS1 | 29966 | STRN3 | 24 | + |
| CMS1 | 80183 | RUBCNL | 25 | + |
| CMS1 | 8019 | BRD3 | 26 | + |
| CMS1 | 3549 | IHH | 27 | + |
| CMS1 | 27330 | RPS6KA6 | 28 | + |
| CMS1 | 10451 | VAV3 | 29 | + |
| CMS2 | 5326 | PLAGL2 | 1 | + |
| CMS2 | 112858 | TP53RK | 2 | + |
| CMS2 | 1057 | CELP | 3 | + |
| CMS2 | 6780 | STAU1 | 4 | + |
| CMS2 | 23509 | POFUT1 | 5 | + |
| CMS2 | 51497 | NELFCD | 6 | + |
| CMS2 | 430 | ASCL2 | 7 | + |
| CMS2 | 171023 | ASXL1 | 8 | + |
| CMS2 | 25980 | AAR2 | 9 | + |
| CMS2 | 23475 | QPRT | 10 | + |
| CMS2 | 22919 | MAPRE1 | 11 | + |
| CMS2 | 80183 | RUBCNL | 12 | + |
| CMS2 | 51526 | OSER1 | 13 | + |
| CMS2 | 28951 | TRIB2 | 14 | + |
| CMS2 | 1056 | CEL | 15 | + |
| CMS2 | 1846 | DUSP4 | 16 | + |
| CMS2 | 644 | BLVRA | 17 | + |
| CMS2 | 9054 | NFS1 | 18 | + |

TABLE 3c-continued

| CMS subtype | ENTREZID | Symbol | Rank | Direction |
|---|---|---|---|---|
| CMS2 | 55661 | DDX27 | 19 | + |
| CMS2 | 54894 | RNF43 | 20 | + |
| CMS2 | 58490 | RPRD1B | 21 | + |
| CMS2 | 4212 | MEIS2 | 22 | + |
| CMS3 | 4217 | MAP3K5 | 1 | + |
| CMS3 | 84666 | RETNLB | 2 | + |
| CMS3 | 8857 | FCGBP | 3 | + |
| CMS3 | 7078 | TIMP3 | 4 | + |
| CMS3 | 80150 | ASRGL1 | 5 | + |
| CMS3 | 4151 | MB | 6 | + |
| CMS3 | 54596 | L1TD1 | 7 | + |
| CMS3 | 143458 | LDLRAD3 | 8 | + |
| CMS3 | 84189 | SLITRKE | 9 | + |
| CMS3 | 7410 | VAV2 | 10 | + |
| CMS3 | 5937 | RBMS1 | 11 | + |
| CMS3 | 25837 | RAB26 | 12 | + |
| CMS3 | 10753 | CAPN9 | 13 | + |
| CMS3 | 192134 | B3GNT6 | 14 | + |
| CMS3 | 201501 | ZBTB7C | 15 | + |
| CMS3 | 9509 | ADAMTS2 | 16 | + |
| CMS3 | 140828 | LINC00261 | 17 | + |
| CMS3 | 84624 | FNDC1 | 18 | + |
| CMS3 | 1290 | COL5A2 | 19 | + |
| CMS3 | 405753 | DUOXA2 | 20 | + |
| CMS3 | 1278 | COL1A2 | 21 | + |
| CMS3 | 2335 | FN1 | 22 | + |
| CMS3 | 1295 | COL8A1 | 23 | + |
| CMS3 | 3488 | IGFBP5 | 24 | + |
| CMS3 | 9254 | CACNA2D2 | 25 | + |
| CMS3 | 155465 | AGR3 | 26 | + |
| CMS4 | 23414 | ZFPM2 | 1 | + |
| CMS4 | 30008 | EFEMP2 | 2 | + |
| CMS4 | 27295 | PDLIM3 | 3 | + |
| CMS4 | 2737 | GLI3 | 4 | + |
| CMS4 | 143903 | LAYN | 5 | + |
| CMS4 | 154810 | AMOTL1 | 6 | + |
| CMS4 | 11037 | STON1 | 7 | + |
| CMS4 | 7145 | TNS1 | 8 | + |
| CMS4 | 9590 | AKAP12 | 9 | + |
| CMS4 | 5178 | PEG3 | 10 | + |
| CMS4 | 23194 | FBXL7 | 11 | + |
| CMS4 | 4256 | MGP | 12 | + |
| CMS4 | 10000 | AKT3 | 13 | + |
| CMS4 | 1410 | CRYAB | 14 | + |
| CMS4 | 862 | RUNX1T1 | 15 | + |
| CMS4 | 5740 | PTGIS | 16 | + |
| CMS4 | 4286 | MITF | 17 | + |
| CMS4 | 83871 | RAB34 | 18 | + |
| CMS4 | 4211 | MEIS1 | 19 | + |
| CMS4 | 165 | AEBP1 | 20 | + |
| CMS4 | 6695 | SPOCK1 | 21 | + |
| CMS4 | 1292 | COL6A2 | 22 | + |
| CMS4 | 9353 | SLIT2 | 23 | + |
| CMS4 | 4131 | MAP1B | 24 | + |
| CMS4 | 8639 | AOC3 | 25 | + |
| CMS4 | 5549 | PRELP | 26 | + |
| CMS4 | 54796 | BNC2 | 27 | + |

TABLE 3c-continued

| CMS subtype | ENTREZID | Symbol | Rank | Direction |
|---|---|---|---|---|
| CMS4 | 147906 | DACT3 | 28 | + |
| CMS4 | 8828 | NRP2 | 29 | + | direction is "+" if increasing expressing predicts membership, it is otherwise.

Alternatively, a preferred panel can comprise the genes representing the top 3, 4, 5, 6, 7, 8, 9, 10, 11, 12, 13, 14, 15, 16, 17, 18, 19, 20, 21, 22, 23, 24, or 25 (or more) predictive genes in each CMS.

A CMS1 score can be derived by computing the mean of the gene risk scores of a distinguished set of gene risk scores from among the candidate genes from each group. In certain embodiments, the expression of any 3, 4, 5, 6, or more genes may be used to determine a CMS1 score that gives a statistically significant prediction. To select a preferred panel of genes, one may compare the fits of gene risk scores in the CMS-training data, TCGA-COAD and PETACC-3, giving preference to the genes in which the proportions of samples with gene risk scores above 0.5 are the closest. Restricting to the preferred candidates, one may compute a CMS1 score, for example, for increasing numbers of genes.

In at least one embodiment, inclusion of more than 5 genes from any predictive group of genes may not add further to (or enhance) the predictive nature of the CMS score calculated therefrom. In an illustrative embodiment, a CMS1 score derived from the 5 preferred genes in Table 3d can result in an optimal score for prediction of CMS1, a CMS2 score derived from the 5 preferred genes in Table 3d can result in an optimal score for prediction of CMS2, a CMS3 score derived from the 5 preferred genes in Table 3d can result in an optimal score for prediction of CMS3, and a CMS4 score derived from the 5 preferred genes in Table 3d can result in an optimal score for prediction of CMS4.

TABLE 3d

| CMS subtype | ENTREZID | symbol | rank | direction |
|---|---|---|---|---|
| CMS1 | 9219 | MTA2 | 1 | + |
| CMS1 | 57168 | ASPHD2 | 2 | + |
| CMS1 | 7105 | TSPAN6 | 3 | − |
| CMS1 | 23475 | QPRT | 4 | − |
| CMS1 | 998 | CDC42 | 5 | − |
| CMS2 | 112858 | TP53RK | 1 | + |
| CMS2 | 5326 | PLAGL2 | 2 | + |
| CMS2 | 23509 | POFUT1 | 3 | + |
| CMS2 | 6780 | STAU1 | 4 | + |
| CMS2 | 1846 | DUSP4 | 5 | − |
| CMS3 | 7078 | TIMP3 | 1 | − |
| CMS3 | 80150 | ASRGL1 | 2 | + |
| CMS3 | 84189 | SLITRK6 | 3 | + |
| CMS3 | 84666 | RETNLB | 4 | + |
| CMS3 | 5937 | RBMS1 | 5 | − |
| CMS4 | 143903 | LAYN | 1 | + |
| CMS4 | 23414 | ZFPM2 | 2 | + |
| CMS4 | 11037 | STON1 | 3 | + |
| CMS4 | 27295 | PDLIM3 | 4 | + |
| CMS4 | 165 | AEBP1 | 5 | + |

As outlined above, candidate genes were assessed in both the Affymetrix training set and the COAD training set to avoid biasing the selection to a single training set or assay technology. After extending the risk scores from Affymetrix training set to Affymetrix validation set and the COAD training set to COAD validation set, as described herein, the CMS scores were defined for the entire Affymetrix and COAD data sets. The following method of derivation provides a more detailed disclosure of the CMS determination process:

1. Let X denote the set of all risk scores in Cohort A training set for all Affymetrix hgu133plus2 probes that are annotated to an Entrez ID, and have an equivalent risk score in the COAD training set.
2. Rank order the risk scores in X by the p-value of a linear model having response variable the risk score and covariate an indicator for CMS1.
3. Let Y be the top 25 ranked risk scores in X.
4. Let Z be the risk scores in the COAD training set that are equivalent to the scores in Y, and rank these by linear dependence with CMS 1 membership in the COAD training set.
5. Re-order both Y and Z by the means of the rankings from the two training sets.
6. Form a candidate multigene score, S5, as the mean of the 5 highest ranked multistate scores for each sample in the Affymetrix and COAD training sets.
7. Define S7, S10 and S12 using the top ranked 7, 10 or 12 genes.
8. Using the scores as predictors of membership in CMS1, the AUC values for S5, S7, S10, S12 are 0.955, 0.955, 0.960, 0.955 in the Affymetrix training set, and 0.868, 0.873, 0.877, 0.870 in the COAD training set.
9. Given that the values of S5 are near the maxima for both training sets, this 5-gene score will be selected as CMS1 pre-score.

The above method of derivation was repeated for CMS2-4. For each subset, the 5-gene score was found to be optimal.

Data Processing for Classification into Subtypes Using the CMS Scores

Illustratively, a sample will be classified into that subtype whose score predicts subtype membership with the highest probability. Based on this assumption, in the algorithm we addressed the issues (1) for none of the subtypes is the score high enough to justify classification to that subtype, and (2) two or more scores predict subtype membership with high probability. Probabilities for subtype membership, and possible thresholds were defined using the Affymetrix training set. From among these candidates, we selected the classification algorithm that yielded the maximal mean balanced accuracy for all CMS subtypes in the Affymetrix and COAD training sets, and successfully classified at least 80% of samples. Balanced accuracies were only computed for samples classified into CMS 1-4 by both the inventive system and the CRCSC system.

For each CMS subtype pre-score, compute the subtype's CMS score in the Affymetrix training set using the CRCSC CMS subtypes. The CMS score value for a sample x in the COAD cohort and the validation sets was defined by identifying the sample y in the Affymetrix training set whose subtype pre-score is closest to that of x, and assigning to x the CMS score value of y.

Candidates for a baseline threshold of a CMS score, for example the CMS1 score, under which we would not classify a sample into CMS1, were selected as follows. Let m be the number of samples in the CRCSC CMS1 subtype in the Affymetrix training set. For a number e >1, let be be the value of the CMS1 score so that e*m samples in the Affymetrix training set have CMS1 score >be. In the classification algorithm, a sample will not be classified into CMS1 if the CMS1 score is <be. As candidates for baseline thresholds, identify be values for e=1.10, 1.15, 1.20, 1.25, 1.30, for each CMS subtype.

For the subtype CMS scores and candidate baseline thresholds described above, we evaluated possible CMS classification protocol (or decision tree classifiers protocol) using the mean balanced accuracies in predicting the CRCSC CMS subtypes for all subtypes in both the Affymetrix and COAD training sets. In selecting between classifiers with similar mean balanced accuracies we gave priority to one with a greater percentage of classified samples. The choice of baseline threshold of the classifier with maximal mean balanced accuracy was e=1.25. The steps defining a preferred CMS classification protocol (classifier) is as follows, in order:

1. Given a sample x in the cohort, compute the subtype PPV-score values for x, for all CMS subtypes;
2. If none of the CMS score values of x are greater than the (respective) baseline threshold, then x is classified as mixed subtype (or unclassified subtype);
3. If for only one of the CMS scores is the value of x above the (respective) baseline threshold, then classify x into the subtype for that CMS score;
4. If the CMS scores of x for both CMS2 and CMS4 are above the (respective) baseline thresholds and the CMS score of x for CMS1 is below the (respective) baseline threshold, classify x into CMS4;
5. If the CMS scores of x for both CMS1 and CMS4 are above the (respective) baseline thresholds, classify x into CMS1;
6. If none of 1-5 apply, then classify x into the subtype whose CMS score is maximal.

Thus, if the CMS score of x for CMS1 is the highest score above its threshold (i.e., above its baseline threshold and is maximal), x is always classified into CMS1, regardless of the CMS scores of x for any other CMS2-4. On the contrary, if the CMS score of x for CMS2 is the highest score above its threshold, x is not necessarily CMS2—because if, for example, the CMS score of x for CMS4 is also above its threshold (and the CMS score of x for CMS1 is below its threshold), x is classified as CMS4 even though the CMS score of x for CMS4 is below the CMS score of x for CMS2. However, just because the CMS score of x for CMS1 is above its threshold does not mean that x is automatically classified as CMS1. If, for example, the respective the CMS scores of x for CMS2 and/or CMS3 are above their thresholds and above the CMS score of x for CMS 1 (and the CMS score of x for CMS4 is below its threshold), x would be classified with the higher of CMS2 and CMS3. But, if the CMS score of x for CMS4 is also above its threshold, x is instead classified as CMS1, even though it is not the highest score.

Accordingly, certain embodiments of the present disclosure can include a step (or process) of applying a CMS classification protocol to determine the CMS of a colorectal cancer based on a plurality of CMS scores (e.g., subtype CMS score values for the colorectal cancer, for all four CMS subtypes), as follows:

(ix) classifying the colorectal cancer with a CMS determination of CMS1 when the first CMS score (for CMS1) and the fourth CMS score (for CMS4) are each above respective predictive thresholds;
(x) classifying the colorectal cancer with a CMS determination of CMS4 when the second CMS score (for CMS2) and the fourth CMS score (for CMS4) are each above respective predictive thresholds and when (i) does not apply;
(xi) selecting from among the first, second, third, and fourth CMS scores (for CMS1, CMS2, CMS3, and CMS4, respectively) a maximal CMS score and classifying the colorectal cancer with a CMS determination selected from the group consisting of CMS1, CMS2, CMS3, and CMS4 based on the maximal CMS score or corresponding to the CMS of the maximal CMS score when the maximal CMS score is above the predictive threshold and when neither (i) nor (ii) applies;
(xii) classifying the colorectal cancer with a CMS determination of mixed subtype or unclassified subtype when the first, second, third, and fourth CMS scores (for CMS1, CMS2, CMS3, and CMS4, respectively) are each below the predictive threshold.

Table 4 presents CMS subtypes predicted by the inventive classifier/methodology compared to the CRCSC CMS subtypes in confusion matrices for the Affymetrix and COAD training sets, including the sensitivity, specificity and balanced accuracies.

TABLE 4

| Classifier | Affymetrix training CRCSC subtypes | | | | | COAD training CRCSC subtypes | | | | |
|---|---|---|---|---|---|---|---|---|---|---|
| Subtype | CMS1 | CMS2 | CMS3 | CMS4 | NONE | CMS1 | CMS2 | CMS3 | CMS4 | NONE |
| CMS1 | 101 | 0 | 6 | 12 | 5 | 24 | 1 | 3 | 6 | 4 |
| CMS2 | 3 | 235 | 9 | 8 | 19 | 1 | 53 | 1 | 1 | 7 |
| CMS3 | 1 | 2 | 59 | 1 | 6 | 1 | 2 | 17 | 0 | 0 |
| CMS4 | 2 | 21 | 1 | 112 | 5 | 2 | 2 | 1 | 37 | 6 |
| NONE | 10 | 23 | 6 | 8 | 28 | 4 | 6 | 4 | 1 | 5 |
| sensitivity* | 0.94 | 0.90 | 0.89 | 0.84 | | 0.86 | 0.91 | 0.77 | 0.84 | |
| specificity* | 0.96 | 0.96 | 0.98 | 0.96 | | 0.92 | 0.97 | 0.98 | 0.95 | |
| balanced accuracy* | 0.95 | 0.93 | 0.94 | 0.89 | | 0.89 | 0.94 | 0.87 | 0.90 | |

Figure 1B:
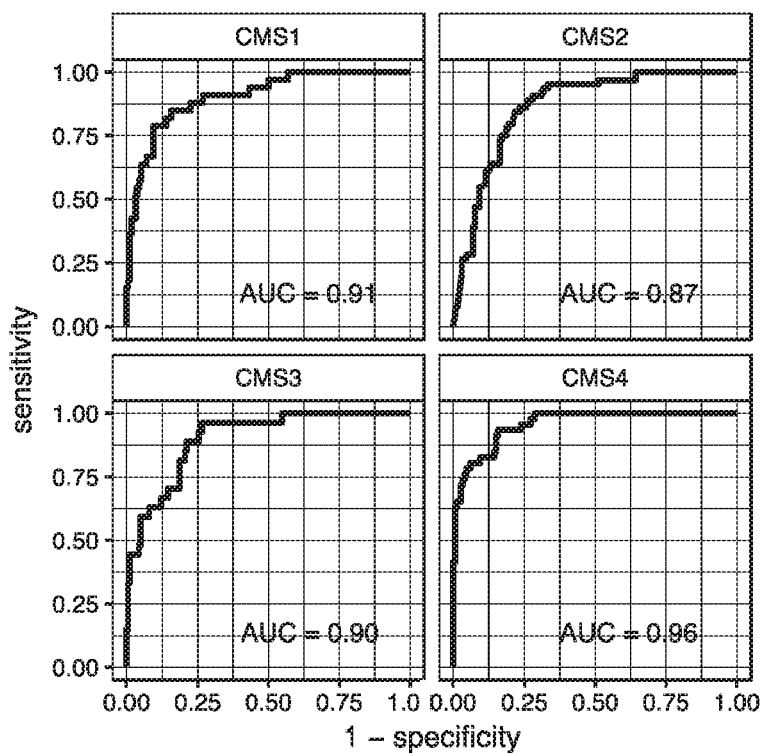
Figure 2A:
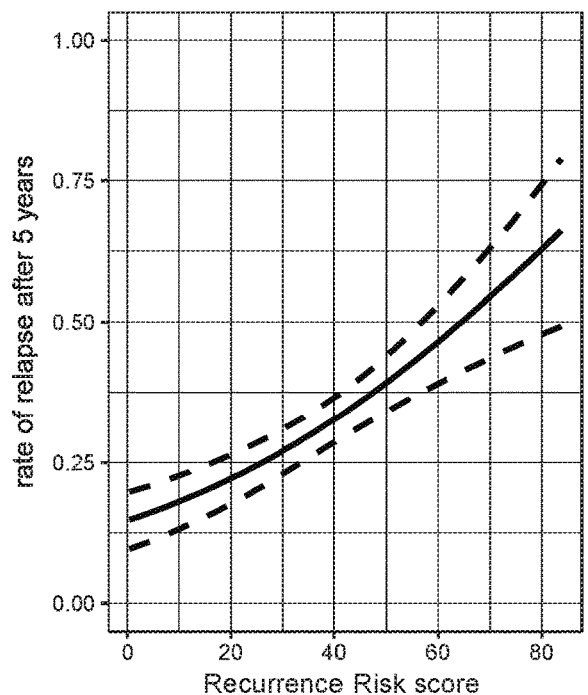
FIGS. 2A-2B illustrate the expected rate of relapse after 5 years for values of the Recurrence Risk score for (A) Cohort D validation set, and (B) Cohort B validation set.
Figure 2B:
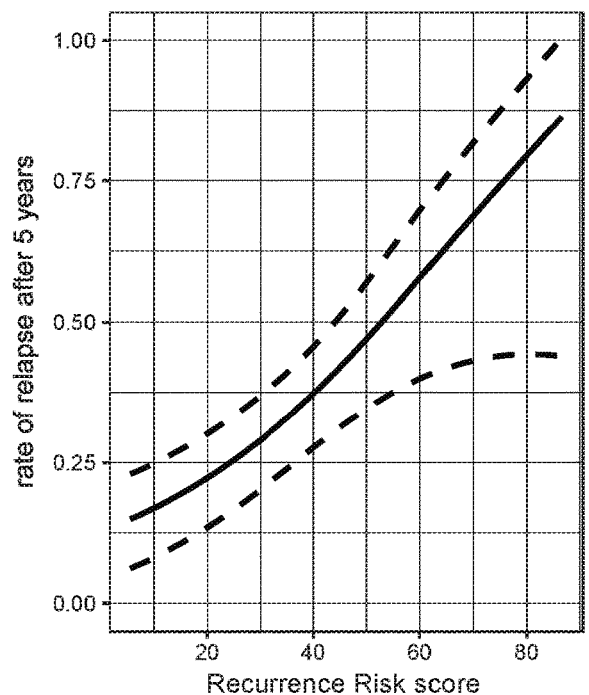
Figure 3A:
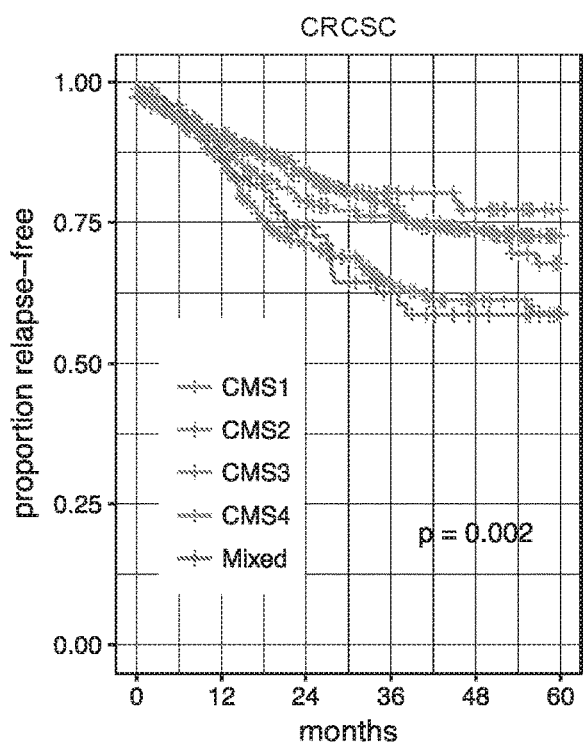
FIGS. 3A-3B illustrate Kaplan-Meier plots in the combined Cohort D and Cohort B validation sets for (A) CRCSC CMS classification, and (B) inventive CMS classification.
Figure 3B:
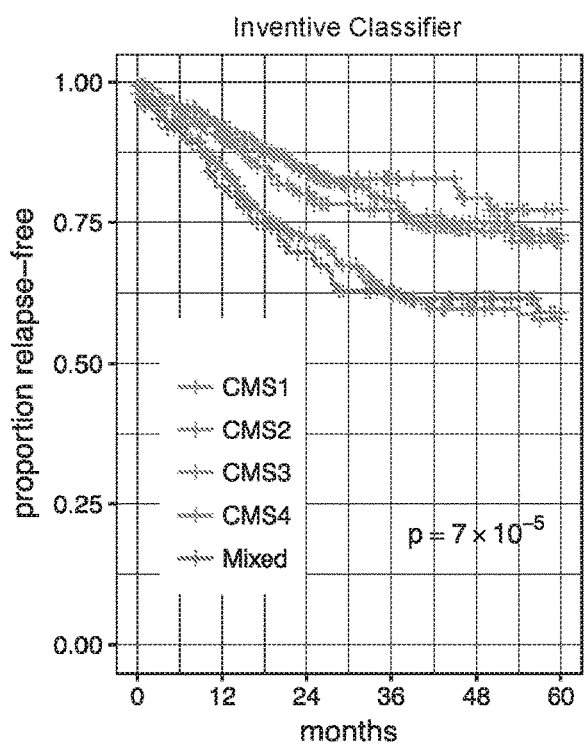
Figure 4:
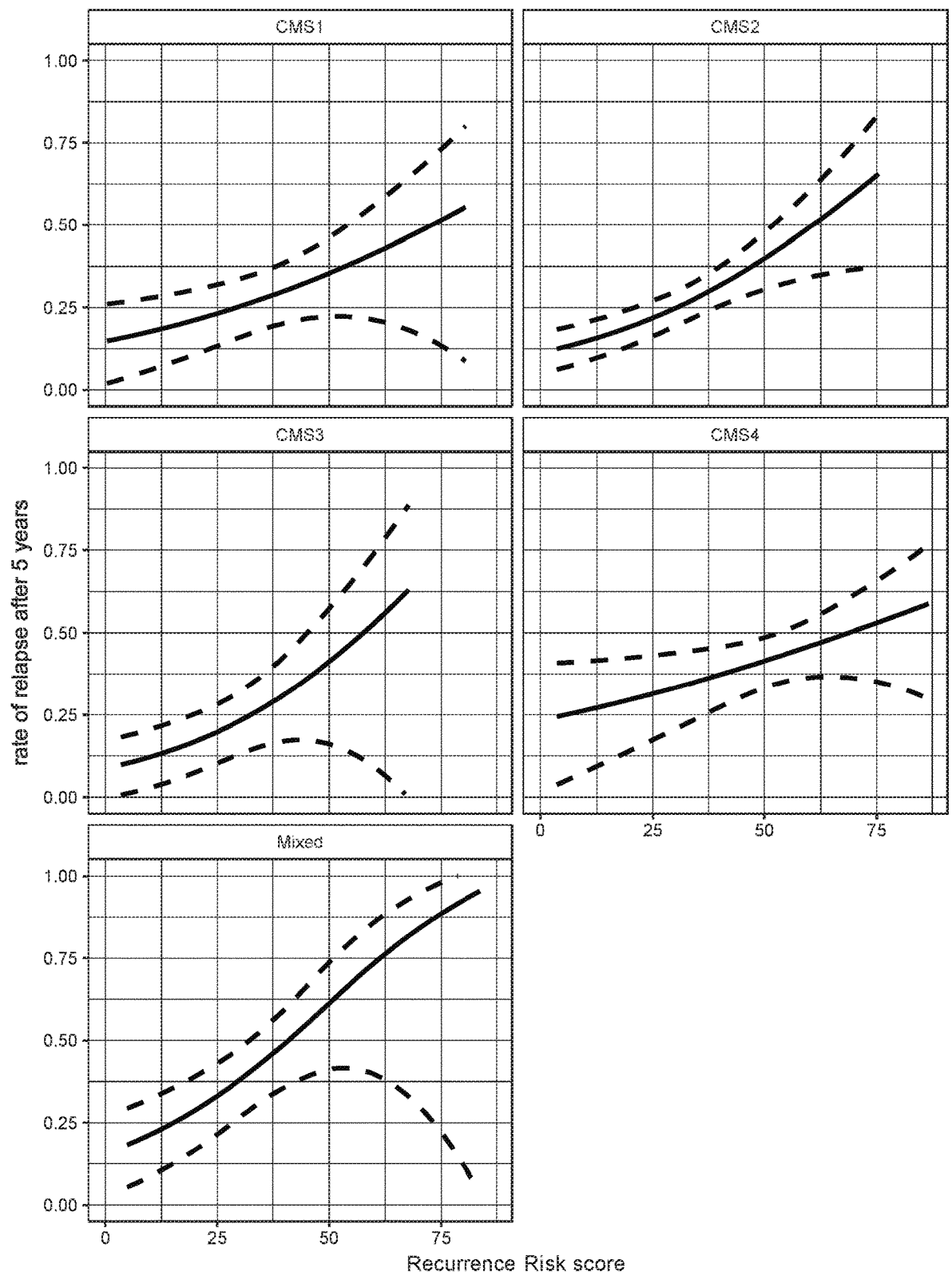
FIG. 4 illustrates the expected rate of relapse after 5 years for values of the Recurrence Risk score for the various inventive CMS subtype classification in the combined Cohort B and Cohort D validation sets (solid line) and 95% confidence intervals (dashed lines).
Figure 5:
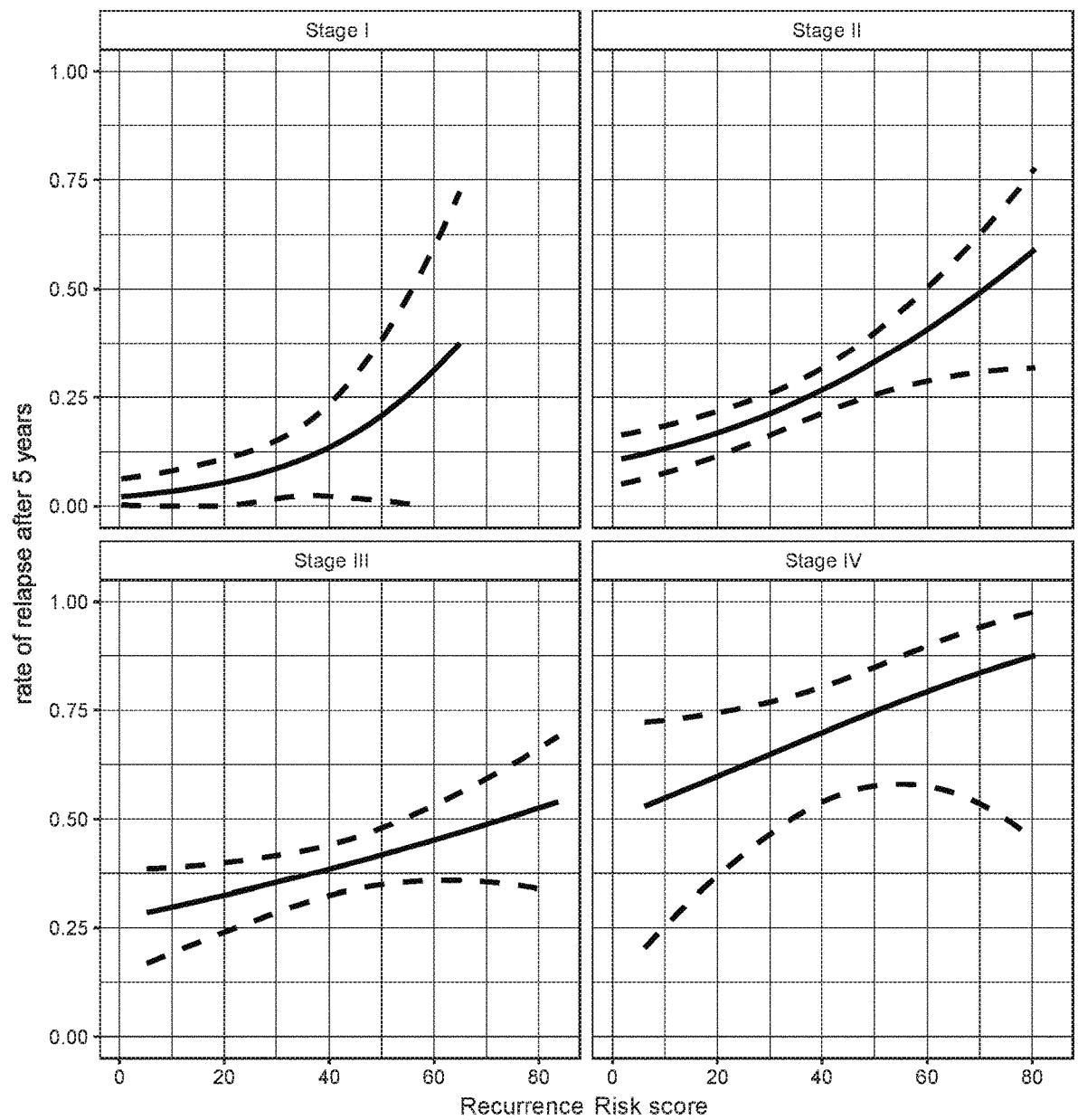
FIG. 5 illustrates the expected rate of relapse after 5 years for values of the Recurrence Risk score for stage I-IV in the combined Cohort B and Cohort D validation sets (solid line) and 95% confidence intervals (dashed lines).
Figure 6A:
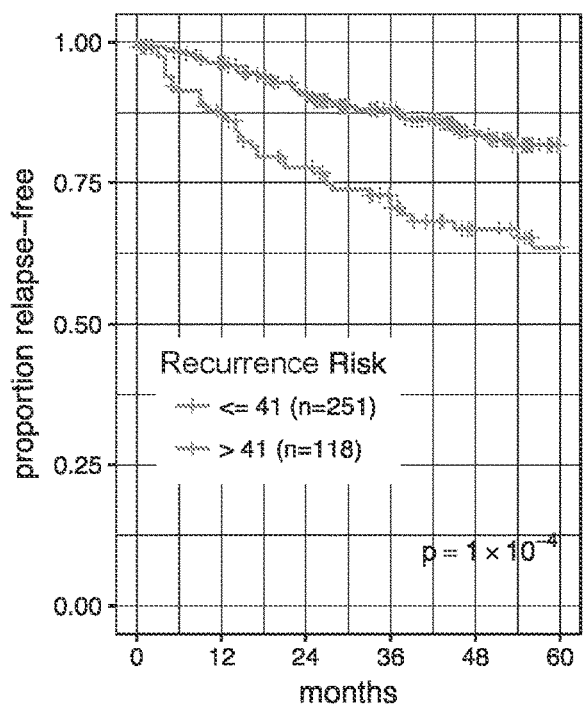
FIGS. 6A-6B illustrate Kaplan-Meier plots in the combined Cohort B and Cohort D validation sets for (A) stage II patients stratified as Recurrence Risk <41 or Recurrence Risk >41, or (B) stage III patients stratified as Recurrence Risk <23 or Recurrence Risk >23.
Figure 6B:
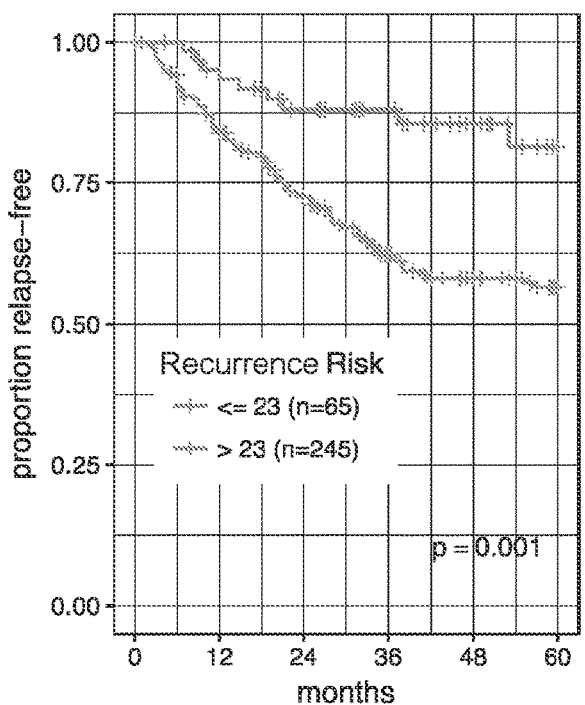
Figure 7A:
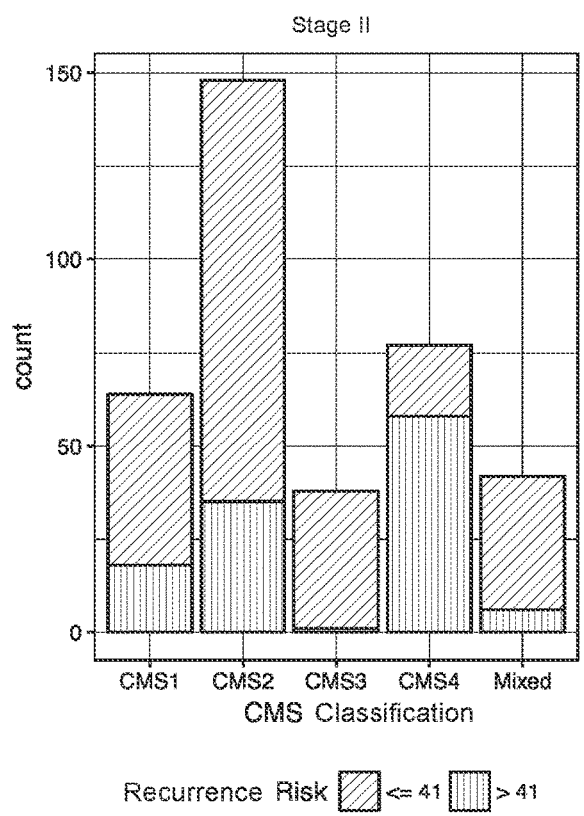
FIGS. 7A-7B illustrate the distribution of risk strata in CMS subtypes in the combined Cohort B and Cohort D validation sets in (A) stage II, and (B) stage III.
Figure 7B:
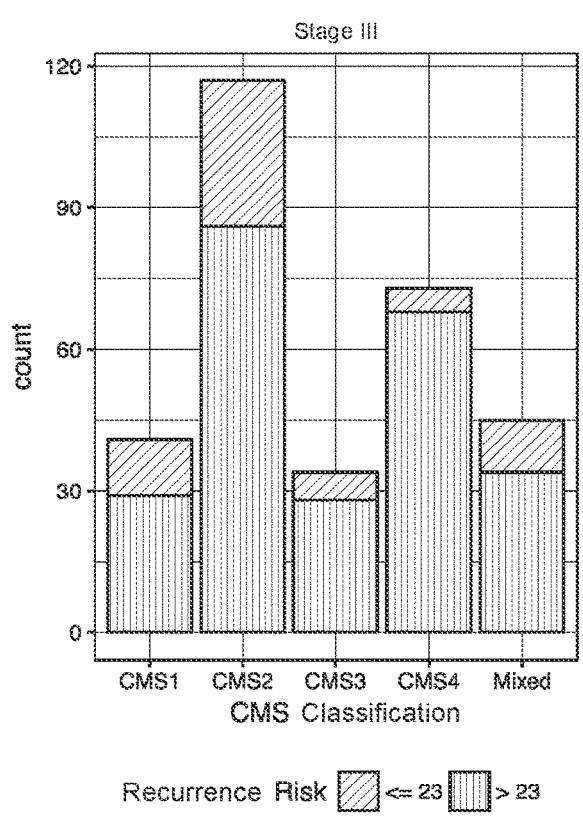

*Samples unclassified by either classifier, labelled NONE, were excluded in calculating these statistics. Validation of CMS classification method in Affymetrix and COAD validation cohorts, and READ The significance of each CMS score defined above was validated as a predictor of CRCSC CMS subtype membership with receiver operator characteristic (ROC) plots and area under the curve (AETC) values in the Affymetrix validation set and COAD validation set. FIGS. 1A-1B illustrate receiver operator characteristic (ROC) curves for (A) the Affymetrix validation set, and (B) the COAD validation set. Each panel plots the ROC curve for predicting membership in the CRCSC CMS subtype with the corresponding inventive CMS score. Area under the curve (AETC) values assess the accuracy of the prediction; values closer to 1 indicate greater accuracy. Because all AETC values were at least 0.87, this was evidence that the CMS scores were strong predictors of CMS subtype membership in these cohorts.

The inventive CMS classifier, defined above, classified 85% and 86% of samples into CMS subtypes in the Affymetrix validation set and COAD validation set, respectively. In comparison, CRCSC classified 89% and 88% into a CMS subtype in these cohorts. Table 5 presents CMS subtypes predicted by the inventive CMS classifier compared to the CRCSC CMS subtypes in confusion matrices for the Affymetrix and COAD validation sets, including the sensitivity, specificity and balanced accuracies. Agreement of the inventive CMS predicted subtypes with CRCSC subtypes exhibited balanced accuracies for CMS1-4 of 0.90. 0.91, 0.91, 0.88 in Affymetrix validation set, and 0.92, 0.94, 0.83, 0.87 in the COAD validation set. The overall prediction of CMS subtype by the inventive CMS classifier was statistically significant in Affymetrix validation set [overall accuracy 0.85 (95% CI 0.83-0.87), no information rate 0.42, p-value $<2.0\times10^{16}$] and COAD validation set [overall accuracy 0.86 (95% CI 0.80-0.91), no information rate 0.38, p-value $<2.0\times10^{16}$].

for Cohort C training set from probe risk scores as for the Affymetrix training set. The CMS scores were then computed for the Cohort C validation set using the Cohort C training set as a reference set.

The AETC values for the CMS scores for CMS 1-4 in the Cohort C validation set were 0.78, 0.83, 0.92, 0.87, respectively. The subsequent classification of samples in CMS subtypes using the scores agreed with CRCSC-CMS subtypes with accuracy 0.81 and balanced accuracies 0.76, 0.88, 0.93, 0.86 for CMS1-4, respectively. This result shows that CMS classifier can be executed using FFPE tissue samples.

CMS classifier/methodology predicts response to cetuximab therapy: Some embodiments include determining and/or administering a treatment protocol based at least in part

TABLE 5

| | Affymetrix validation (n = 1205) CRCSC subtypes | | | | | COAD validation (n = 193) CRCSC subtypes | | | | |
|---|---|---|---|---|---|---|---|---|---|---|
| | CMS1 | CMS2 | CMS3 | CMS4 | NONE | CMS1 | CMS2 | CMS3 | CMS4 | NONE |
| CMS1 | 124 | 9 | 17 | 27 | 20 | 22 | 0 | 2 | 4 | 1 |
| CMS2 | 1 | 329 | 2 | 17 | 21 | 0 | 59 | 4 | 5 | 6 |
| CMS3 | 6 | 20 | 112 | 2 | 22 | 3 | 0 | 13 | 1 | 5 |
| CMS4 | 12 | 22 | 1 | 212 | 27 | 0 | 1 | 0 | 31 | 1 |
| NONE | 27 | 62 | 40 | 25 | 48 | 8 | 4 | 8 | 5 | 10 |
| sensitivity* | 0.87 | 0.87 | 0.85 | 0.82 | | 0.88 | 0.98 | 0.68 | 0.76 | |
| specificity* | 0.93 | 0.96 | 0.96 | 0.95 | | 0.95 | 0.89 | 0.97 | 0.99 | |
| balanced accuracy* | 0.90 | 0.91 | 0.91 | 0.88 | | 0.92 | 0.94 | 0.83 | 0.87 | |

*Samples unclassified by either classifier, labelled NONE, were excluded in calculating these statistics.

The distributions of CRCSC CMS 1-4 subtypes in the READ rectal cancer cohort were 3%, 46%, 13%, 29%, respectively. These differences compared to colon cancer are to be expected because the CMS1 tumors are largely proximal, and CMS2 tumors are largely distal. The CMS classifier scores were computed for the READ rectal cancer cohort using the COAD training set as a reference set of samples, and the inventive CMS classification was computed with the same thresholds as for COAD. The inventive CMS classifier/methodology exhibits significant agreement with CRCSC CMS classification [overall accuracy 0.83 (95% CI 0.75-0.90), no information rate 0.51, p-value=1.4×10 12] and balanced accuracies for CMS1-4, 0.76, 0.85, 0.95, 0.87, respectively.

CMS Classifier/Methodology Predicts CMS in Samples for the PETACC3 Clinical Trial Tissue samples from patients in the PETACC3 clinical trial were stored using formalin-fixed paraffin-embedded (FFPE) methodology. Previously, mRNA was extracted from a set of samples from PETACC3 patients (Cohort C, n=688) and hybridized to an Almac customized Affymetrix microarray platform. To facilitate the translation of the CMS classifier/methodology to this platform, Cohort C was partitioned to a training set (n=342) and validation set (n=346).

Typical of Affymetrix based microarray platforms, many genes are represented by multiple array probes. Thus, executing the CMS classifier algorithm for Cohort C, required selecting, for each of the 20 genes in the preferred CMS classifier panel, a representative probe. To do so, for each CMS classifier panel gene we selected the probe whose risk score in the Cohort C training set was most significantly predictive of the corresponding CRCSC-CMS subtype.

Having selected probes for the CMS classifier panel genes, the CMS scores for each of CMS 1-4 were computed on the CMS classification determined with embodiments of the present disclosure. Illustratively, some embodiments include using the CMS classifier scores to predict differential response to cetuximab among CMS subtypes in colorectal cancer metastases. Specifically, the role of CMS signature scores was assessed in colorectal cancer metastasis samples (GSE5851, n=68, Affymetrix microarray) in predicting response to cetuximab.

Progression-free survival (PFS) was the primary endpoint. The predictive significance of CMS classifier scores relative to KRAS mutation status was also studied using multivariate Cox proportional hazards models.

Cetuximab is a monoclonal antibody that inhibits activity of the gene EGFR. Based on the results of multiple clinical trials, the NCCN supports treatment with cetuximab for metastatic colorectal cancer patients with wild-type KRAS gene (www(dot)nccn(dot)org/professional s/physiciangls/pdf/col on(dot)pdf). Subset analysis of the clinical trials reported above suggest that colon cancers are heterogeneous in their responsiveness to cetuximab. Thus, physicians need a diagnostic test that separates the patients likely to respond to cetuximab from those who are likely resistant to cetuximab. Embodiments of the present invention meet this need and solve this problem in the art, as described in further detail below, by providing a CMS classifier score that is predictive of positive response to cetuximab for patients with metastatic colon cancer, and for cetuximab resistance.

The cohort analyzed here (GSE5851) consisted of 80 colon cancer metastases hybridized to hgu133a Affymetrix microarrays. Clinical characteristics of the patients, 68 of which were treated with cetuximab, are found in Table 6 (Traits of GSE5851).

TABLE 6

| TRAIT | n |
| --- | --- |
| biopsy tissue (liver/other) | 61/19 |
| KRAS status (mutated/WT/NA) | 27/43/10 |
| response to cetuximab (CR/PR/SD/PD/UTD) | 1/5/19/43/12 |

The CMS classifier scores can be computed precisely for datasets based on Affymetrix hgu133plus2 arrays, RNA-seq and/or some other platforms. However, some of the hgu133plus2 probes used to compute the CMS classifier scores are missing from the hgu133a platform. For that reason, we computed approximations to the CMS classifier scores using the expression values of the hgu133a probes in the Affymetrix training set as follows.

ETsing the risk scores for panel genes represented by probes in hgu133a, we first computed 133a-pre-scores for each CMS subtype in the Affymetrix training set as the mean of the relevant risk scores. Because CMS classifier scores were defined for each sample in the Affymetrix training set, each 133a-pre-score value approximates CMS classifier score values through these samples. To create a smooth, steadily increasing approximation, we fit a loess smooth curve with response variable CMS classifier score and covariate 133a-pre-scores for the Affymetrix training set. This smooth curve is defined to be the CMS score-133a approximated through the hgu133a panel genes. One such score exists for each of CMS1-4. The root mean square error of the ability of the CMS score—133a to approximate the CMS classifier score, for each of CMS1-4 were CMS1: 0.07, CMS2: 0.03, CMS3: 0.12, CMS4: 0.04, showing that these approximations were sufficiently close so that tests of treatment response with respect to each were likely to yield comparable results.

For each samples in GSE5851 and each CMS subtype, the CMS score-133a for s was computed by finding the sample tin the Affymetrix Training set with the pre-score—133a closest to the pre-score-133a of s; then the CMS score-133a oft was the score value for s. Using the CMS classifier scores, the CMS subtypes, CMS 1-4 were defined as they were for Affymetrix training and validation cohorts.

The ability of the CMS classifier scores to predict responsiveness to cetuximab treatment was tested with Cox proportional hazards survival models with days of progression-free survival as endpoint. We found that the CMS2 score-133a was significantly predictive of a positive response to cetuximab with p-value 9×10 5 is the GSE5851 samples treated with cetuximab (n=68), and predictive with p-value 0.02 in those treated samples with wild type KRAS(n=39). None of the other CMS scores were significantly predictive of response or resistance using progression-free survival as endpoint.

Responsiveness to cetuximab were also reported in discrete categories, CR=complete response, PR=partial response, SD=stable disease, PD=progressive disease. The CMS1 subtype defined by the CMS classifier/methodology was distinguished in that all 8 samples in the subtype had progressive disease, indicating likely resistance to cetuximab in this subtype.

Thus, the CMS2 score was predictive of positive response to cetuximab in a cohort (GSE5851) of samples from patients with metastatic colon cancer and samples in the CMS1 subtype defined by the CMS classifier/methodology were resistant to cetuximab.

CMS Classifier/Methodology Predicts Response to FOLFIRI Treatment

The most frequently used chemotherapy regimen for treating colorectal cancer is FOLFOX, a combination of leucovorin calcium (folinic acid), fluorouracil, and oxaliplatin. An alternative regimen is FOLFIRI, a multidrug cocktail that replaces oxaliplatin with irinotecan. FOLFIRI may be used instead of FOLFOX, especially for metastatic patients. In the overall population of colon cancer patients, FOLFOX is the standard of care. This choice is based on the PETACC-3 clinical trial, in which a random population of stage III colon cancer patients, those treated with FOLFIRI had comparable long-term expected relapse-free survival to those treated with FOLFOX. However, some subpopulations of colon cancer patients appear to be resistant to FOLFOX, in particular, the mesenchymal CMS4 subtype.

Embodiments of the present disclosure were able to determine, in two independent cohorts, CMS4 patients that were highly responsive to FOLFIRI.

Affymetrix hgu133plus 2 microarray data (Cohort F) from colorectal cancer tumors (primary and metastatic) treated with FOLFIRI were obtained from GSE72970 and GSE62080 (n=106). Each patient has been classified as a "responder" or a "non-responder" based on the rate of progression of the disease following treatment.

To discover hypotheses of the relationship between the inventive CMS scores and FOLFIRI responsiveness, we use Cohort G (n=239), derived from samples in GSE14333 and GSE17536. Using a previously published signature predictive of FOLFIRI response, samples in Cohort G were classified as likely to be responsive or non-responsive to FOLFIRI.

The samples in Cohort G and Cohort F were normalized together using fRMA and ComBat to control for batch effects. Recall that samples in Cohort G were included in the Affymetrix training and validation sets, hence, the inventive CMS scores were previously defined for these samples. The inventive CMS scores were fit to all samples in this study using previously described methods with Cohort G as a reference set.

Cohort G was used to discover hypothetical dependencies of FOLFIRI response to the inventive CMS scores. We found that FOLFIRI response has the strongest dependence on CMS4 score ($p<2.2\times10^1$). The best partition of samples by FOLFIRI response was as CMS4 score >0.4 (responsive) and CMS4 score <0.4 (non-responsive). Adding other CMS scores in a multi-variable model did not improve on CMS4 score alone.

The CMS4 predictor of FOLFIRI response was verified in Cohort F. Patients in Cohort F with CMS4 score >0.4 were significantly ($p=8.0\times10^4$) more likely to be responsive to FOLFIRI (38 responders, 26 non-responders) than patients with CMS4 score ≤0.4 (11 responders, 31 non-responders).

Thus, in the cohort of patients from GSE72970 and GSE62080 treated with FOLFIRI (n=106), patients with CMS4 score >0.4 are likely to respond positively to FOLFIRI and those with CMS4 score≤0.4 are likely to be resistant to FOLFIRI. Combining these results, supports the use of the CMS classifier to select colorectal cancer patients who are more likely to respond to FOLFIRI than to FOLFOX.

CMS and Risk Classifiers/Methodologies Identify High-Risk Stage II Colon Cancer Patients Responsive to Standard Chemotherapy Clinical trials such as QUASAR showed that stage II colon cancer patients treated with standard chemotherapy (5-Fu) did not have better outcomes than those who only received observation. Based on these results, the standard of care for stage IIA and IIB colon cancer patients is to not administer chemotherapy post-surgery, even though 15% of these patients are likely to relapse within five years. Analysis of sensitivity to 5-Fu by consensus molecular subtype showed that patients in CMS 1-3 may respond to 5-Fu, while those in CMS4 are likely resistant to the treatment. Because clinical trials like QUASAR could not segregate patients by CMS, this differential response was not identified.

Using the inventive CMS classifier/methodology, a stage IIA and IIB colon cancer patient can be diagnosed as CMS 1-4, or Mixed. Patients classified or diagnosed with CMS4 colon cancer can be treated with FOLFIRI (based on an analysis of FOLFIRI sensitivity herein). For a patient not in CMS4 (i.e., CMS1-3, or Mixed subtype), the inventive Risk classifier can be used to identify the patient as at high risk of relapse, or low risk of relapse. If the patient is at high risk of relapse, then treatment with 5-Fu can be recommended and/or administered. If the patient is at low risk of relapse, then observation alone can be recommended and/or administered (e.g., after surgery). Thus, embodiments of the present disclosure can inform and/or dictate modification and/or confirmation of a particular treatment protocol based in CMS and/or Risk information not previously available to the physician and patient at clinic.

Additional Preferred Embodiments

Inspection of the p-value column in Table 3a, above, shows that many genes besides the preferred 5 genes are significantly predictive of the subtypes, suggesting that significant predictive scores for CMS subtypes could be defined with alternative sets of genes. This hypothesis is tested below, along with the evaluation of scores derived from sets of 2, 3, 7, or 10 genes, to establish the following assertions.

Analysis of the significance of scores as predictive of CMS subtypes derived from sets of genes establish the following assertions:
1. Scores derived from 2 or 3 of the top 25 genes are likely to be commercially viable but inferior to CMS classifier scores based on the preferred 5 genes;
2. Scores derived from 5 of the top 50 genes are likely to be commercially viable and all but the CMS2 score will be equivalent to CMS classifier scores based on the preferred 5 genes;
3. Scores derived from 5 of the top 100 genes are likely to be commercially viable but inferior to CMS classifier scores based on the preferred 5 genes;
4. Scores derived from 7 of the top 50 genes are likely to be equivalent to CMS classifier scores based on the preferred 5 genes;
5. Scores derived from 7 of the top 100 genes are likely to be commercially viable and all but the CMS2 score are likely to be equivalent to CMS classifier scores based on the preferred 5 genes;
6. Scores derived from 10 of the top 100 genes are likely to be equivalent to CMS classifier scores based on the preferred 5 genes;

Based on evaluations of CMS prediction tools in the literature, we considered a predictive score to be "commercially viable" if the AUC is at least 0.80. Based on the levels of significance of CMS classifier scores in validation sets, we considered a tool to be "equivalent to CMS classifier scores based on the preferred 5 genes" if the AUC is at least 0.88. Our assertions were tested by computing AUC values in the Affymetrix validation set.

Considering Item 3 above, e.g., it was impractical to test each of the 300 million possible 5-gene scores generated from the 400 genes in Table 3a. Instead, we estimated the significance of an arbitrary 5-gene score using probabilistic sampling, which states that the AUC of an arbitrary 5-gene score is effectively the same as the AUC of an arbitrary 5-gene score from a large subset of possible scores. For this study, we generated and analyzed a set of 500 randomly sampled scores. We further asserted that a predictive score was "likely" to be commercially viable if at least 0.70 of the 500 generated scores were commercially viable.

To test Item 3, e.g., we randomly sampled 500 5-gene sets from the top 100 genes in Table 3a for each of CMS1-4. We then computed the corresponding CMS1-4 scores, 500 each, and then the AUC values of the scores in the Affymetrix validation set. The predictive significance of an arbitrary such score was then assessed by computing the fraction of such AUC values that were above 0.80 (commercially viable) and above 0.88 (equivalent to CMS classifier scores based on the preferred 5 genes).

Simulations were carried out to assess the levels of significance of scores defined from 2, 3, 5, 7, 10 genes sampled from the top 10, 25, 50, 100 candidate genes, with results reported in Table 7. These results establish Items 1-6.

TABLE 7

| CMS subtype | Panel length | Ranks of genes | Probability >0.88 | Probability >0.80 |
|---|---|---|---|---|
| CMS1 | 2 | 1 to 10 | 0.26 | 0.69 |
| CMS2 | 2 | 1 to 10 | 0 | 1 |
| CMS3 | 2 | 1 to 10 | 0.4 | 1 |
| CMS4 | 2 | 1 to 10 | 1 | 1 |
| CMS1 | 2 | 1 to 25 | 0.18 | 0.76 |
| CMS2 | 2 | 1 to 25 | 0.03 | 0.98 |
| CMS3 | 2 | 1 to 25 | 0.35 | 0.98 |
| CMS4 | 2 | 1 to 25 | 1 | 1 |
| CMS1 | 3 | 1 to 10 | 0.4 | 0.87 |
| CMS2 | 3 | 1 to 10 | 0 | 1 |
| CMS3 | 3 | 1 to 10 | 0.81 | 1 |
| CMS4 | 3 | 1 to 10 | 1 | 1 |
| CMS1 | 3 | 1 to 25 | 0.4 | 0.93 |
| CMS2 | 3 | 1 to 25 | 0.11 | 1 |
| CMS3 | 3 | 1 to 25 | 0.62 | 1 |
| CMS4 | 3 | 1 to 25 | 1 | 1 |
| CMS1 | 5 | 1 to 25 | 0.68 | 0.99 |
| CMS2 | 5 | 1 to 25 | 0.3 | 1 |
| CMS3 | 5 | 1 to 25 | 0.87 | 1 |
| CMS4 | 5 | 1 to 25 | 1 | 1 |
| CMS1 | 5 | 1 to 50 | 0.82 | 1 |
| CMS2 | 5 | 1 to 50 | 0.49 | 1 |
| CMS3 | 5 | 1 to 50 | 0.75 | 1 |
| CMS4 | 5 | 1 to 50 | 1 | 1 |
| CMS1 | 5 | 1 to 100 | 0.83 | 1 |
| CMS2 | 5 | 1 to 100 | 0.36 | 1 |
| CMS3 | 5 | 1 to 100 | 0.71 | 1 |
| CMS4 | 5 | 1 to 100 | 1 | 1 |
| CMS1 | 7 | 1 to 50 | 0.89 | 1 |
| CMS2 | 7 | 1 to 50 | 0.7 | 1 |
| CMS3 | 7 | 1 to 50 | 0.94 | 1 |
| CMS4 | 7 | 1 to 50 | 1 | 1 |
| CMS1 | 7 | 1 to 100 | 0.94 | 1 |
| CMS2 | 7 | 1 to 100 | 0.66 | 1 |
| CMS3 | 7 | 1 to 100 | 0.88 | 1 |
| CMS4 | 7 | 1 to 100 | 1 | 1 |
| CMS1 | 10 | 1 to 100 | 0.99 | 1 |
| CMS2 | 10 | 1 to 100 | 0.89 | 1 |
| CMS3 | 10 | 1 to 100 | 0.95 | 1 |
| CMS4 | 10 | 1 to 100 | 1 | 1 |

Figure 8:
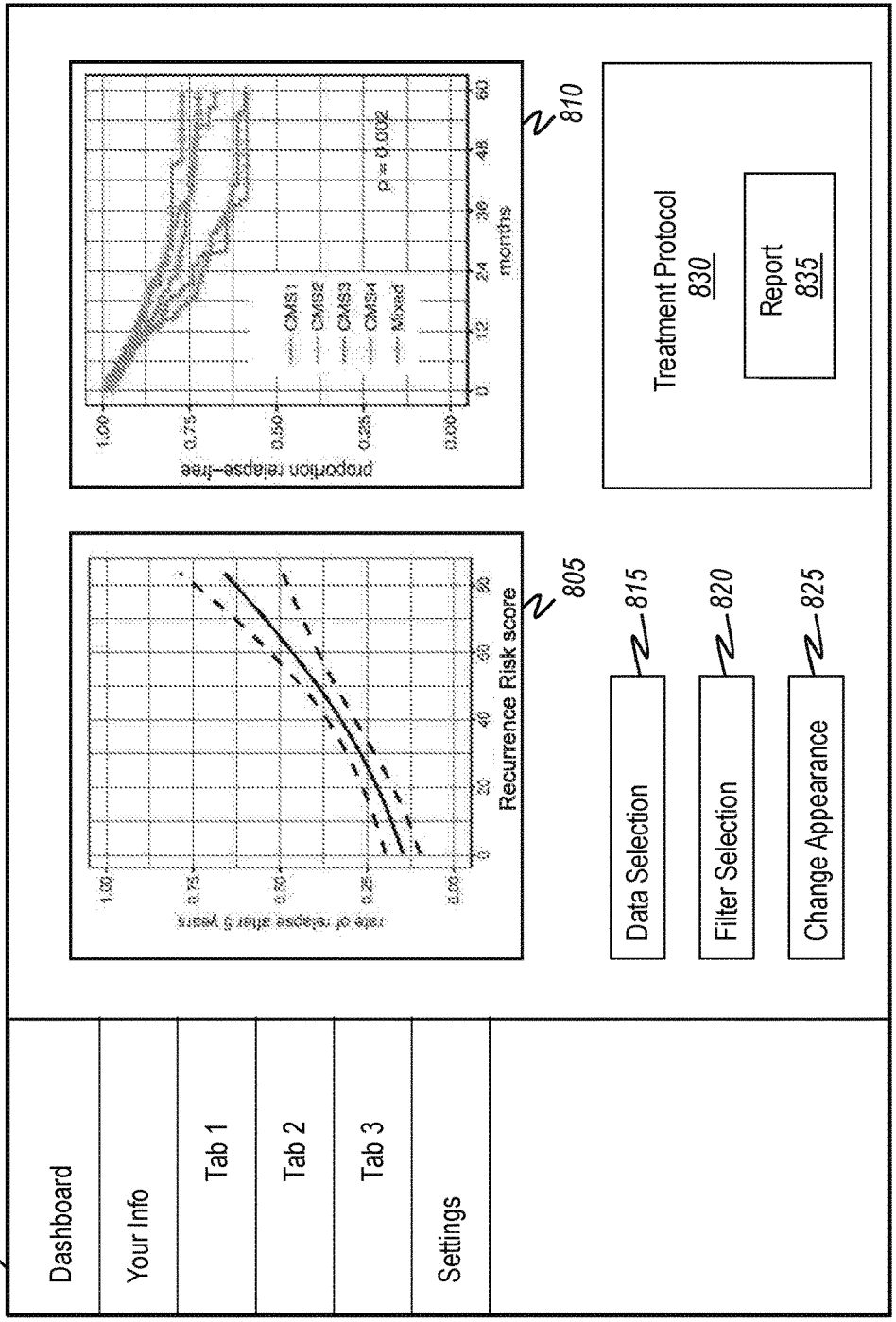
FIG. 8 illustrates a user interface in accordance with an embodiment or aspect of the present disclosure.

FIG. 8 illustrates an example user interface 800 that may be used to visually display any of the information described above. The user interface may display any number of graphs. The user interface 800 may also display any number of scores, such as one or more CMS scores, as described herein. Illustratively, a graph 805 and/or a graph 810 may be or comprise one or more tables, lists, charts, etc., which present or convey data in the user interface 800. In certain embodiments, a graph 805 and/or a graph 810 may present or convey a CMS classification or subtype determination. In some embodiments, CMS score(s) may be presented without a specific diagnosis or CMS determination. However, the CMS score(s) can be representative, informative, and/or determinative with regard CMS classification, in some embodiments.

User interface 800 also includes an option 815 to select different data on which to display a plot or graph. That is, by selecting option 815, a user can manually change the data he/she is using and working with. As such, user interface 800 is highly configurable and flexibly allows a user to operate with any amount of data. User interface 800 also includes an option 820 to apply one or more filter(s) onto the data. The filters may include any kind of filter. For instance, the data may be filtered by user, by date, by data type (e.g., colorectal cancer data as opposed to other types cancer data), health care provider, primary care physician, and so on. Any other filter may be used as well, where these filters allow a user to refine, or rather to narrow, the focus of the data that is current being viewed and/or manipulated. User interface 800 also includes an option 825 to change the visual appearance of user interface 800. For instance, by selecting option 825, a user can change or otherwise modify the background features of user interface 800 in an effort to customize or tailor user interface 800 in accordance with that user's personal preferences (e.g., language selection, font selection, font size selection, and so on).

User interface 800 also includes a section for visually displaying a treatment protocol 830 that has been developed, in accordance with the principles described above. This treatment protocol 830 may be provided to assist the user in more fully understanding a person's current ailment and how that ailment may be remedied. In some cases, a report 835, which includes the information described earlier, may also be visually displayed within user interface 800. Accordingly, it will be appreciated that user interface 800 may visually present information in accordance with a predefined visual layout. This visual layout may be configured, tailored, or otherwise customized in any manner to improve how the user interacts with the computer system. As such, user interface 800 provides substantial benefits and helps users in understanding the disclosed operations.

Figure 9:
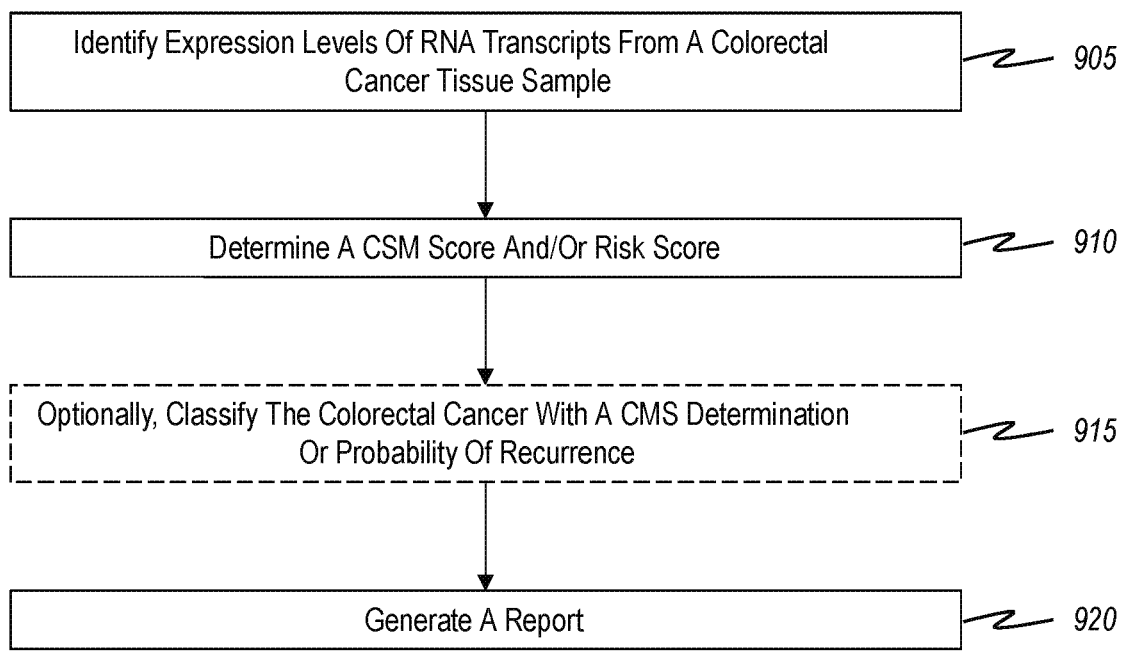
FIG. 9 illustrates a flowchart outlining a method in accordance with an embodiment or aspect of the present disclosure.

FIG. 9 illustrates a flowchart of an example method 900 for visually displaying a treatment protocol for a patient, where the treatment protocol is specific for a particular type of colorectal cancer. It will be appreciated that any of the displayed information may be displayed in the user interface 800 of FIG. 8. Furthermore, it will be appreciated that method 900 may be performed by a computer system, such as the one shown in FIG. 10, which will be discussed later. In some embodiments, one or more acts of method 900 can include multiple sub-acts.

Method 900 initially includes an act 905 of identifying expression levels of RNA transcripts from a colorectal cancer tissue sample. This act may be performed in any of the manners discussed earlier. In some embodiments, for example, act 905 includes identify expression levels of (each of at least twelve) RNA transcripts from a colorectal cancer tissue sample. The colorectal cancer can be of unknown consensus molecular subtype (CMS). The RNA transcripts can comprise at least three RNA transcripts from each of one, two, three, or four groups of genetic elements, each of the groups of genetic elements can define, represent, or correspond to a CMS gene expression profile specific for a different one of CMS1, CMS2, CMS3, and/or CMS4. In some embodiments, the RNA transcripts can be from a group of genetic elements that define, represent, or correspond to a risk of recurrence for the colorectal cancer.

Furthermore, a database or clearinghouse may be provided to store each patient's information. In some cases, the embodiments may obtain information about the sample from the database.

Method 900 also includes act 910 of determining a score. In some embodiments, the score can be a CMS score, as described herein. Act 910 can include, for example, determining, based on the expression level of each of (at least three) RNA transcripts from each of one, two, three, or four groups of genetic elements, a first, second, third, and/or fourth CMS score representative of a probability that the CMS of the colorectal cancer is CMS1, CMS2, CMS3, and/or CMS4, as described herein. In some embodiments, this act first includes determining, based on the expression level of each of the at least three RNA transcripts from a first group of the four groups of genetic elements, a first CMS score representative of a probability that the CMS of the colorectal cancer is CMS1. Then, this act includes determining, based on the expression level of each of the at least three RNA transcripts from a second group of the four groups of genetic elements, a second CMS score representative of a probability that the CMS of the colorectal cancer is CMS2. This act may additionally include determining, based on the expression level of each of the at least three RNA transcripts from a third group of the four groups of genetic elements, a third CMS score representative of a probability that the CMS of the colorectal cancer is CMS3. Finally, this act may include determining, based on the expression level of each of the at least three RNA transcripts from a fourth group of the four groups of genetic elements, a fourth CMS score representative of a probability that the CMS of the colorectal cancer is CMS4. All of the foregoing acts (or sub-acts) as described herein.

In some embodiments, the score can be a recurrence Risk score. Act 910 can include, for example, determining, based on the expression level of (at least fifteen) RNA transcripts, a risk score representative of a probability of recurrence for the colorectal cancer, as described herein.

Method 900 also includes an optional act 915 of classifying the colorectal cancer, as described herein. Act 910 can include, for example, classifying the colorectal cancer with a CMS determination corresponding to a particular CMS and/or based at least in part on the CMS scores (e.g., when one or more of the CMS scores are above a respective predictive threshold), as described herein. Act 910 can include classifying the colorectal cancer with a likelihood, risk, or probability of recurrence, as described herein.

Method 900 is also shown as including act 920 of generating a report. The report can display the CMS scores and/or Risk score, a probability or likelihood related thereto, and/or a determination based at least in part thereon. This report may be displayed as report 835 from FIG. 8. In some embodiments, this act includes generating a report indicating one or more of the first, second, third, and/or fourth CMS scores. In some cases, the report also indicates the probability that the CMS of the colorectal cancer is CMS1, CMS2, CMS3, and/or CMS4, In some cases, (i) one or more of the first, second, third, and/or fourth CMS scores and (ii) the probability that the CMS of the colorectal cancer is CMS1, CMS2, CMS3, and/or CMS4 signifies, at least in part, a treatment protocol specific for the CMS of the colorectal cancer, such as treatment protocol 830 shown in FIG. 8. In some embodiments, the report can display and/or indicate one or more of (i) the probability of recurrence for the colorectal cancer and (ii) a treatment protocol based at least in part on the probability of recurrence for the colorectal cancer. Any of the foregoing as described herein.

Additional and/or alternative method steps and/or acts, as described herein, can be incorporated into method 900.

Accordingly, the disclosed embodiments are able to perform a number of different operations in order to dynamically develop a treatment protocol for a user. This treatment protocol may then be visually displayed on a user interface for the user to view and interact with. For instance, if the treatment protocol requires the user to perform multiple steps, then the user interface can track the progression of the user's progress and provide a progression report. Additionally, the user interface can provide milestones or benchmark goals that the user should try to reach. The user interface can monitor the user's performance in achieving these goals.

In some cases, if the user prematurely ends a session or treatment step, then the user interface can record the user's current status with regard to the treatment protocol and can prompt the user to pick up where he/she previously left off. In this regard, one or more alerts can be provided to the user to alert the user regarding his/her status relative to the treatment protocol.

Figure 10:
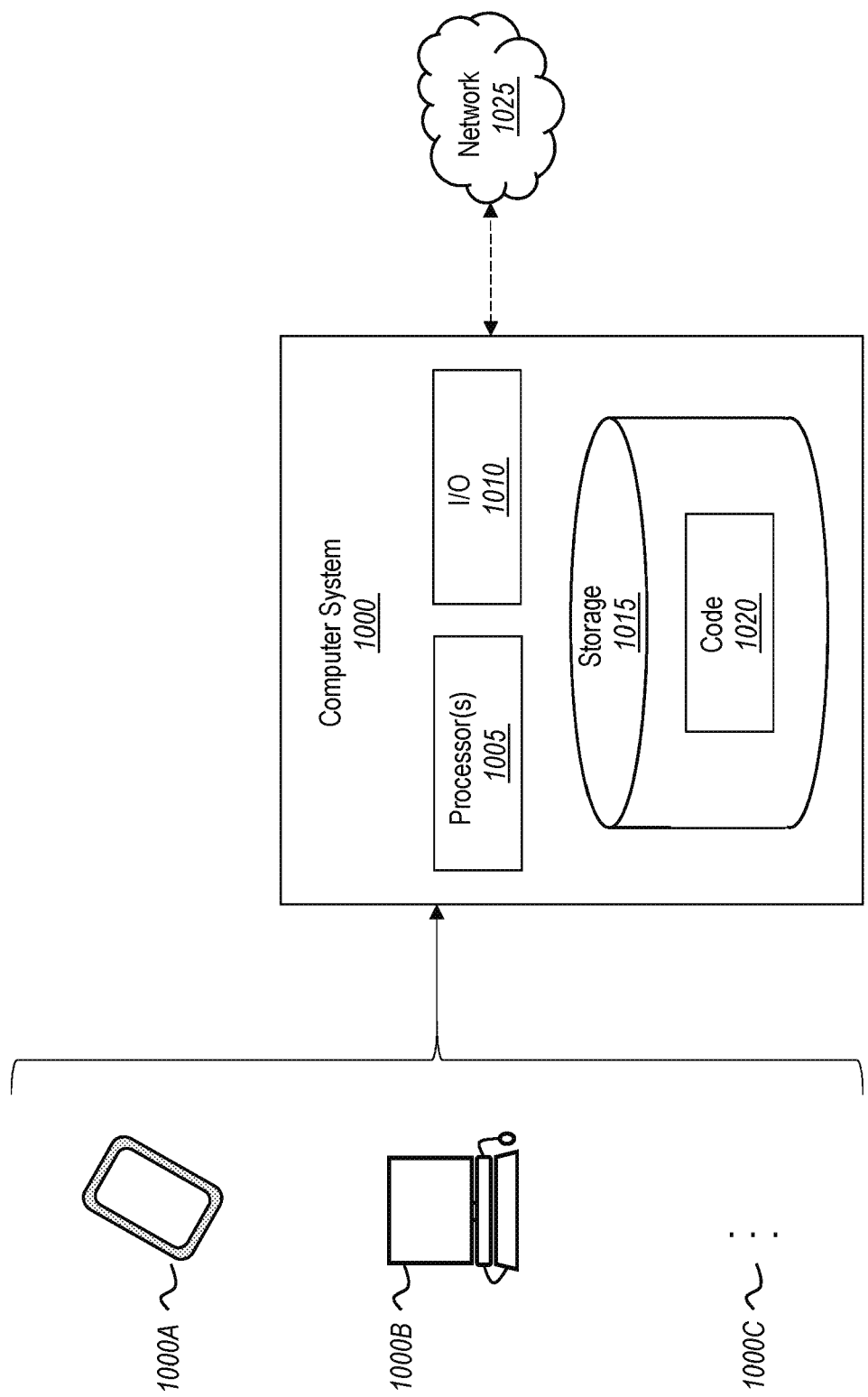
FIG. 10 illustrates a computer system in accordance with an embodiment or aspect of the present disclosure.

Attention will now be directed to FIG. 10 which illustrates an example computer system 1000 that may be used to facilitate the disclosed methods. It will be appreciated that computer system 1000 may be configured within various form factors. For example, computer system 1000 may be embodied as a tablet 1000A or a desktop 1000B. The ellipsis 1000C demonstrates that computer system 1000 may be embodied in various other forms too. For instance, computer system 1000 may also be a distributed system that includes one or more connected computing components/devices that are in communication with computer system 1000, a laptop computer, a mobile phone, a server, a data center, and/or any other computer system. The ellipsis 1000C also indicates that other system subcomponents may be included or attached with the computer system 1000, including, for example, sensors that are configured to detect user attributes (e.g., heart rate sensors, tissue sample analyzers, etc.), as well as sensors like cameras and other sensors that are configured to detect user data, all of which sensor data may comprise different types of information used during application of the disclosed embodiments.

In its most basic configuration, computer system 1000 includes various different components. For example, FIG. 10 shows that computer system 1000 includes at least one processor 1005 (aka a "hardware processing unit"), input/output ("I/O") 1010, and storage 1015.

Storage 1015 is shown as including executable code/instructions 1020. Storage 1015 may be physical system memory, which may be volatile, non-volatile, or some combination of the two. The term "memory" may also be used herein to refer to non-volatile mass storage such as physical storage media. If computer system 1000 is distributed, the processing, memory, and/or storage capability may be distributed as well. As used herein, the term "executable module," "executable component," or even "component" can refer to software objects, routines, or methods that may be executed on computer system 1000. The different components, modules, engines, and services described herein may be implemented as objects or processors that execute on computer system 1000 (e.g. as separate threads).

The disclosed embodiments may comprise or utilize a special-purpose or general-purpose computer including computer hardware, such as, for example, one or more processors (such as processor 1005) and system memory (such as storage 1015), as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are physical computer storage media. Computer-readable media that carry computer-executable instructions are transmission media. Thus, by way of example and not limitation, the current embodiments can comprise at least two distinctly different kinds of computer-readable media: computer storage media and transmission media.

Computer storage media are hardware storage devices, such as RAM, ROM, EEPROM, CD-ROM, solid state drives (SSDs) that are based on RAM, Flash memory, phase-change memory (PCM), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1000 may also be connected (via a wired or wireless connection) to external sensors (e.g., one or more remote cameras, blood pressure sensors, heart rate monitors, tissue analyzers, etc.). Further, computer system 1000 may also be connected through one or more wired or wireless networks 1025 to remote systems(s) that are configured to perform any of the processing described with regard to computer system 1000.

A graphics rendering engine may also be configured, with processor 1005, to render one or more images within a user interface of computer system 1000 (e.g., user interface 800 from FIG. 8). EO 1010 may include the graphics rendering engine as well as any other hardware or software used to visually display information (e.g., user interface 800). In this regard, I/O 1010 may include monitors, input devices (e.g., a mouse and keyboard), acoustic devices, and so on.

A "network," like the network 1025 shown in FIG. 10, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1000 will include one or more communication channels that are used to communicate with the network 1025. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily)utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

Additionally, or alternatively, the functionality described herein can be performed, at least in part, by one or more hardware logic components (e.g., the processor 1005). For example, and without limitation, illustrative types of hardware logic components that can be used include Field-Programmable Gate Arrays (FPGAs), Program-Specific or Application-Specific Integrated Circuits (ASICs), Program-Specific Standard Products (ASSPs), System-On-A-Chip Systems (SOCs), Complex Programmable Logic Devices (CPLDs), Central Processing Units (CPUs), and other types of programmable hardware.

It will be appreciated that computer system 1000 may include one or more processors (e.g., processor(s) 1005) and one or more computer-readable hardware storage devices (e.g., storage 1015), where the storage devices include computer-executable instructions that are executable by the one or more processors to perform any method (e.g., method 900 presented in FIG. 9). In this regard, computer system 1000 is also highly flexible and can perform numerous operations.

RNA Quantification: Briefly, gene expression levels (or RNA expression levels, or RNA transcript levels, etc.) can be measured as known in the art. For instance, in some embodiments, RNA sequencing (RNA-Seq), including high throughput sequencing, can be used to determine which genes (or RNA transcripts) are expressed and quantify (or quantitate) the expression levels of these genes (or RNA transcripts).

Illustratively, (total) RNA for each sample can be converted into a sequencing library of template molecules for sequencing. Library preparation, as known in the art, on an Illumina Cluster Station and Genome Analyzer according to the protocol for the Illumina mRNA Sample preparation kit (Part #1004898, Rev A: Illumina, San Diego, CA). It will be appreciated, however, that other platforms, systems, apparatus, and protocols are known in the art and contemplated herein. Briefly, RNA (e.g., poly-A mRNA) can be purified or isolated from other components (e.g., from total RNA (2 g) using poly-T oligo-attached magnetic beads). The mRNA can then be fragmented, and the first strand of cDNA can be synthesized from the cleaved RNA fragments using reverse transcriptase and (random) primers. Following the synthesis of the second strand of cDNA (to form double stranded DNA representing the RNA transcripts), end repair can (optionally) be performed on overhangs using T4 DNA polymerase and Klenow DNA polymerase, followed by ligation of sequencing Adapters to the ends of the DNA fragments.

The cDNA fragments can be purified using a gel run (e.g., at 80 V for approximately 3 hours until the Orange G dye band reached the bottom of the gel). The gel can be stained with SYBR green to visualize the DNA band. Illustratively, a band (e.g., at 350-450 bp) can be excised vertically from the gel, which can then be dissolved at room temperature using a QIAquick Gel Extraction Kit (Qiagen, Valencia, CA). The purified cDNA templates can be enriched (e.g., for 15 cycles of PCR amplification) and validated (e.g., using a BioAnalyzer) to assess size, purity and concentration of the purified cDNA libraries. The cDNA libraries can then be processed for single end cluster generation (e.g., by being placed on an Illumina Cluster Station, according to the protocol outlined in the Illumina Genome Analysis User Guide (Part #11251649, RevA)).

The template cDNA libraries (1.5 g) can then be hybridized to a plate, chip, or array grid (e.g, a flow cell), amplified and linearized and denatured to create a flow cell with ssDNA ready for sequencing. Each flow cell can then be sequenced (e.g., on an Illumina GAIIX Genome Analyzer). Illustratively, each sample can undergo a single lane of sequencing (e.g., using single end sequencing for 76 cycles according to the protocol outlined in the Illumina Genome Analysis User Guide (Part #11251649, RevA)). After completion of the (76 cycle) sequencing run, quality control on reads can optionally be performed, and the raw sequence data can enter the CMS classifier or Risk classifier workflow described herein.

Alternatively, RT-PCR may be used to measure, collect, and/or quantify gene expression levels, as understood by those skilled in the art and/or described herein. Illustratively, the quantification of mRNA using RT-PCR can be achieved as either a one-step or a two-step reaction. The difference between the two approaches lies in the number of tubes used when performing the procedure. In the one-step approach, the entire reaction from cDNA synthesis to PCR amplification occurs in a single tube. On the other hand, the two-step reaction requires that the reverse transcriptase reaction and PCR amplification be performed in separate tubes.

In some embodiments, microarray expression profiling may also be used to measure, collect, and/or quantify gene expression levels, as understood by those skilled in the art and/or described herein. Illustratively, 2 ug of total RNA of sample and Stratagene Universal Human Reference can be amplified and labeled using Agilent's Low RNA Input Linear Amplification Kit. Sample and reference can be co-hybridized on a Custom Agilent 244K Gene Expression Microarray. The expression data can be Lowess normalized and the ratio of the Cy5 channel (sample) and Cy3 channel (reference) can be log 2 transformed to create gene expression values for 23,199 probesets. Probesets without gene annotations and genes with missing data in >20% of the samples can be removed, with remaining genes available for further analysis. Missing values in the remaining genes can be imputed with the mean value across all samples.

Compositions

Some embodiments can comprise a composition. The composition can comprise a mixture of cDNA molecules corresponding to (at least twelve or at least fifteen) RNA transcripts, as described herein. The (at least twelve) RNA transcripts can comprise (at least three) RNA transcripts from (each of two, three, or four) groups of genetic elements. Each of the (two, three, or four) groups of genetic elements can define, represent, or correspond to a CMS gene expression profile specific for a different one of CMS1, CMS2, CMS3, and CMS4, as described herein. The (at least fifteen) RNA transcripts can be from a group of genetic elements that define, represent, or correspond to a risk of recurrence for a colorectal cancer, as described herein.

Panels and Kits Comprising a Panel: Some embodiments of the present disclosure comprise kits. The kits can be useful in performing one or more diagnostic method (e.g., one or more of the inventive diagnostic methods of the present disclosure, e.g., CMS). In particular, the kits can be used in performing a method of predicting or determining a consensus molecular subtype (CMS) of colorectal cancer in a human patient. The kits can be useful (in a clinical setting) for rapid, reliable diagnosis, determination, prediction, and/or prognosis.

In some embodiments, a kit can comprise a plurality of oligonucleotide primers and/or probes comprising specific genetic sequence binding targets for a panel of genes, such as a panel of genes comprising those gene panels disclosed herein comprising the gene panel for CMS1, CMS2, CMS3, CMS4, or a combination of all of these sets of genes, or any combination of these gene sets. In a particular embodiment, the oligonucleotide primers and/or probes comprising specific genetic sequence binding targets are provided for the target genes comprising: AXIN2, SEMA5A, CDHR1, CTTNBP2, WARS, HPSE, ATP9A, GNLY, DACH1, EMP2AIP1 (for the CMS1 gene subset); POFUT1, QPRT, PLAGL2, CEL, TRIB2, DDX27, DUSP4, FSCN1, OSER1, and LYZ (for the CMS2 gene subset); TIMP3, CAPN9, VAV2, FCGBP, FBN1, IGFBP5, SPINK4, REG4, CEBPB, and CLCA1 (for the CMS3 gene subset); and MGP, AOC3, TINS1, CCDC80, SPOCK1, LMOD1, PLN, AKAP12, FERMT2, and HSPB8 (for the CMS4 gene set) and/or KRAS, NRAS, BRAF, EGFR, ERBB2, and UGT1A1 target genes. In some embodiments, the genetic sequence binding targets are affixed to a solid surface. These target moieties may comprise a polynucleotide (oligonucleotide), a protein, a peptide or a peptide nucleic acid.

The primers and/or probes can be configured to bind complementarily to respective portions DNA (e.g., cDNA of RNA transcripts from a colorectal cancer tissue sample). The primers can be configured to prime polymerase chain reaction of the cDNA. The probes can be configured to detect amplified cDNA.

In some embodiments, the primers and/or probes can be configured to bind complementarily to respective portions of cDNA of (at least twelve) RNA transcripts from a colorectal cancer tissue sample. The (at least twelve) RNA transcripts can comprise (at least three) RNA transcripts from each of the two, three, or four groups of genetic elements. Each of the two, three, or four groups of genetic elements can define, represent, or correspond to a CMS gene expression profile specific for a different one of CMS1, CMS2, CMS3, and CMS4. In some embodiments, the at least twelve RNA transcripts can comprise at least sixteen RNA transcripts and the at least sixteen RNA transcripts can comprise at least four RNA transcripts from each of the four groups of genetic elements. In some embodiments, the at least twelve RNA transcripts can comprise at least twenty RNA transcripts and the at least twenty RNA transcripts can comprise at least five RNA transcripts from each of the four groups of genetic elements. In some embodiments, the at least twelve RNA transcripts can comprise at least twenty-four RNA transcripts and the at least twenty-four RNA transcripts can comprise at least six RNA transcripts from each of the four groups of genetic elements, and so forth.

In some embodiments, the at least twelve RNA transcripts can comprise up to forty RNA transcripts and the up to forty RNA transcripts can comprise up to ten RNA transcripts from each of the four groups of genetic elements. In some embodiments, the at least twelve RNA transcripts can comprise up to forty-eight RNA transcripts and the up to forty-eight RNA transcripts can comprise up to twelve RNA transcripts from each of the four groups of genetic elements. In some embodiments, the at least twelve RNA transcripts can comprise up to eighty RNA transcripts and the up to eighty RNA transcripts can comprise up to twenty RNA transcripts from each of the four groups of genetic elements.

The (at least twelve) RNA transcripts can comprise (at least three and/or up to twenty-nine) RNA transcripts from a first group of genetic elements. The first group can comprise or consist of the genes represented by or corresponding to ENTREZ IDs 6418, 9219, 10855, 3191, 9037, 10079, 83737, 10140, 8313, 54891, 57798, 998, 7105, 23475, 6431, 3725, 81786, 9554, 1602, 57168, 401474, 139322, 1783, 29966, 80183, 8019, 3549, 27330, and/or 10451. Alternatively, the first group can comprise or consist of the genes represented by or corresponding to ENTREZ IDs 9219, 57168, 7105, 23475, and/or 998.

The (at least twelve) RNA transcripts can comprise (at least three and/or up to twenty-two) RNA transcripts from a second group of genetic elements. The second group can comprise or consist of the genes represented by or corresponding to ENTREZ IDs 5326, 112858, 1057, 6780, 23509, 51497, 430, 171023, 25980, 23475, 22919, 80183, 51526, 28951, 1056, 1846, 644, 9054, 55661, 54894, 58490, and/or 4212. Alternatively, the second group can comprise or consist of the genes represented by or corresponding to ENTREZ IDs 112858, 5326, 23509, 6780, and/or 1846.

The (at least twelve) RNA transcripts can comprise (at least three and/or up to twenty-six) RNA transcripts from a third group of genetic elements. The third group can comprise or consist of the genes represented by or corresponding to ENTREZ IDs 4217, 84666, 8857, 7078, 80150, 4151, 54596, 143458, 84189, 7410, 5937, 25837, 10753, 192134, 201501, 9509, 140828, 84624, 1290, 405753, 1278, 2335, 1295, 3488, 9254, and/or 155465. Alternatively, the third group can comprise or consist of the genes represented by or corresponding to ENTREZ IDs 7078, 80150, 84189, 84666, and/or 5937.

The (at least twelve) RNA transcripts can comprise (at least three and/or up to twenty-nine) RNA transcripts from a fourth group of genetic elements. The fourth group can comprise or consist of the genes represented by or corresponding to ENTREZ IDs 23414, 30008, 27295, 2737, 143903, 154810, 11037, 7145, 9590, 5178, 23194, 4256, 10000, 1410, 862, 4286, 83871, 421 1, 165, 6695, 1292, 9353, 4131, 8639, 5549, 54796, 147906, and/or 8828. Alternatively, the fourth group can comprise or consist of the genes represented by or corresponding to ENTREZ IDs 143903, 23414, 11037, 27295, and/or 165.

In some embodiments, the first, second, third, and fourth groups of genetic elements can each, independently, comprise at least, up to, and/or about 5, 10, 15, 20, 22, 25, 26, 29, 30, 40, 45, 50, 55, or 60 genetic elements, or any number of genetic elements or range of numbers of genetic elements therebetween, that define, represent, or correspond to a CMS gene expression profile specific for a different one of CMS1, CMS2, CMS3, and CMS4.

In some embodiments, the primers and/or probes can be configured to bind complementarily to respective portions of cDNA of (twenty, or at least fifteen) RNA transcripts from a colorectal cancer tissue sample. The (twenty five, twenty, or at least fifteen) RNA transcripts can be from a group of genetic elements that define, represent, or correspond to a gene set associated with a CMS subtype for colorectal cancer. In other embodiments, the group of genetic elements can comprise at least or up to 25, 30, 35, 40, 45, 50, 55, 60, 65, 70, or 75 genetic elements that define, represent, or correspond to a CMS subtype 1, 2, 3, or 4, or a combination signature derived from 1, 2, 3, or 4. Similarly, in some embodiments, the targets can comprise at least or up to 20, 25, 30, 35, 40, 45, 50, 55, 60, 65, 70, or 75 genetic targets..

In certain embodiments, the oligonucleotide primers and/or probes can be (i) respectively, disposed or contained in a plurality of reaction containers or (ii) bound to a substrate or surface thereof. The plurality of reaction containers can comprise sample tubes or wells (e.g., of a reaction plate). The reaction plate can be or comprise a 96- or 384-well plate, for example, or a plate with any suitable number of wells. The respective wells of the reaction plate can each contain a respective pair of primers (configured to prime polymerase chain reaction of a cDNA of one of (at least twelve or at least fifteen) RNA transcripts from a colorectal cancer tissue sample). Alternatively, or in addition, the respective wells of the reaction plate can each contain a respective probe or pair of probes (configured to bind complementarily to a cDNA of one of the (at least twelve or at least fifteen) RNA transcripts). The substrate can comprise a plate, chip, array, grid, or flow cell.

In certain embodiments, the kits can comprise one or more polymerase chain reaction reagents configured to (i) amplify DNA (e.g., the cDNA of the (at least twelve or at least fifteen) RNA transcripts), such as upon thermocycling and/or (ii) detect amplified DNA (e.g., the cDNA of the (at least twelve or at least fifteen) RNA transcripts). The one or more polymerase chain reaction reagents can be or comprise or be selected from the group consisting of a buffering agent, deoxynucleotide triphosphates, DNA polymerase, and detection reagent(s). The detection reagent(s) can be or comprise a (fluorescent and/or double-stranded DNA (dsDNA) binding) dye or a labeled probe.

In certain embodiments, the kits can comprise one or more one or more reverse transcription reaction reagents configured to produce cDNA of (at least twelve or at least fifteen) RNA transcripts. The one or more reverse transcription reaction reagents can be or comprise or be selected from the group consisting of a buffering agent, deoxynucleotide triphosphates, and reverse transcriptase Cancer treatments: Various cancer treatments or treatment protocols, including surgical removal of cancer, tumor(s), and/or tissue, chemotherapy, antibody/immunotherapy, radiation therapy, observation, etc. are known in the art and contemplated herein. In some cases, one or more (particular) treatment(s) or treatment protocol(s) can be or are known to be more effective than others, based at least in part on the type, stage, grade, CMS, risk of recurrence, or other characteristic or feature of the cancer. Commonly used chemotherapy drugs for colon cancer include leucovorin, fluorouracil, irinotecan, oxaliplatin, capecitabine, trifluridine, and tipiracil. Those skilled in the art will appreciate and understand which drug(s) are best suited to treat which cancers with which characteristic(s) or feature(s). The NCCN guidelines (2018) also gives guidance as to when to use 5-FU, FOLFOX, CAPEOX, cetuximab, panitumumab, vemurafenib, pembrolizumab, bevacizumab, nivolumab, and regorafenib for colon cancer.

Some patients (e.g., with advanced colon cancer) may benefit from immunotherapy with antibodies such as pembrolizumab (Keytruda), nivolumab (Opdivo), cetuximab, and so forth. External beam radiation therapy (EBRT) is also used to target certain cancer(s), tumor(s), or tissue(s).

Healthcare providers and patients empowered with the results, outcomes, information, recommendations, and diagnosis generated through or with embodiments of the present disclosure can make better and/or more-informed decisions with regards to treatments and treatment protocols. Indeed, certain embodiments can include determining and/or administering a treatment protocol based at least in part on the results, outcomes, information, recommendations, and diagnosis generated through or with embodiments of the present disclosure.

Example 1—Process for Determining CMS Scores and CMS Subtype, Report Format, and Gene Panels The present example presents a description of one application of the present methods and systems as a commercial service.

The following steps may be employed in providing an exemplary commercial service report, such as to a physician, health clinic, clinical laboratory, or other health care provider.

1. Extract mRNA from a human colon or rectal tissue sample (can be an FFPE tissue sample);
2. Quantify expression levels of a group of genes in four gene panels, one gene panel for each of four colon cancer subtypes CMS1, CMS2, CMS3, CMS4;
3. For each gene, identify a gene risk score (CMS1-score, etc.) value for the sample by reference to a reference table from a reference set of samples;
4. For the genes in the CMS1 panel, compute the CMS1 pre-score value of the sample as the average of the gene risk score values for the sample computed in #3; similarly, to compute the CMS2 pre-score, CMS3 pre-score, and CMS4 pre-score;
5. For CMS1, use a reference table to compare the sample's pre-score to the reference set to identify the CMS1 score of the sample; similarly, to identify the CMS2 score, CMS3 score, and CMS4 score;
6. For each of CMS1-4; compare the sample's score value with a threshold determined for a reference set of samples; define the sample's CMS subtype to be that subtype whose CMS score is highest among those that are above their thresholds; if no score is above its threshold, then the sample has an unclassified CMS subtype;
7. Prepare a report including the CMS score values, the CMS classification, and the correlations between the CMS scores or CMS subtypes and possible clinical treatments, with information on the historical clinical effectiveness of the possible treatment regimens for the CMS subtype. Correlations between a particular CMS subtype and a defined recommended potential treatment is predicated on published clinical research.

In one embodiment, the preferred gene panels for each of CMS1-4 consists of 10 genes each, as follows:

CMS1:
AXIN2, SEMA5A, CDHR1, CTTNBP2, WARS, HPSE, ATP9A, GNLY, DACH1, EPM2AIP1;
CMS2:
POFUS1, QPRT, PLAGL2, CEL, TRIB2, DDX27, DUSP4, FSCN1, OSER1, LYZ;
CMS3:
TIMP3, CAPN9, VAV2, FCGBP, FBN1, IGFBP5, SPINK4, REG4, CEBPB, CLCA1;
CMS4:
MGP, AOC3, TNS1, CCDC80, SPOCK1, LMOD1, PLN, AKAP12, FERMT2, HSPB8;

Example 2—Colorectal Cancer Molecular Subtype Report

The present example presents a report format that may be used in the practice, use and application of the methods and tests described herein. Such a report format may be used in reporting results of CMS subtype determinations generated for a particular subject or group of subjects, using the various methods and gene panels disclosed herein. By way of example, the report format may be used in generating a particular subject patient report of readings from a sample from the subject, such as a tissue sample provided from a clinical laboratory or physician, that will include a report of the four ColotypeR-CMS score values and a predicted CMS subtype for each patient subject sample.

REPORT FORMAT—ColotypeR Consensus Molecular Subtype Test Report
Date: _____
—Test Results Here—
We report the values of CMS1-score, CMS2-score, CMS3-score, CMS4-score, and predicted CMS subtype, along with results of DNA mutation tests (KRAS, NRAS, BRAF, EGFR, ERBB2, UGT1A1) bundled with ColotypeR-CMS testing.
■ ■ ■
Clinical Features of CMS Subtypes
CMS1:
Biological Features: There is significant overlap between CMS1 and the microsatellite instable-high (MSI-H) subtype[1] in stage I-III tumors, and CMS1 tumors exhibit a high degree of infiltration by cytotoxic lymphocytes[2]. CMS1 tumors are also likely to have CIMP-high methylation subtype[3] and high tumor mutation burden. Tumors with BRAF mutations are likely CMS1[1,3]. CMS1 tumors are largely found on the right side[4] and tend to originate as serrated polyps[5].
Frequency and prognosis: In stages I-III, 16% were found to be CMS1, with RFS 0.71 95% CI: 0.63-0.80 at 5 years[1]. In stage I-II, 5-year RFS was 0.78 95% CI: 0.68-0.89. CMS1 tumors had poor prognosis after relapse in the initial study[1], in agreement with earlier reports for MSI and BRAF-mutated tumors[6,7]. Among metastatic tumors, in retrospective analysis of CALGB/SWOG 80405[8], FIRE-3[9] and AGITG MAX[10] clinical trials, 18% of tumors were CMS1. Median overall survival independent of treatment was 15 months in CALGB/SWOG 80405, 13 months in FIRE-3 and 8.8 months in MAX, the worst outcomes of all CMS subtypes in these studies. Of note, in CALGB/SWOG 80405, only 48% of CMS1 tumors were MSI-H and 31% of MSI-H tumors were not CMS1.
Potential Treatment Strategies: In stages I-III, results of treatment for MSI tumors informs treatment of CMS1 tumors. In stage II, 5-Fu chemotherapy appears to have a negative effect on MSI tumors. Stage III CMS1 tumors were not associated with better response to oxaliplatin than fluorouracil plus leucovorin (FLUV) in NASBP C-07[11]. There are not indications of widespread resistance to FOLFOX in CMS1, except potentially those which also have high CMS4 score. Concerning metastatic CRC tumors, in CALGB/SWOG 80405[8], CMS1 patients treated with backbone chemotherapy (predominantly FOLFOX) plus bevacizumab had significantly better outcomes than those treated with backbone chemotherapy plus cetuximab (median OS 22.5 months versus 11.7 months, P<0.001). Checkpoint inhibitors, such as anti-PD-1 monoclonal antibodies nivolumab and pembrolizumab, are FDA approved for MSI-H CRC tumors after treatment with fluoropyrimidine, oxaliplatin, and irinotecan[12].
CMS2:
Biological Features: CMS2 is the canonical epithelial colorectal cancer subtype, with activation of WNT and MYC signaling and high degrees of somatic copy number alterations[1]. CMS2 tumors exhibit very low infiltration by cytotoxic lymphocytes, and microsatellite instability is rare[3]. CMS2 tumors are more common on the left side but can also be found in the right colon[4].
Frequency and prognosis: In stages I-III, 38% of CRC tumors were found to be CMS2, with RFS 0.75 95% CI: 0.70-0.80 at 5 years[1]. Among metastatic tumors, in retrospective analysis of CALGB/SWOG 80405[8], FIRE-3[9] and AGITG MAX[10] clinical trials, approximately 42% of tumors were CMS2. CMS2 tumors had the best median OS (24.4 months) in MAX, CALGB/SWOG 80405 (40 months) and FIRE-3 (31.9 months).
Potential Treatment Strategies: There were indications of positive response to 5-Fu and FOLFOX in CMS2[11,13] in stage II and III. Stage III CMS2 tumors were associated with better response to oxaliplatin than fluorouracil plus leucovorin (FLUV) in NASBP C-07[11]. Among metastatic tumors, KRAS wild-type CMS2 tumors had the best overall survival (42 months) with cetuximab+backbone chemotherapy (FOLFOX for 73% of patients) and this was superior (p=0.0046) to OS (36 months) with bevacizumab+backbone chemotherapy. However, the addition of bevacizumab to capecitabine did improve progression-free survival in CMS2 tumors in MAX. In FIRE-3, OS was 38 months for cetuximab+FOLFIRI and 31 months for bevacizumab+FOLFIRI (not statistically significant).
CMS3:
Biological Features: CMS3 is an epithelial colorectal cancer subtype, with evident metabolic dysregulation, low degrees of somatic copy number alterations and a small number of MSI-High tumors[1]. In the original study[1], 72% of CMS3 tumors were KRAS mutated, but 77% of KRAS mutated tumors were not CMS3. CMS3 tumors were evenly distributed between the left and right colon[4].
Frequency and Prognosis: In stages I-II, 13% of CRC tumors were found to be CMS3, with good RFS 0.80 95% CI: 0.72-0.88 at 5 years[1]. Among metastatic tumors, in retrospective analysis of CALGB/SWOG 80405[8], FIRE-3[9] and AGITG MAX[10] clinical trials, approximately 12% of tumors were CMS3. CMS3 tumors had moderate median OS (17.6 months) in MAX, CALGB/SWOG 80405 (24.3 months) and FIRE-3 (18.7 months).

Potential Treatment Strategies: In one study (n=661), stage II CMS3 tumors had good prognosis and did not benefit from 5-Fu chemotherapy[13], however, stage III CMS3 tumors did benefit from 5-Fu chemotherapy. Retrospective analysis of NASBP C-07 did not reveal a benefit for oxaliplatin over FLUV alone in stage III CMS3 tumors[11]. Among metastatic tumors, in retrospective analysis of CALGB/SWOG 80405[8] and FIRE-39, there was no significant difference in median OS between the treatment arms (cetuximab+backbone or bevacizumab+backbone).

CMS4

Biological Features: CMS4 is a mesenchymal colorectal cancer subtype, with TGF-beta signaling activity, and high degrees of somatic copy number alterations[1]. CMS4 tumors exhibited high degrees of infiltration by fibroblasts and endothelial cells[2] and were highly inflamed[3]. CMS4 tumors were evenly distributed between the left and right colon[4].

Frequency and prognosis: In stages I-III, 23% of CRC tumors were found to be CMS4, with RFS 0.63 95% CI: 0.56-0.71 at 5 years, the poorest of all CMS subtypes[1]. Among metastatic tumors, in retrospective analysis of CALGB/SWOG 80405[8], FIRE-39 and AGITG MAX[11] clinical trials, the CMS4 tumors ranged from 23%-34%. CMS4 tumors had relatively good prognosis (21.4 months in MAX, 31.4 months in CALGB/SWOG 80405, and 25.3 months in FIRE-3).

Potential Treatment Strategies: In stage II and stage III, retrospective analysis of NASBP C-07 did not reveal a benefit to FLUV treatment or oxaliplatin for CMS4 patients[14-16]. Numerous research studies report resistance to 5-Fu and regimens containing oxaliplatin among tumors with a mesenchymal subtype (CMS4)[17-21]. Research studies using samples from metastatic tumors, cell lines and xenografts also report that mesenchymal type tumors are likely sensitive to irinotecan[20,22-26]. Among metastatic tumors, in retrospective analysis of CALGB/SWOG 80405[8], median overall survival in CMS4 tumors treated with cetuximab+backbone therapy and bevacizumab+backbone therapy were both near 31 months, second best compared to CMS2 tumors. In FIRE-39, median OS of CMS4 was significantly better (p=0.016) in cetuximab+FOLFIRI (41 months) than bevacizumab+FOLFIRI (22 months). Analysis of the MAX trial did not show a benefit of adding bevacizumab to capecitabine[10].

Embodiments of the present disclosure provide systems and methods for determining the CMS of a colorectal cancer tumor and/or or an appropriate treatment protocol based on the CMS of a colorectal cancer tumor based on the positive predictive value (PPV) of an abbreviated gene expression profile.

While the present disclosure makes reference to specific exemplary embodiments, the present disclosure may also be embodied or implemented in other specific forms without departing from its spirit or essential characteristics. Accordingly, the disclosed embodiments are to be considered in all respects only as illustrative and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the disclosure. Such substitutions, alterations, and/or modifications are to be considered within the scope of this disclosure.

The scope of the invention is indicated by the appended claims rather than by the foregoing description of the present disclosure. The limitations recited in the claims are to be interpreted broadly based on the language employed in the claims and not limited to specific examples described in the present disclosure, including the detailed description, which examples are to be construed as non-exclusive and non-exhaustive. All changes which come within the meaning and range of equivalency of the claims are to be embraced within their scope.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment.

In addition, unless a feature is described as being required in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. It will be appreciated that while features may be optional in certain embodiments, when features are included in such embodiments, they can be required to have a specific configuration as described in the present disclosure.

Likewise, any steps recited in any method or process described herein and/or recited in the claims can be executed in any suitable order and are not necessarily limited to the order described and/or recited, unless otherwise stated (explicitly or implicitly). Such steps can, however, also be required to be performed in a specific order or any suitable order in certain embodiments of the present disclosure.

Furthermore, various well-known aspects of illustrative systems, methods, products, and the like are not described herein in particular detail in order to avoid obscuring aspects of the example embodiments. Such aspects are, however, also contemplated herein.

BIBLIOGRAPHY

The teachings of the following are incorporated herein by reference:

1. Guinney J, Dienstmann R, Wang X, et al. The consensus molecular subtypes of colorectal cancer. *Nat Med.* 2015; 21(11):1350-1356. doi:10.1038/nm.3967.
2. Becht E, de Reynies A, Giraldo N A, et al. Immune and Stromal Classification of Colorectal Cancer Is Associated with Molecular Subtypes and Relevant for Precision Immunotherapy. *Clin Cancer Res.* 2016; 22(16):4057-4066. doi:10.1158/1078-0432.CCR-15-2879.
3. Dienstmann R, Vermeulen L, Guinney J, Kopetz S, Tejpar S, Tabernero J. Consensus molecular subtypes and the evolution of precision medicine in colorectal cancer. *Nat Rev Cancer.* 2017; 17(2):79-92. doi:10.1038/nrc.2016.126.
4. Lee M S, Menter D G, Kopetz S. Right Versus Left Colon Cancer Biology: Integrating the Consensus Molecular Subtypes. *J Natl Compr Canc Netw.* 2017; 15(3):411-419.
5. Graham D M, Coyle V M, Kennedy R D, Wilson R H. Molecular Subtypes and Personalized Therapy in Metastatic Colorectal Cancer. *Current Colorectal Cancer Reports*. 2016; 12(3):1-10. doi:10.1007/s11888-016-0312-y.
6. Tran B, Kopetz S, Tie J, et al. Impact of BRAF mutation and microsatellite instability on the pattern of metastatic spread and prognosis in metastatic colorectal cancer. *Cancer*. 2011; 117(20):4623-4632. doi:10.1002/cncr.26086.
7. Popovici V, Budinska E, Bosman F T, Tejpar S, Roth A D, Delorenzi M. Context-dependent interpretation of the prognostic value of BRAF and KRAS mutations in colorectal cancer. *BMC Cancer*. 2013; 13(1):439. doi:10.1186/1471-2407-13-439.
8. Lenz H-J, Ou F-S, Venook A P, et al. Impact of Consensus Molecular Subtype on Survival in Patients With Metastatic Colorectal Cancer: Results From CALGB/SWOG 80405 (Alliance). *J Clin Oncol*. May 2019:JC01802258. doi:10.1200/JCO.18.02258.
9. Stintzing S, Wirapati P, Lenz H-J, et al. Consensus molecular subgroups (CMS) of colorectal cancer (CRC) and first-line efficacy of FOLFIRI plus cetuximab or bevacizumab in the FIRE3 (AIO KRK-0306) trial. *Journal of Clinical Oncology*. 2017; 35(15_suppl):3510-3510. doi:10.1200/JCO.2017.35.15_suppl.3510.
10. Mooi J K, Wirapati P, Asher R, et al. The prognostic impact of consensus molecular subtypes (CMS) and its predictive effects for bevacizumab benefit in metastatic colorectal cancer: molecular analysis of the AGITG MAX clinical trial. *Ann Oncol*. 2018; 29(11):2240-2246. doi:10.1093/annonc/mdy410.
11. Song N, Pogue-Geile K L, Gavin P G, et al. Clinical Outcome From Oxaliplatin Treatment in Stage I/III Colon Cancer According to Intrinsic Subtypes: Secondary Analysis of NSABP C-07/NRG Oncology Randomized Clinical Trial. *JAMA Oncol*. 2016; 2(9):1162-1169. doi:10.1001/jamaoncol.2016.2314.
12. Overman M. Where We Stand With Immunotherapy in Colorectal Cancer: Deficient Mismatch Repair, Proficient Mismatch Repair, and Toxicity Management. *ASCO Educational Book*. April 2018:239-247.
13. Allen W L, Dunne P D, McDade S, et al. Transcriptional subtyping and CD8 immunohistochemistry identifies poor prognosis stage II/III colorectal cancer patients who benefit from adjuvant chemotherapy. *JCO Precis Oncol*. 2018; 2018(2):1-15. doi:10.1200/PO.17.00241.
14. Song N, Pogue-Geile K L, Gavin P G, et al. Clinical Outcome From Oxaliplatin Treatment in Stage II/III Colon Cancer According to Intrinsic Subtypes. *JAMA Oncol*. 2016; 2(9):1162-16. doi:10.1001/jamaoncol.2016.2314.
15. Pogue-Geile K L, Song N, Gavin P G, et al. Clinical outcome and benefit of oxaliplatin in colon cancer according to intrinsic subtypes: Results from NRG Oncology/NSABP C-07. *Journal of Clinical Oncology*. 2016; 34(15_suppl):3510-3510. doi:10.1200/JCO.2016.34.15_suppl.3510.
16. Kim S R, Song N, Yothers G, et al. Tumour sidedness and intrinsic subtypes in patients with stage II/III colon cancer: analysis of NSABP C-07 (NRG Oncology). *Br J Cancer*. 2017; 118(5):629-633. doi:10.1038/bjc.2017.448.
17. Roepman P, Schlicker A, Tabernero J, et al. Colorectal cancer intrinsic subtypes predict chemotherapy benefit, deficient mismatch repair and epithelial-to-mesenchymal transition. *Int J Cancer*. 2013; 134(3):552-562. doi:10.1002/ijc.28387.
18. Thanki K, Nicholls M E, Gajjar A, et al. Consensus Molecular Subtypes of Colorectal Cancer and their Clinical Implications. *Int Biol Biomed J*. 2017; 3(3):105-111.
19. Li P, Zhang X, Wang H, et al. MALAT1 Is Associated with Poor Response to Oxaliplatin-Based Chemotherapy in Colorectal Cancer Patients and Promotes Chemoresistance through EZH2. *Mol Cancer Ther*. 2017; 16(4):739-751. doi:10.1158/1535-7163.MCT-16-0591.
20. Rodriguez-Salas N, Dominguez G, Barderas R, et al. Clinical relevance of colorectal cancer molecular subtypes. *Crit Rev Oncol Hematol*. 2017; 109:9-19. doi:10.1016/j.critrevonc.2016.11.007.
21. Fan C-W, Chen T, Shang Y-N, et al. Cancer-initiating cells derived from human rectal adenocarcinoma tissues carry mesenchymal phenotypes and resist drug therapies. *Cell Death and Disease*. 2013; 4(10):e828-12. doi:10.1038/cddis.2013.337.
22. Sadanandam A, Lyssiotis C A, Homicsko K, et al. A colorectal cancer classification system that associates cellular phenotype and responses to therapy. *Nat Med*. 2013; 19(5):619-625. doi:10.1038/nm.3175.
23. Okita A, Takahashi S, Ouchi K, et al. Consensus molecular subtypes classification of colorectal cancer as a predictive factor for chemotherapeutic efficacy against metastatic colorectal cancer. *Oncotarget*. 2018; 9(27):18698-18711. doi:10.18632/oncotarget.24617.
24. Del Rio M, Mollevi C, Bibeau F, et al. Molecular subtypes of metastatic colorectal cancer are associated with patient response to irinotecan-based therapies. *European Journal of Cancer*. 2017; 76:68-75. doi:10.1016/j.ejca.2017.02.003.
25. Sveen A, Bruun J, Eide P W, et al. Colorectal Cancer Consensus Molecular Subtypes Translated to Preclinical Models Uncover Potentially Targetable Cancer Cell Dependencies. *Clin Cancer Res*. 2018; 24(4):794-806. doi:10.1158/1078-0432.CCR-17-1234.
26. de Sousa E Melo F, Wang X, Jansen M, et al. Poor-prognosis colon cancer is defined by a molecularly distinct subtype and develops from serrated precursor lesions. *Nat Med*. 2013; 19(5):614-618. doi:10.1038/nm.3174.

What is claimed is:

1. A continuous score method for providing a colon cancer disease predicted consensus molecular subtype (CMS) comprising:
   a) contacting a genetic sample with a plurality of genetic sequence binding targets and measuring expression levels of a panel of genes having specificity for the binding targets, said panel of genes comprising at least three genes for each of four consensus molecular subtypes CMS1, CMS2, CMS3 and CMS4, wherein the gene subset for each of the four consensus molecular subtypes comprise:
   AXIN2, SEMA5A, CDHR1, CTTNBP2, WARS, HPSE, ATP9A, GNLY, DACH1, EMP2AIP1 for the CMS1 gene subset;
   POFUT1, QPRT, PLAGL2, CEL, TRIB2, DDX27, DUSP4, FSCN1, OSER1, and LYZ for the CMS2 gene subset;
   TIMP3, CAPN9, VAV2, FCGBP, FBN1, IGFBP5, SPINK4, REG4, CEBPB, and CLCA1 for the CMS3 gene subset; and
   MGP, AOC3, TINS1, CCDC80, SPOCK1, LMOD1, PLN, AKAP12, FERMT2, and HSPB8 for the CMS4 gene subset;

b) obtaining a gene expression signature value from the expression levels of at least three genes of the CMS1, CMS2, CMS3 and CMS4 gene subsets from the genetic sample;

c) comparing the gene expression signature value to a predicted threshold for the CMS subtype to provide a continuous CMS score for each CMS subtype;

d) selecting qualifying CMS scores that are above the predicted threshold for the CMS subtype;

e) ranking the qualifying CMS scores to provide ranked qualifying CMS scores for the genetic sample; and f) assigning one or more of a colon cancer disease predicted CMS to the genetic sample from the ranked qualifying CMS scores for the genetic sample, wherein the predicted CMS comprises the CMS of the highest ranked qualifying CMS score.

2. The method of claim 1, wherein said continuous score method provides a predicted CMS with improved reproducibility for a genetic sample compared to a CMS classification of a genetic sample without the continuous score method.

3. The method of claim 1 wherein the genetic sample comprises cDNA or RNA either in purified form or as a tissue lysate.

4. The method of claim 1 wherein the genetic sample is a from a human tissue sample.

5. The method of claim 4 wherein the genetic sample is extracted from a formalin-fixed paraffin-embedded human tissue.

6. A gene screening panel for human colon cancer disease subtype, said gene screening panel comprising genetic sequence binding targets for a panel of four gene sets for a human colon cancer disease subtype CMS1, CMS2, CMS3 or CMS4, said four gene sets comprising:

at least three genes of a CMS1 colon disease gene set comprising: AXIN2, SEMA5A, CDHR1, CTTNBP2, WARS, HPSE, ATP9A, GNLY, DACH1, and EMP2AIP1;

at least three genes of a CMS2 colon disease gene set comprising: POFUT1, QPRT, PLAGL2, CEL, TRIB2, DDX27, DUSP4, FSCN1, OSER1, and LYZ;

at least three genes of a CMS3 colon disease gene set comprising: TIMP3, CAPN9, VAV2, FCGBP, FBN1, IGFBP5, SPINK4, REG4, CEBPB, and CLCA1; and at least three genes of a CMS4 colon disease gene set comprising: MGP, AOC3, TINS1, CCDC80, SPOCK1, LMOD1, PLN, AKAP12, FERMT2, and HSPB8.

7. The gene screening panel of claim 6 wherein the genetic sequence binding targets are affixed to a solid surface.

8. The gene screening panel of claim 6 wherein the genetic sequence binding targets comprise a polynucleotide, a protein, a peptide, or a peptide nucleic acid.

9. A method for providing an enhanced treatment plan for a subject having a colon cancer disease predicted consensus molecular subtype (CMS) comprising:

identifying presence or absence of a colon cancer disease from a genetic sample of the subject, the genetic sample having a predicted CMS according to the continuous score method of claim 1;

providing the subject having a predicted CMS an enhanced treatment plan for the predicted CMS colon cancer disease, wherein the enhanced treatment plan provides an improved anti-colon cancer disease treatment for the subject's colon cancer disease subtype compared to an anti-cancer disease treatment for the subject's colon cancer disease subtype without a colon cancer disease subtype having a continuous score as provided in claim 1.

10. The method of claim 9, wherein the genetic sample identified with a predicted CMS is screened for gene mutations of a gene in a gene panel to provide a sample gene mutation factor, wherein said gene panel comprises at least three genes KRAS, NRAS, BRAF, EGFR, ERBB2, and UGT1A1.

11. The method of claim 9, wherein:

where the predicted CMS subtype is CMS1, CMS2, CMS3, or a combination thereof, the enhanced anti-colon cancer disease treatment plan is absent a chemotherapeutic agent; and where the predicted CMS subtype is CMS4, or a combination CMS comprising CMS4, the enhanced anti-colon cancer disease treatment plan comprises a chemotherapeutic agent.

12. The method of claim 11 wherein a treatment plan for the subject's colon cancer disease CMS without the predicted CMS having a qualified continuous score is clinically contraindicated for the subject's CMS.

13. The method of claim 9, wherein the subject is a human.

14. The method of claim 9, wherein the genetic sample comprises cDNA or RNA either in purified form or as a tissue lysate.

15. The method of claim 9 wherein the genetic sample from the subject is extracted from a formalin-fixed, paraffin embedded (FFPE) colorectal tissue sample from the subject.

16. The gene screening panel of claim 6 wherein the genetic sequence binding targets comprise a set of molecular probes or a set of oligonucleotide primer pairs having a detectable label, wherein said detectable label is a non-naturally occurring polynucleotide label.

17. A kit comprising the gene screening panel of claim 7.

* * * * *